(12) United States Patent
Bazan et al.

(10) Patent No.: US 7,928,198 B2
(45) Date of Patent: Apr. 19, 2011

(54) IL-B50 POLYPEPTIDE

(75) Inventors: J. Fernando Bazan, Menlo Park, CA (US); Rene de Waal Malefyt, Sunnyvale, CA (US); Yong-Jun Liu, Pearland, TX (US); Vassili Soumelis, Paris (FR)

(73) Assignee: Schering Corporation, Kenilworth, NJ (US)

( * ) Notice: Subject to any disclaimer, the term of this patent is extended or adjusted under 35 U.S.C. 154(b) by 252 days.

(21) Appl. No.: 12/174,889

(22) Filed: Jul. 17, 2008

(65) Prior Publication Data

US 2010/0130724 A1 May 27, 2010

Related U.S. Application Data

(63) Continuation of application No. 09/963,347, filed on Sep. 25, 2001, now abandoned, which is a continuation-in-part of application No. 09/399,492, filed on Sep. 20, 1999, now abandoned.

(60) Provisional application No. 60/131,298, filed on Apr. 27, 1999, provisional application No. 60/101,318, filed on Sep. 21, 1998.

(51) Int. Cl.
*C07K 14/00* (2006.01)
*C07K 1/00* (2006.01)
*C12P 21/06* (2006.01)
*C12P 21/04* (2006.01)

(52) U.S. Cl. ..... 530/351; 530/350; 435/69.1; 435/69.52

(58) Field of Classification Search .................. None
See application file for complete search history.

(56) References Cited

U.S. PATENT DOCUMENTS

| | | | |
|---|---|---|---|
| 4,281,061 A | 7/1981 | Zuk et al. | |
| 5,627,043 A | 5/1997 | Franzusoff | |
| 5,965,122 A | 10/1999 | Namen et al. | |
| 6,555,520 B2 | 4/2003 | Sims et al. | |
| 6,844,170 B1 | 1/2005 | Moore et al. | |
| 7,304,144 B2 | 12/2007 | Sims et al. | |
| 2002/0068323 A1 | 6/2002 | Saris et al. | |
| 2002/0173623 A1 | 11/2002 | Reche-Gallardo et al. | |
| 2003/0099947 A1 | 5/2003 | Bazan et al. | |
| 2006/0223754 A1 | 10/2006 | Sims et al. | |

FOREIGN PATENT DOCUMENTS

| | | |
|---|---|---|
| EP | 0314415 A2 | 5/1989 |
| WO | WO 00/29581 | 5/2000 |
| WO | WO 00/39149 | 7/2000 |

OTHER PUBLICATIONS

Bendayan, M., "Possibilities of False Immunocytochemical Results Generated by the Use of Monoclonal Antibodies: The Example of the Anti-proinsulin Antibody," The Journal of Histochemistry and Cytochemistry, vol. 43(9) pp. 881-886 (1995).
Bost, K., et al., "Antibodies Against a Peptide Within The HIV Envelope Protein Crossreacts with Human Interleukin-2," Immunological Investigations, vol. 17(6&7), pp. 577-586 (1988).
Carpino, N., et al., "Absence of an Essential Role for Thymic Stomal Lymphopoietin Receptor in Murine B-Cell Development," Molecular and Cellular Biology, vol. 24(6), pp. 2584-2592 (2004).
Fry, T., et al., "Interleukin-7: from bench to clinic," Blood, vol. 99 (11) pp. 3892-3904 (2002).
Gavilondo, J., et al., "Antibody Engineering at the Millennium," BioTechniques, vol. 29, pp. 128-145 (2000).
Gilliet M., et al., "Human Dendritic Cells Activated by TSLP and CD40L Induce Proallergic Cytotoxic T Cells," J. Exp. Med., vol. 197(8), pp. 1059-1063 (2003).
Isaksen, D., et al., "Requirement for Stat5 in Thymic Stromal Lymphopoietin-Mediated Signal Transduction, " The Journal of Immunology, vol. 163, pp. 5971-5977 (1999).
Janeway, C., "The Immune System in Health and Disease," Garland Science, 3$^{rd}$ Edition, pp. A:11 (1997).
Leonard, W., "TSLP: finally in the limelight," Nature Immunology, vol. 3(7) pp. 605-607 (2002).
Liu, Y., et al., "TSLP: An Epithelial Cell Cytokine that Regulates T Cell Differentiation by Conditioning Dendritic Cell Maturation," Ann. Rev. Immunol. vol. 25, pp. 193-219 (2007).
Liu, Y., "Thymic stromal lymphopoietin: master switch for allergic inflammation," The Journal of Experimental Medicine, vol. 203(2), pp. 269-273 (2006).
Park, L., et al., "Cloning of the Murine Thymic Stromal Lymphopoietin (TSLP) Receptor: Formation of a Functional Heteromeric Complex Requires Interleukin 7 Receptor," The Journal of Experimental Medicine, vol. 192(5), pp. 659-669 (2000).
Ray, R., et al., "Characterization of thymic stromal-derived lymphopoietin (TSLP) in murine B cell development in vitro," Eur. J. Immunol. vol. 26, pp. 10-16 (1996).
Reche, P., et al., "Human Thymic Stromal Lymphopoietin Preferentially Stimulates Myeloid Cells," The Journal of Immunology, vol. 167, pp. 336-343 (2001).
Rochman, I., et al., "Cutting Edge: Direct Action of Thymic Stromal Lymphopoietin on Activated Human CD4$^+$T Cells", The Journal of Immunology, vol. 178, pp. 6720-6724 (2007).
Sims, J., et al., "Molecular Cloning and Biological Characterization of a Novel Murine Lymphoid Growth Factor", The Journal of Experimental Medicine, vol. 192, No. 5, pp. 671-680 (2000).
Soumelis, V., et al., "Human epithelial cells trigger dendritic cell-mediated allergic inflammation by producing TSLP," Nature Immunology, vol. 3(7), pp. 673-680 (2002).
Soumelis, V., et al., "Human thymic stromal lymphopoietin: a novel epithelial cell-derived cytokine and a potential key player in the induction of allergic inflammation," Springer Semi Immun., vol. 25, pp. 325-333 (2004).
Voβhenrich, C., et al., "Thymic stromal-derived lymphopoietin distinguishes fetal from adult B cell development," Nature Immunology, vol. 4(8) pp. 773-779 (2003).
Wang, J., et al., "Human TSLP-Educated DCs," Cellular & Molecular Immunology, vol. 5(2), pp. 99-106 (2008).

(Continued)

*Primary Examiner* — Olga N Chernyshev

(57) ABSTRACT

Purified genes encoding cytokines from a mammal, reagents related thereto including purified proteins, specific antibodies, and nucleic acids encoding this molecule are provided. Methods of using said reagents and diagnostic kits are also provided.

2 Claims, 26 Drawing Sheets

OTHER PUBLICATIONS

Watanabe, N., et al., "Human TSLP promotes CD40 ligand-induced IL-12 production by myeloid dendritic cells but maintains their Th2 priming potential," Blood, vol. 105(12) pp. 4749-4751 (2005).

Watanabe, N., et al., "Human thymic stromal lymphopoietin promotes dendritic cell-mediated CD4+T cell homeostatic expansion," Nature Immunology, vol. 5(4) pp. 426-434 (2005).

Zhou, B., et al., "Thymic stromal lymphopoietin as a key initiator of allergic airway inflammation in mice," Nature Immunology, vol. 6(10) pp. 1047-1053 (2005).

Ziegler, S., et al. "Thymic stromal lymphopoietin in normal and pathogenic T cell development and function," Nature Immunology, vol. 7(7), pp. 709-714 (2006).

Valenzona et al., "Exogenous Interleukin 7 as a Proliferative Stimulant of Early Precursor B Cells in Mouse Bone Marrow: Efficacy of IL-7 Injection, IL-7 Infusion and IL-7-Anti-IL-7 Antibody Complexes," Cytokine, vol. 10, No. 6, pp. 404-412 (Jun. 1998).

Miyaji, et al., "A Comparison of Proliferative Response to IL-7 and Expression of IL-7 Receptors in Intermediate TCR Cells of the Liver, Spleen, and Thymus," Cellular Immunology vol. 169, Article 0106, pp. 159-1.65 (1996).

Pearson, et al., "Effective Protein Sequence Comparison," Methods in Enzymology, vol. 266, pp. 227-258 (1996).

Mott, et al., "Four-Helix Bundle Growth Factors and Their Receptors: Protein-Protein Interactions," Current Opinion in Structural Biology, vol. 5, No. 1, pp. 114-121 (1995).

Kroemer, et al., "Prediction of the Three-Dimensional Structure of Human Interleukin-7 by Homology Modeling," Protein Engineering, vol. 9, No. 6, pp. 493-498 (1996).

Winkler, et al., "Interleukin-3 and Interleukin-7 Are Alternative Growth Factors for the Same B-Cell Precursors in the Mouse," Blood, vol. 85, pp. 2045-2051 (1995).

Al-Shami, of al., "A Role for Thymic Stromal Lymphopoietin in CD4+ T Cell Development," The Journal of Experimental Medicine, vol. 200, No. 2, pp. 159-168 (2004).

Al-Shami, et al., "A Role for Thymic Stromal Lymphopoietin in CD4+ T Cell Development," The Journal of Experimental Medicine, vol. 200, No. 2, pp. 159-168 (2004).

Cosenza, et al., "Disulfide Bond Assignment in Human Interleukin-7 by Matrix-Assisted Laser Desorption/Ionization Mass Spectroscopy and Site-Directed Cysteine to Serine Mutational Analysis," The Journal of Biological Chemistry, vol. 272, No. 52, pp. 32995-33000 (1997).

Kruse, et al., "Two Distinct Functional Sites of Human Interleukin 4 Are Identified by Variants Impaired in Either Receptor Binding or Receptor Activation," The EMBO Journal, vol. 12, No. 13, pp. 5121-5129 (1993).

Levin, Steven D., et al., Journal of Immunology, "Thymic Stromal Lymphoprotein: A cytokine that promotes the development of IgM+ B cells in Vitro and Signals via a novel mechanism," (Jan. 1999), pp. 677-683, vol. 182.

Mahairas, G.G., et al., GenBank, Accession No. AQ781833, (Aug. 2, 1999), Definition: "HS_3148_A2_C03_T7C CIT Approved Human Genomic Sperm Library D Homo sapiens genomic clone Plate=3148 Col=6 Row=E, genomic survey sequence."

Maeurer, Markus J., et al., The Cytokine Handbook, 3rd ed., "Interleukin-7," (1998), Ch. 9:229-269. Thomson, ed.(Academic Press, Inc., San Diego, California).

Marra, M., et al., GenBank, Accession No. AA717930, (Dec. 29, 1997), Definition: "vt09f05r1 Barstead mouse myotubes MPLRB5 Mus musculus cDNA clone IMAGE:1162593 5', mRNA sequence."

Marra, M., et al., GenBank, Accession No. AI591430, (Apr. 21, 1999), Definition: "vt09f05.r1 Barstead mouse myotubes MPLRB5 Mus musculus cDNA clone IMAGE:1162593 5', mRNA sequence."

NCI-CGAP. GenBank, Accession No. AA889581, (Jan. 4, 1999), Definition: "ak25a11.s1 Soares_testis_NHT Homo sapiens cDNA clone IMAGE:14072603', mRNA sequence."

Pending Claims for U.S. Appl. No. 09/963,347 (published as US 2003/0099947 A1); Bazan, et al., "*Mammalian Cytokines; Related Reagents and Methods*" (1 page), 2003.

International Search Report for application No. PCT/US99/20871 (6 pages), 1999.

Osborn, et al., "Overexpression of Murine TSLP Impairs Lymphopoiesis and Myelopoiesis," Blood, vol. 103, No. 3, pp. 843-851 (2004).

Quentmeier, et al., "Cloning of Human Thymic Stromal Lymphopoietin (TSLP) and Signaling Mechanisms Leading to Proliferation," Leukemia, vol. 15, No. 8, pp. 1286-1292 (2001).

Friend, Sherree Lee, et al., Experimental Hematology, "A thymic stromal cell line supports in vitro development of surface IgM+cells and produces a novel growth factor affecting B and T lineage cells" (1994), pp. 321-328, vol. 3.

Armitage et al., "Regulation of Human T Cell Proliferation by Il-7", The Journal of Immunology, vol. 144, No. 3, pp. 938-941 (1990).

Astrakhan et al., "Local increase in thymic stromal lymphopoietin induces systemic alterations in B cell development", Nature Immunlogy, vol. 8, No. 5, pp. 522-531 (2007).

Comeau et al., "The influence of TSLP on the allergic response", Mucosal Immunolgoy, vol. 3, No. 2, pp. 138-147 (2010).

Cosenza et al., "Comparative model building of interleukin-7 using interleukin-4 as a template: A structural hypothesis that displays atypical suface chemistry in helix D important for receptor activation", Protein Science, vol. 9, pp. 916-926 (2000).

Gilliet et al., "Human Dendritic Cells Activiated by TSLP and CD40L Induce Proallergic Cytotoxic T Cells", J, Exp. Med., vol. 197, No. 8, pp. 1059-1063 (2003).

He et al., "Thymic stromal lymphopoietin", Annals of the New York Academy of Sciences, vol. 1183, pp. 13-24 (2010).

Leonard, W., "Cytokines and Immunodeficiency Diseases", Nature, vol. 1, pp. 200-208 (2001).

Paul, W., Fundamental Immunology, 4th Edition, Lippincott-Raven Publishers, pp. 742-744 (1999).

McElroy et al., "Structural and Biophysical Studies of the Human Il-7/II Rα Complex", Structure, vol. 17, pp. 54-65 (2009).

Rochman and Leonard, "The Role of Thymic Stromal Lymphopoietin in CD8+T Cell Homeostasis", The Journal of Immunology, vol. 181, pp. 7699-7705 (2008).

Rochman et al., "New insight into the regulation of T cells by $\gamma_c$ family cytokines", Nature, vol. 9, pp. 480-490 (2009).

Scheeren et al., "Thymic stromal lymphopoietin induces early human B-cell proliferation and differentiation", Eur. J. Immunol., vol. 40, pp. 1-11 (2010).

vanderSpek et al., "Structure Function Analysis of Interleukin 7: Requirement for an aromatic rings at position 143 of Helix D", Cytokine, vol. 17, No. 5, pp. 227-233 (2002).

Wickham et al., "Crystallization and preliminary X-ray diffraction of human interleukin-7 bound to unglycosylated and glycosylated forms of its α-receptor", Acta. Cryst., Fol. F63, pp. 865-869 (2007).

Akamatsu, T., Human TSLP directly enhances expansion of CK8+ cells, Clinical and Experimental Immunology, vol. 154, pp. 98-106 (2008).

Anasetti, C., "Treatment of Acute Graft-Versus-Host Disease With Humanized Anti-Tac: An Antibody That Binds to the Interleukin-2 Receptor", Blood, vol. 84, No. 4, pp. 1320-1327 (1994).

Grabstein, K., et al.,"Cloning of a T Cell Growth Factor That Interacts with the β Chain of the Interleukin-2 Receptor", Science, vol. 264, pp. 965-968 (1994).

Guex-Crosier, et al., "Humanized Antibodies Against the α-Chain of the IL-2 Receptor and Against the β-Chain Shared by the IL-2 and IL-15 Receptors in a Monkey Uveitis Model of Autoimmune Diseases", The Journal of Immunology, vol. 158, pp. 452-458 (1997).

Lu, et al., "TSLP and IL-7 use two different mechanisms to regulate human CD4+ T cell homeostasis", The Journal of Experimental Medicine, vol. 206, No. 10, pp. 2111-2119 (2009).

Rochman et al., "Thymic stromal lymphopoietin: a new cytokine in asthma" Curr. Opin. Pharmacol., Vvol. 8, No. 3, pp. 249-254 (2008).

Waldmann, T.A., "Lymphokine receptors: A target for immunotherapy of lymphomas", Annals of Oncology, vol. 5, Suppl. 1, S13-S17 (1994).

Yoshizaki, K., et al., "Therapy of rheumatoid arthritis by blocking IL-6 signal transduction with a humanized anti-IL-6 receptor antibody", Springer Semin Immunopathol, vol. 20, pp. 247-259 (1998).

Notice of Opposition to EP Patent No. 1129190, dated Feb. 15, 2008.

Notice of Opposition to EP Patent No. 1129190, dated Feb. 15, 2008.

Proprietor's Observations in Response to Notices of Oppositions, dated Nov. 6, 2008.

Further Observations of Opponent to EP No. 1129190, dated Aug. 19, 2009.

Summons to Attend Oral Proceedings and Preliminary Opinion of the Opposition Division of the European Patent Office, dated Nov. 16, 2009.

Proprietor's Observations under Rule 116 EPC Prior to Oral Proceedings on Sep. 14, 2010, dated Jul. 14, 2010.

Abbas et al., "Lymphocyte Development and Heterogeneity", *Cellular and Molecular Immunology*, W. B. Saunders Company, Philadelphia, PA, 1991.

Notice of Opposition to EP Patent No. 1129190 including exhibits D2-D7 thereto, dated Feb. 12, 2008.

Proprietor's observations in response to notices of oppositions, dated Nov. 6, 2008 and exhibits C44 and C45 thereto.

Reference C3 to Proprietor's Observations in Response to Notices of Oppositions, dated Nov. 6, 2008; created Apr. 6, 1998, updated Apr. 6, 1998 and Jan. 6, 1999: Sequence Version Archive for AA889581.

```
                        *  *                          * * *                 * *         *  *                   *
IL-7human    MFH........ .VSFRYIFGL PPLIIVLLPV ASSDCDIEGK DGKQYESVLM
IL-7sheep    MFH........ .VSFRYIFGI PPLILVLLPV ASSDCDFSGK DGGAYQNVLM
IL-7bovin    MFH........ .VSFRYIFGI PPLILVLLPV ASSDCDISGK DGGAYQNVLM
IL-7mouse    MFH........ .VSFRYIFGI PPLIIVLLPV TSSECHIKDK EGKAYESVLM
IL-7rat      MFH........ .VSFRYIFGI PPLIIVLLPV TSSDCHIKDK DGKAFGSVLM
ILB50human   MEPFALLYVL SVSFRKIFIL QLVGLVLT.Y DFTNCDFE..K IKAAYLSTIS
                                                            ─────────
                                                             helix A

*                  *        *                  *
IL-7human    VSIDQLLDSM KEIGSNCLNN EPNFFKRHIC DANKEGMFLF RAARKLRQFL
IL-7sheep    VSIDDL.DNM INFDSNCLNN EPNFFKKHSC DDNKEASFLN RAARKLKQFL
IL-7bovin    VNIDDL.DNM INFDSNCLNN EPNFFKKHSC DDNKEASFLN RASRKLRQFL
IL-7mouse    ISIDEL.DKM TGTDSNCPNN EPNFFRKHVC DDTKEAAFLN RAARKLRQFL
IL-7rat      ISINQL.DKM TGTDSDCPNN EPNFFKKHLC DDTKEAAFLN RAARKLRQFL
ILB50human   KDLITY...M SGTKSTEFNN TVSCSNRPHC LTEIQSLTEN PTAGCASLAK
             ──────                  ^^^^                 ──────────
             strand 1                         helix B
```

FIG. 1A

```
IL-7human    KMNSTGDFDL HLLKVSEGTT ILLNCTGQVK GRKPAALGEA QPTKSLEENK
IL-7sheep    KMNISDDFKL HLSTVSQGTL TLLNCTSKGK GRKPPSLGEA QPTKNLEENK
IL-7bovin    KMNISDDFKL HLSTVSQGTL TLLNCTSKGK GRKPPSLSEA QPTKNLEENK
IL-7mouse    KMNISEEFNV HLLTVSQGTQ TLVNCTSK.. .......... ......EEK
IL-7rat      KMNISEEFND HLLRVSDGTQ TLVNCTSK.. .......... ......EEK
iLB50human   EMFAMKTKAA LAIWCPGYSE TQINATQA.. .......... .......MK
                                  ----------
                                    helix C IL-7human    SLKEQKKLND LCFLKRLLQE IKTCWNKILM GTKEH
IL-7sheep    SLKEQRKQND LCFLKILLQK IKTCWNKILR GITEH
IL-7bovin    SSKEQKKQND LCFLKILLQK IKTCWNKILR GIKEH
IL-7mouse    NVKEQKK.ND ACFLKRLLRE IKTCWNKILK GSI..
IL-7rat      TIKEQKK.ND PCFLKRLLRE IKTCWNKILK GSI..
iLB50human   KRRKRKVTTN KCLEQVSQLQ GLWRRFNRPL LKQQ.
                       ---------- ---------
             ^^^         helix D
             strand 2
```

FIG. 1B

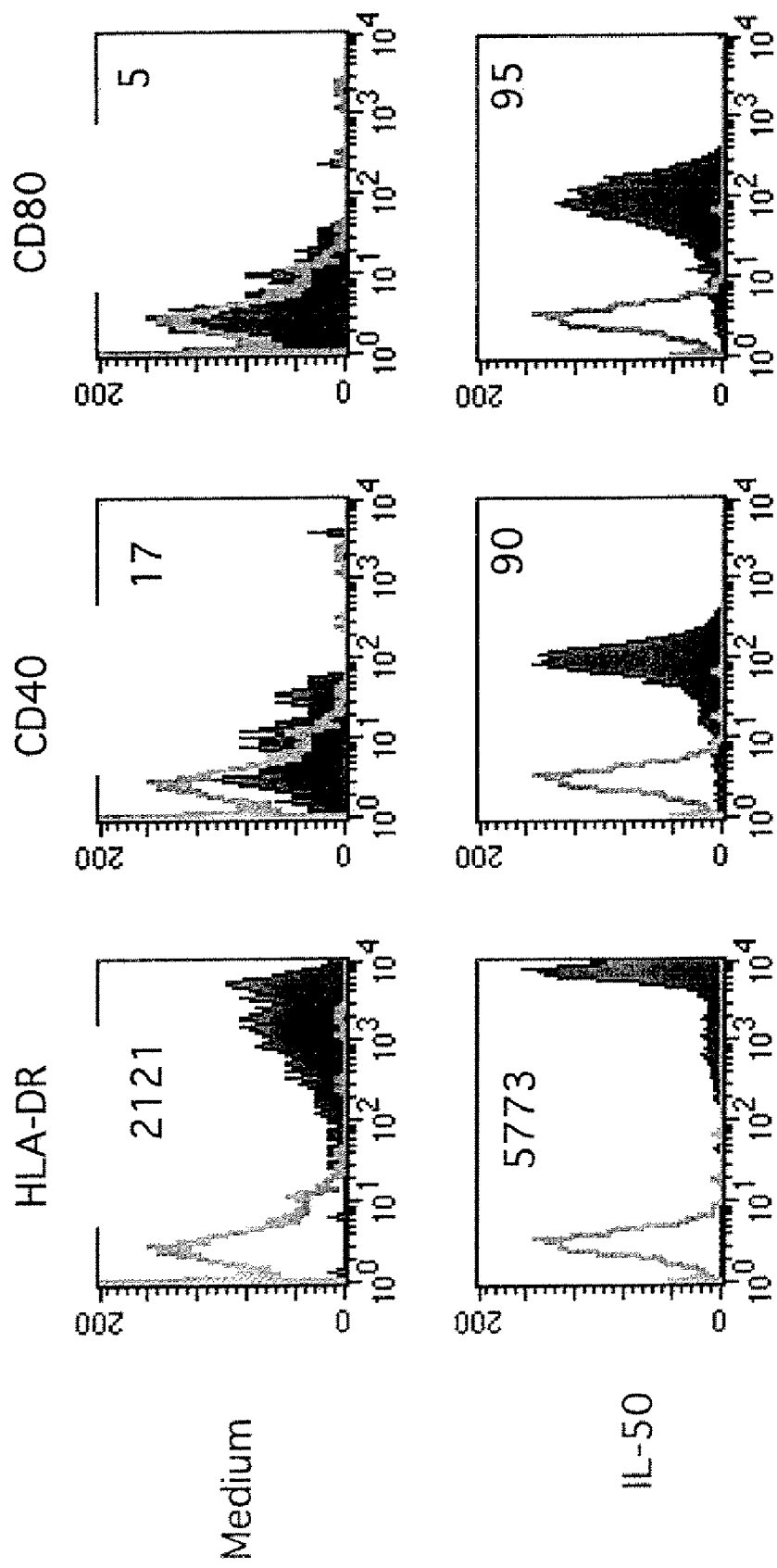

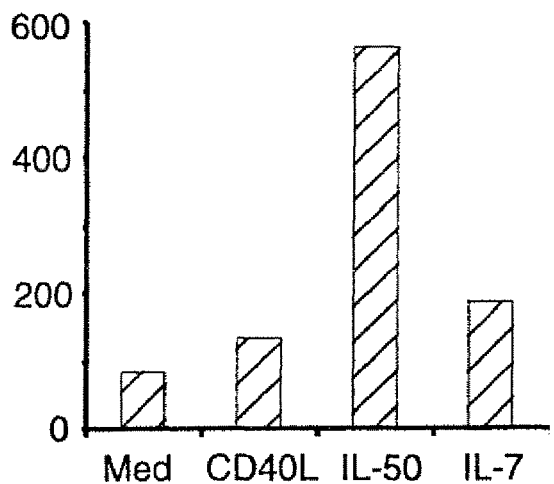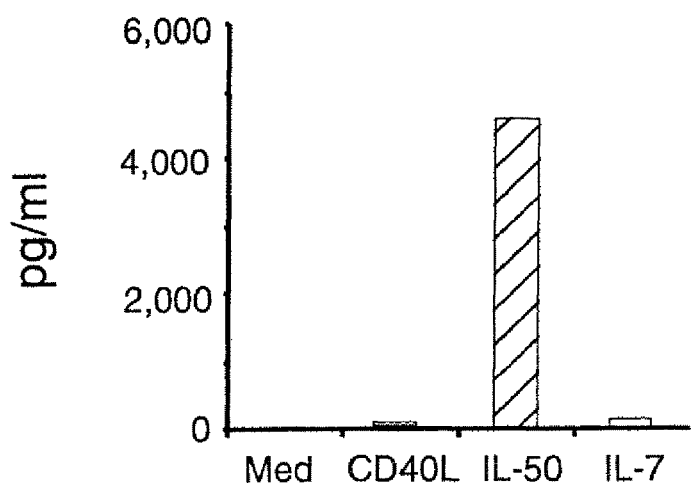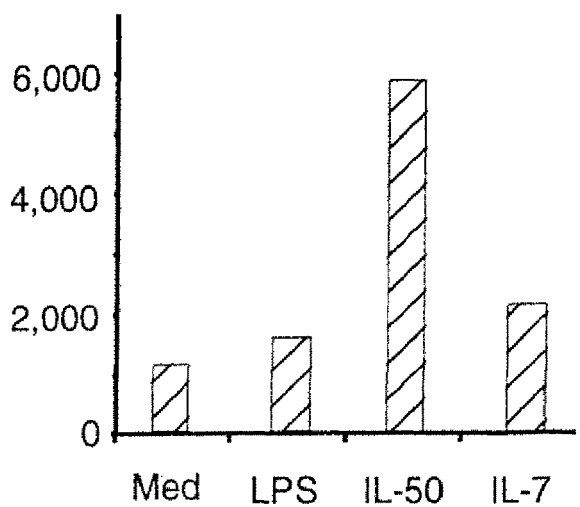
FIG. 9B

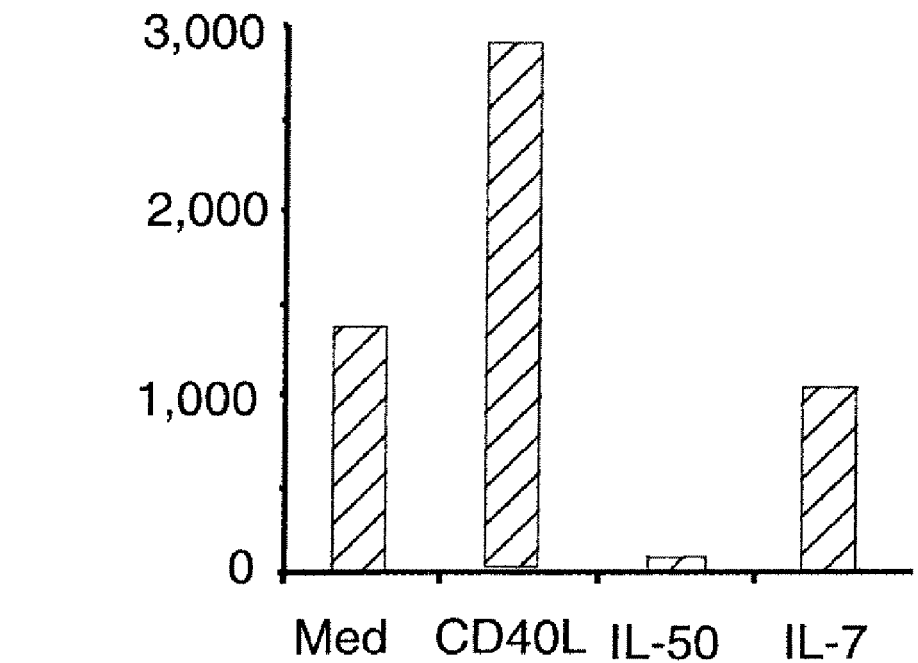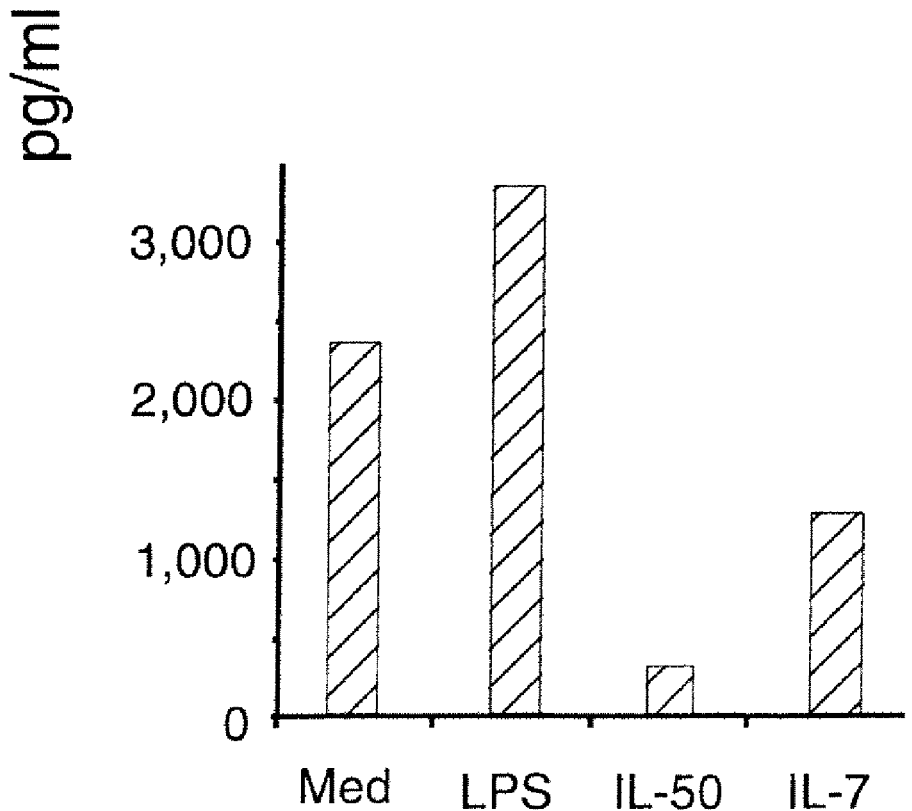
FIG. 9D

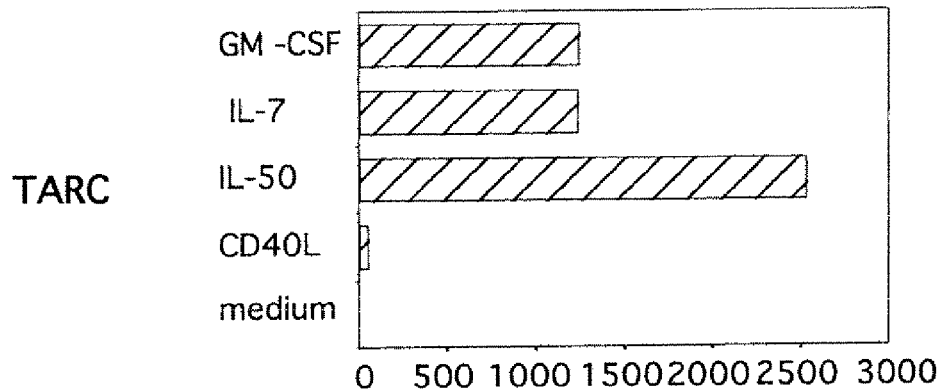
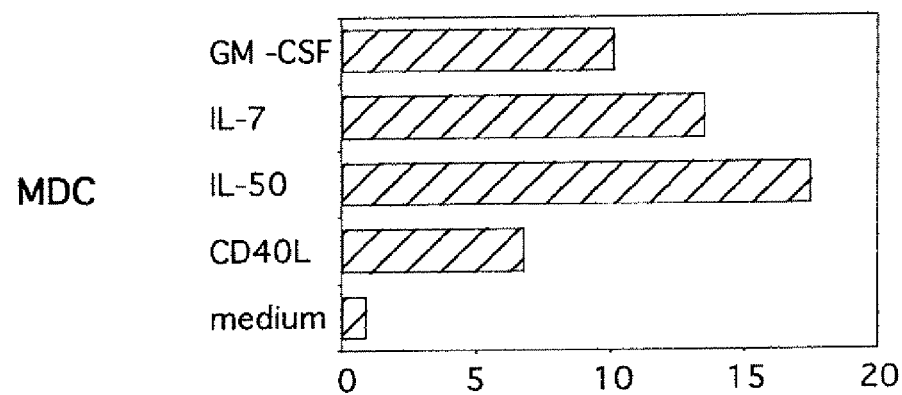
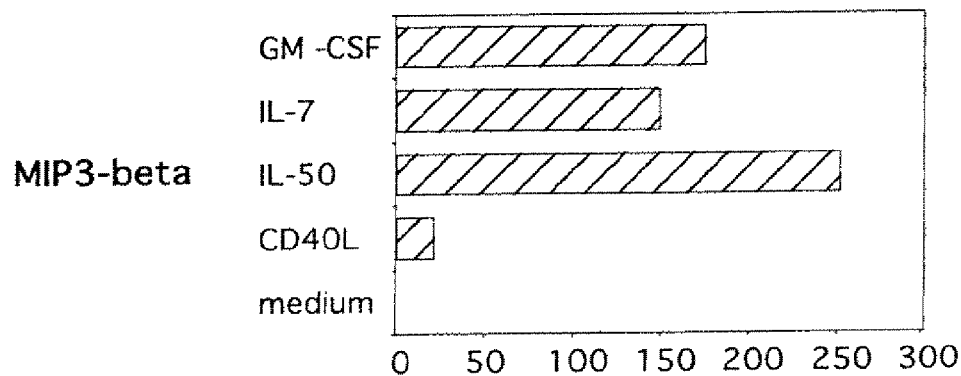
FIG. 12B

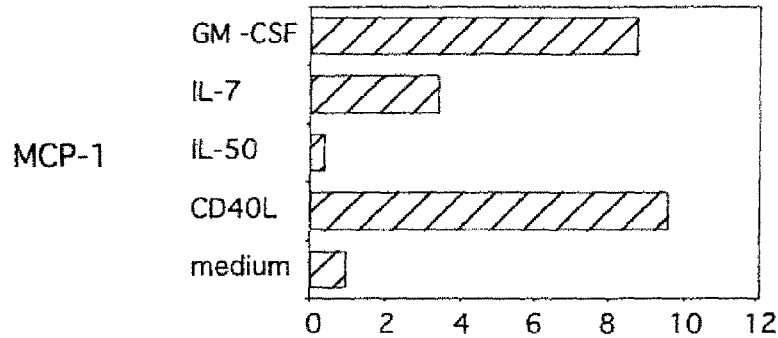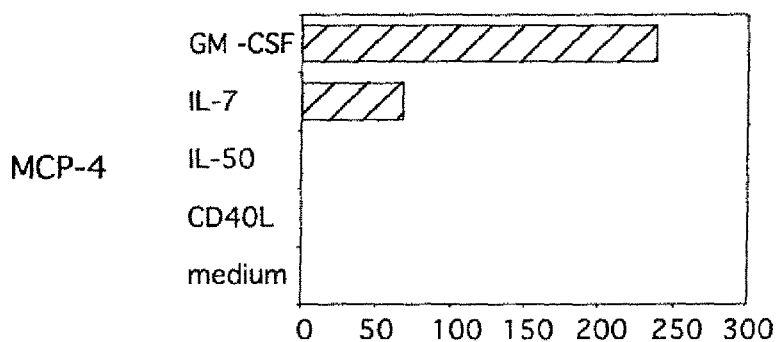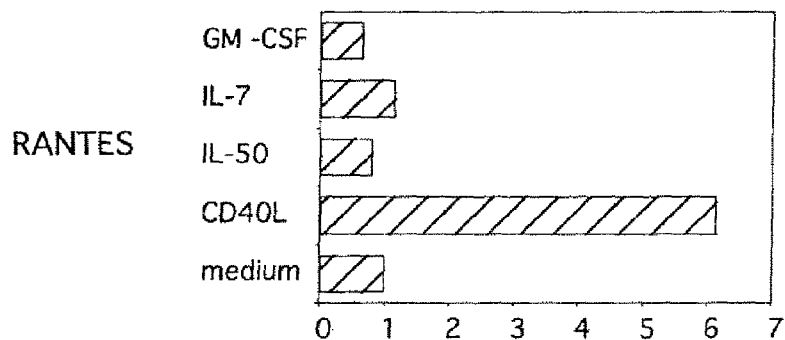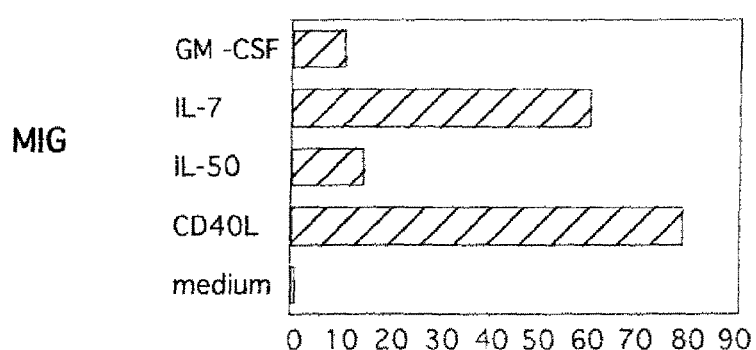
FIG. 12C

IL-B50 POLYPEPTIDE

This filing is a continuation of U.S. patent application Ser. No. 09/963,347, filed Sep. 25, 2001, now abandoned, which is a continuation-in-Part of U.S. patent application Ser. No. 09/399,492, filed Sep. 20, 1999, abandoned, and claims benefit of U.S. Provisional Patent Applications 60/131,298, filed Apr. 27, 1999, and 60/101,318, filed Sep. 21, 1998, all of which are incorporated herein by reference.

FIELD OF THE INVENTION

The present invention pertains to compositions related to proteins which function in controlling biology and physiology of mammalian cells, e.g., cells of a mammalian immune system. In particular, it provides purified genes, proteins, antibodies, and related reagents useful, e.g., to regulate activation, development, differentiation, and function of various cell types, including hematopoietic cells.

BACKGROUND OF THE INVENTION

Recombinant DNA technology refers generally to the technique of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

For some time, it has been known that the mammalian immune response is based on a series of complex cellular interactions, called the "immune network". Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as lymphokines, cytokines, or monokines, play a critical role in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders. Some of these factors are hematopoietic growth and/or differentiation factors, e.g., stem cell factor (SCF) and IL-7. See, e.g., Mire-Sluis and Thorpe (1998) *Cytokines* Academic Press, San Diego; Thomson (ed. 1998) *The Cytokine Handbook* (3d ed.) Academic Press, San Diego; Metcalf and Nicola (1995) *The Hematopoietic Colony Stimulating Factors* Cambridge University Press; and Aggarwal and Gutterman (1991) *Human Cytokines* Blackwell.

Lymphokines apparently mediate cellular activities in a variety of ways. They have been shown to support the proliferation, growth, and differentiation of pluripotential hematopoietic stem cells into vast numbers of progenitors comprising diverse cellular lineages making up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

Another important cell lineage is the mast cell (which has not been positively identified in all mammalian species), which is a granule-containing connective tissue cell located proximal to capillaries throughout the body. These cells are found in especially high concentrations in the lungs, skin, and gastrointestinal and genitourinary tracts. Mast cells play a central role in allergy-related disorders, particularly anaphylaxis as follows: when selected antigens crosslink one class of immunoglobulins bound to receptors on the mast cell surface, the mast cell degranulates and releases mediators, e.g., histamine, serotonin, heparin, and prostaglandins, which cause allergic reactions, e.g., anaphylaxis.

Research to better understand and treat various immune disorders has been hampered by the general inability to maintain cells of the immune system in vitro. Immunologists have discovered that culturing these cells can be accomplished through the use of T-cell and other cell supernatants, which contain various growth factors, including many of the lymphokines.

From the foregoing, it is evident that the discovery and development of new lymphokines, e.g., related to IL-7, could contribute to new therapies for a wide range of degenerative or abnormal conditions which directly or indirectly involve the immune system and/or hematopoietic cells. In particular, the discovery and development of lymphokines which enhance or potentiate the beneficial activities of known lymphokines would be highly advantageous. The present invention provides new interleukin compositions and related compounds, and methods for their use.

BRIEF DESCRIPTION OF THE DRAWINGS

FIGS. 1A and 1B show a comparison of various IL-7 embodiments compared to IL-B50. The sequence of IL-B50 corresponds to SEQ ID NO:4. The IL-7 from sheep is SEQ ID NO: 5; from bovine is SEQ ID NO: 6; from human is SEQ ID NO: 7; from mouse is SEQ ID NO: 8; and from rat is SEQ ID NO: 9. See also GenBank. C is in bold and predicted glycosylated N is underlined. * represents sequence identity with human IL-7.

FIGS. 6A-6C show the surface phenotype of DC after treatment with medium alone, IL-B50, CD40-ligand (CD40L), IL-7 and LPS. IL-B50 is more potent than CD40-ligand and IL-7 in upregulating costimulatory molecules CD40 and CD80.

FIGS. 9A-9E show the production of various cytokines (expressed as pg/ml) by naïve CD4 T cells cocultured with DC matured in medium alone, IL-B50, CD40-ligand (CD40L), IL-7 and LPS. FIG. 9A shows the effect on the production of IL-4; FIG. 9B shows the effect on the production of IL-13; FIG. 9C shows the effect on the production of IFN-γ, FIG. 9D shows the effect on the production of IL-10 and FIG. 9E shows the effect on the production of TNF-α.

FIGS. 12A-12C show the results of a comparison of IL-B50 with GM-CSF, IL-7, CD40-ligand (CD40L) and medium alone as a control, to stimulate human DCs to produce mRNA for various cytokines and chemokines. FIG. 12A shows effects on IL-1α, IL-1β, IL-6, IL-12p40 and TNF-α. FIG. 12B shows effects on TARC, MDC and MIP3-β. FIG. 12C shows effects on MCP-1, MCP-4, Rantes and MIG.

SUMMARY OF THE INVENTION

Figure 2A:
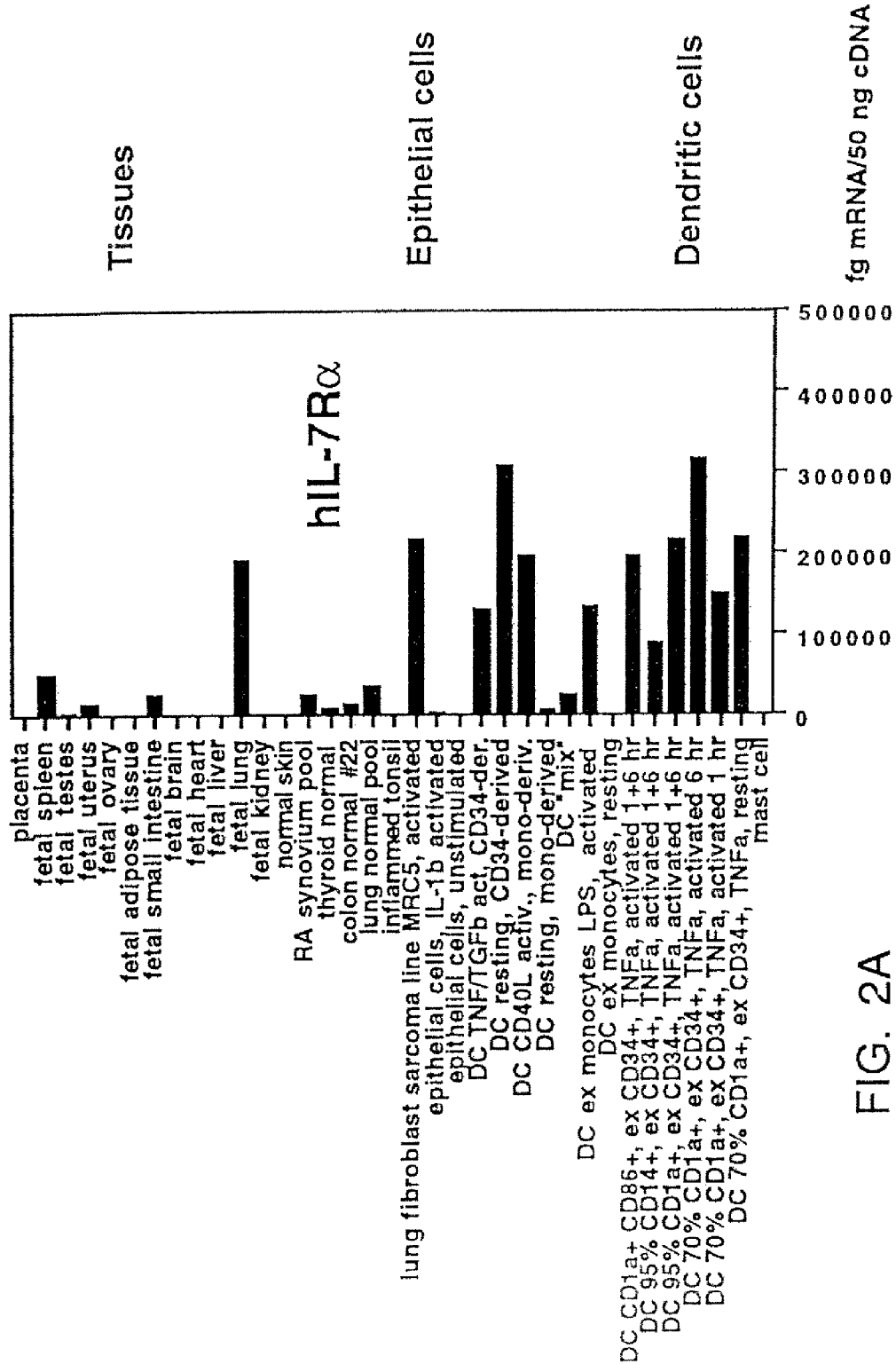
FIGS. 2A-2E show expression levels of hIL-7Rα (FIGS. 2A-2B), Rδ2 (hTSLPR, FIGS. 2C-2D), and IL-B50 in various tissues and cell types. Expression levels were normalized and expressed as femtograms mRNA per 50 ng total cDNA.
Figure 2B:
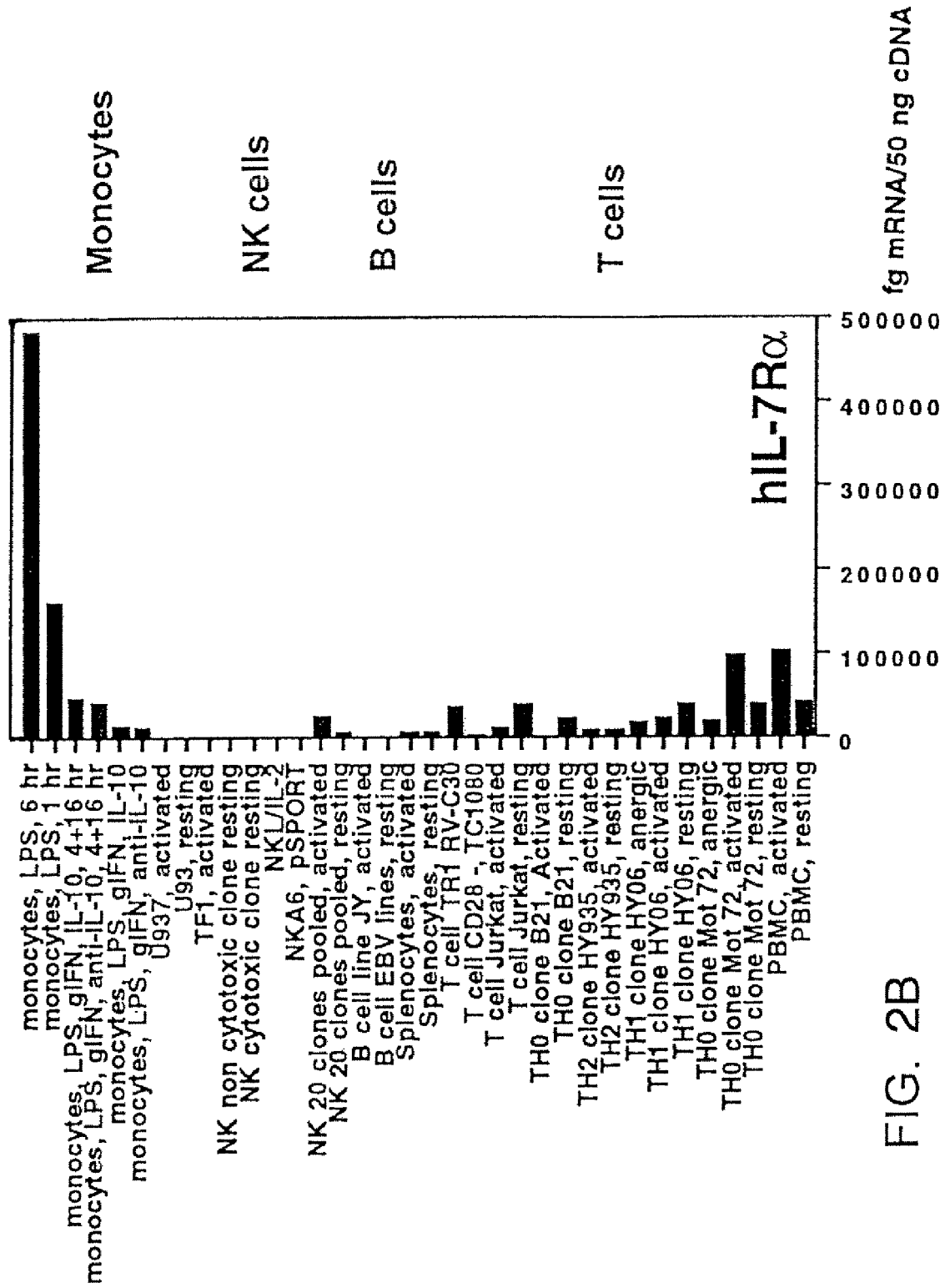
Figure 2C:
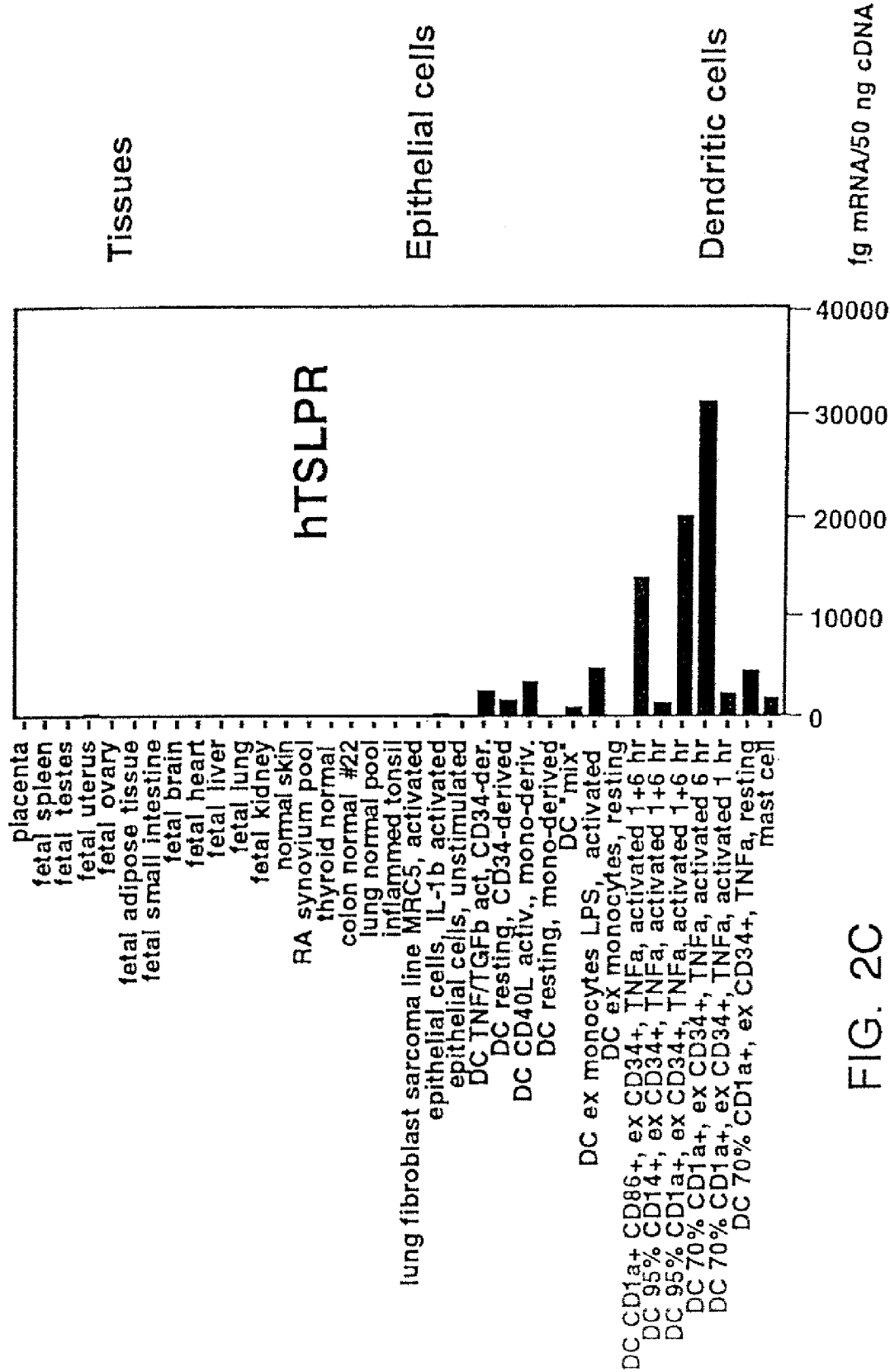
Figure 2D:
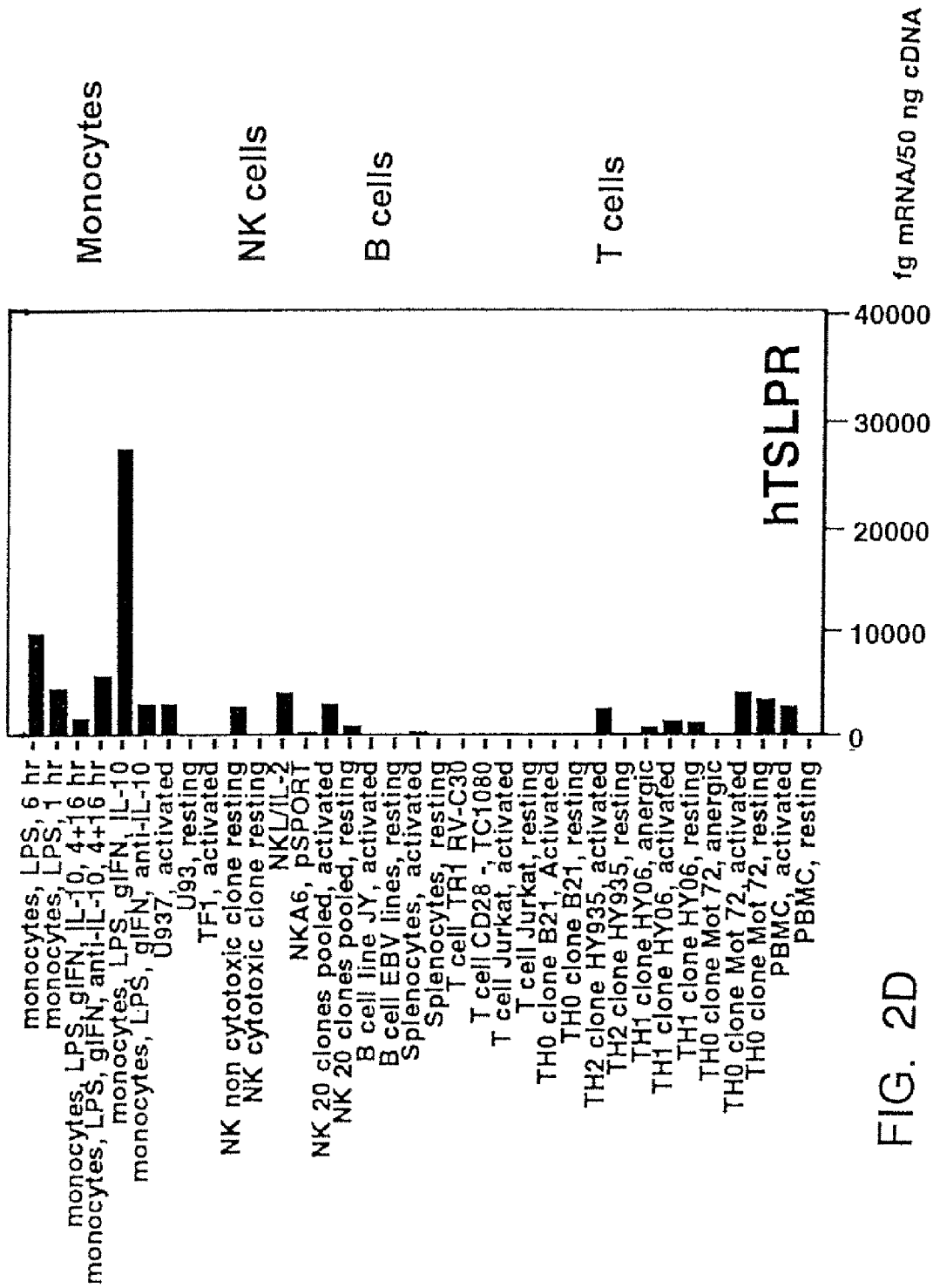

The present invention is directed to mammalian, e.g., rodent, canine, feline, primate, interleukin-B50 (IL-B50) and its biological activities. It includes nucleic acids coding for polypeptides themselves and methods for their production and use. The nucleic acids of the invention are characterized, in part, by their homology to cloned complementary DNA (cDNA) sequences enclosed herein, and/or by functional assays for growth factor- or cytokine-like activities, e.g., IL-7 (see Maeurer, et al. (1998) in Thomson (ed.) *The Cytokine Handbook* 3d ed., Academic Press, San Diego; Namien and Mire-Sluis (1998) in Mire-Sluis and Thorpe (eds.) *Cytokines* Academic Press, San Diego; and Edington and Lotze (1994) in Thomson (ed.) *The Cytokine Handbook* 2d ed., Academic Press, San Diego), applied to the polypeptides, which are typically encoded by these nucleic acids. Methods for modulating or intervening in the control of a growth factor dependent physiology or an immune response are provided.

The present invention is based, in part, upon the discovery of a new cytokine sequence exhibiting significant sequence and structural similarity to IL-7. In particular, it provides primate, e.g., human, sequences. Functional equivalents exhibiting significant sequence homology will be available from other mammalian, e.g., cow, horse, and rat, mouse, and non-mammalian species.

In various protein embodiments, the invention provides: a substantially pure or recombinant IL-B50 polypeptide exhibiting identity over a length of at least about 12 amino acids to SEQ ID NO: 2 or 4; a natural sequence IL-B50 of SEQ ID NO: 2 or 4; and a fusion protein comprising IL-B50 sequence. In certain embodiments, the segment of identity is at least about 14, 17, or 19 amino acids. In other embodiments, the IL-B50: comprises a mature sequence comprising the sequence SEQ ID NO:2 or 4; or exhibits a post-translational modification pattern distinct from natural IL-B50; or the polypeptide: is from a warm blooded animal selected from a mammal, including a primate; comprises at least one polypeptide segment of SEQ ID NO: 2 or 4; exhibits a plurality of fragments; is a natural allelic variant of IL-B50; has a length at least about 30 amino acids; exhibits at least two non-overlapping epitopes which are specific for a primate IL-B50; exhibits sequence identity over a length of at least about 20 amino acids to primate IL-B50; is glycosylated; has a molecular weight of at least 10 kD with natural glycosylation; is a synthetic polypeptide; is attached to a solid substrate; is conjugated to another chemical moiety; is a 5-fold or less substitution from natural sequence; or is a deletion or insertion variant from a natural sequence. Preferred embodiments include a composition comprising: a sterile IL-B50 polypeptide; or the IL-B50 polypeptide and a carrier, wherein the carrier is: an aqueous compound, including water, saline, and/or buffer; and/or formulated for oral, rectal, nasal, topical, or parenteral administration. In fusion protein embodiments, the protein can have: mature polypeptide sequence of SEQ ID NO:2 or 4; a detection or purification tag, including a FLAG, His6, or Ig sequence; and/or sequence of another cytokine or chemokine, including an IL-7.

Kit embodiments include those with an IL-B50 polypeptide, and: a compartment comprising the polypeptide; and/or instructions for use or disposal of reagents in the kit.

In binding compound embodiments, the compound may have an antigen binding site from an antibody, which specifically binds to a natural IL-B50 polypeptide, wherein: the IL-B50 is a primate protein; the binding compound is an Fv, Fab, or Fab2 fragment; the binding compound is conjugated to another chemical moiety; or the antibody: is raised against a peptide sequence of a mature polypeptide portion of SEQ ID NO:2 or 4; is raised against a mature IL-B50; is raised to a purified primate IL-B50; is immunoselected; is a polyclonal antibody; binds to a denatured IL-B50; exhibits a Kd of at least 30 μM; is attached to a solid substrate, including a bead or plastic membrane; is in a sterile composition; or is detectably labeled, including a radioactive or fluorescent label. Kits containing binding compounds include those with: a compartment comprising the binding compound; and/or instructions for use or disposal of reagents in the kit. Often the kit is capable of making a qualitative or quantitative analysis. Preferred compositions will comprise: a sterile binding compound; or the binding compound and a carrier, wherein the carrier is: an aqueous compound, including water, saline, and/or buffer; and/or formulated for oral, rectal, nasal, topical, or parenteral administration.

Nucleic acid embodiments include an isolated or recombinant nucleic acid encoding an IL-B50 polypeptide or fusion protein, wherein: the IL-B50 is from a primate; and/or the nucleic acid: encodes an antigenic peptide sequence of SEQ ID NO: 2 or 4; encodes a plurality of antigenic peptide sequences of SEQ ID NO: 2 or 4; exhibits identity to a natural cDNA encoding the segment; is an expression vector; further comprises an origin of replication; is from a natural source; comprises a detectable label; comprises synthetic nucleotide sequence; is less than 6 kb, preferably less than 3 kb; is from a primate, including a human; comprises a natural full length coding sequence; is a hybridization probe for a gene encoding the IL-B50; or is a PCR primer, PCR product, or mutagenesis primer. The invention also provides a cell, tissue, or organ comprising such a recombinant nucleic acid, and preferably the cell will be: a prokaryotic cell; a eukaryotic cell; a bacterial cell; a yeast cell; an insect cell; a mammalian cell; a mouse cell; a primate cell; or a human cell.

Kit embodiments include those with such nucleic acids, and: a compartment comprising the nucleic acid; a compartment further comprising the IL-B50 protein or polypeptide; and/or instructions for use or disposal of reagents in the kit. Typically, the kit is capable of making a qualitative or quantitative analysis.

In certain embodiments, the nucleic acid: hybridizes under wash conditions of 30° C. and less than 2M salt, or of 45° C. and/or 500 mM salt, or 55° C. and/or 150 mM salt, to SEQ ID NO: 1 or 3; or exhibits identity over a stretch of at least about 30, 55, or 75 nucleotides, to a primate IL-B50.

The invention embraces a method of modulating physiology or development of a cell or tissue culture cells comprising contacting the cell with an agonist or antagonist of a primate IL-B50. The method may be where: the contacting is in combination with an agonist or antagonist of IL-7; or the contacting is with an antagonist, including a binding composition comprising an antibody binding site which specifically binds an IL-B50.

DETAILED DESCRIPTION OF THE PREFERRED EMBODIMENTS

All references cited herein are incorporated herein by reference to the same extent as if each individual publication or patent application was specifically and individually indicated to be incorporated by reference.

I. General

The present invention provides amino acid sequences and DNA sequences encoding various mammalian proteins which are cytokines, e.g., which are secreted molecules which can mediate a signal between immune or other cells. See, e.g., Paul (1997) *Fundamental Immunology* (3d ed.) Raven Press, N.Y. The full length cytokines, and fragments, or antagonists will be useful in physiological modulation of cells expressing a receptor. It is likely that IL-B50 has either stimulatory or inhibitory effects on hematopoietic cells, including, e.g., lymphoid cells, such as T-cells, B-cells, natural killer (NK) cells, macrophages, dendritic cells, hematopoietic progenitors, etc. The proteins will also be useful as antigens, e.g., immunogens, for raising antibodies to various epitopes on the protein, both linear and conformational epitopes.

A cDNA encoding IL-B50 was identified from a human cDNA sequence. See, e.g., Accession number AA889581. The molecule was designated huIL-B50.

The human gene will encode a small soluble cytokine-like protein, of about 175 amino acids. The signal sequence probably is about 33 residues, and would run from the met to about thr. See SEQ ID. NO: 1 and 2; supplementary sequence provides SEQ ID NO: 3 and 4. IL-B50 exhibits structural motifs characteristic of a member of the short chain cytokines. Compare, e.g., IL-B50 and IL-7, sequences available from GenBank. See also FIGS. 1A and 1B.

The structural homology of IL-B50 to related cytokine proteins suggests related function of this molecule. IL-B50 is a short chain cytokine exhibiting sequence similarity to IL-7.

Many aspects of the biology of IL-7 is well recognized. See, e.g., Bauer, et al. (1998) "Modulated expression of the epidermal growth factor-like homeotic protein dlk influences stromal-cell-pre-B-cell interactions, stromal cell adipogenesis, and pre-B-cell interleukin-7 requirements" *Mol. Cell. Biol.* 18:5247-5255; Maeurer, et al. (1998) "Interleukin-7 (IL-7) knockout mice. Implications for lymphopoiesis and organ-specific immunity" *Int. Rev. Immunol.* 16309-322; Mertsching, et al. (1998) "Interleukin-7, a non-redundant potent cytokine whose over-expression massively perturbs B-lymphopoiesis" *Int. Rev. Immunol.* 16:285-308; Maini, et al. (1997) "New developments in the use of cytokines for cancer therapy" *Anticancer Res.* 17:3803-3808; Murray (1996) "Physiologic roles of interleukin-2, interleukin-4, and interleukin-7" *Curr. Opin. Hematol.* 3:230-234; Takatsu (1997) "Cytokines involved in B-cell differentiation and their sites of action" *Proc. Soc. Exp. Biol. Med.* 215:121-133; Candeias, et al. (1997) "IL-7 receptor and VDJ recombination: trophic versus mechanistic actions" *Immunity* 6:501-508; Lachman, et al. (1996) "Cytokine-containing liposomes as vaccine adjuvants" *Eur. Cytokine Netw.* 7:693-698; Takashima, et al. (1996) "Cytokine-mediated communication by keratinocytes and Langerhans cells with dendritic epidermal T cells" *Sernin. Immunol.* 8:333-339; and Johnston, et al. (1996) "Signaling by IL-2 and related cytokines: JAKs, STATs, and relationship to immunodeficiency" *J. Leukoc. Biol.* 60:441-452. The biology of the IL-B50 is likely to be similar. See, e.g., Friend, et al. (1994) *Exp. Hematol.* 22:321-328.

IL-B50 agonists, or antagonists, may also act as functional or receptor antagonists, e.g., which block IL-7 binding to its respective receptors, or mediating the opposite actions. Thus, IL-B50, or its antagonists, may be useful in the treatment of abnormal medical conditions, including immune disorders, e.g., T cell immune deficiencies, chronic inflammation, or tissue rejection, or in cardiovascular or neurophysiological conditions. Compositions combining the IL-B50 and IL-7 related reagents will often be used.

The natural antigens are capable of mediating various biochemical responses which lead to biological or physiological responses in target cells. The preferred embodiment characterized herein is from human, but other primate, or other species counterparts exist in nature. Additional sequences for proteins in other mammalian species, e.g., primates, canines, felines, and rodents, should also be available. See below. The descriptions below are directed, for exemplary purposes, to a human IL-B50, but are likewise applicable to related embodiments from other species.

II. Purified IL-B50

Primate, e.g., human, IL-B50 amino acid sequence, is shown as one embodiment within SEQ ID NO: 2 or 4. Other naturally occurring nucleic acids which encode the protein can be isolated by standard procedures using the provided sequence, e.g., PCR techniques, or by hybridization. These amino acid sequences, provided amino to carboxy, are important in providing sequence information for the cytokine allowing for distinguishing the protein antigen from other proteins and exemplifying numerous variants. Moreover, the peptide sequences allow preparation of peptides to generate antibodies to recognize such segments, and nucleotide sequences allow preparation of oligonucleotide probes, both of which are strategies for detection or isolation, e.g., cloning, of genes encoding such sequences.

As used herein, the term "human soluble IL-B50" shall encompass, when used in a protein context, a protein having amino acid sequence corresponding to a soluble polypeptide shown in SEQ ID NO: 2 or 4, or significant fragments thereof. Preferred embodiments comprise a plurality of distinct, e.g., nonoverlapping, segments of the specified length. Typically, the plurality will be at least two, more usually at least three, and preferably 5, 7, or even more. While the length minima are provided, longer lengths, of various sizes, may be appropriate, e.g., one of length 7, and two of length 12.

Binding components, e.g., antibodies, typically bind to an IL-B50 with high affinity, e.g., at least about 100 nM, usually better than about 30 nM, preferably better than about 10 nM, and more preferably at better than about 3 nM. Counterpart proteins will be found in mammalian species other than human, e.g., other primates, ungulates, or rodents. Non-mammalian species should also possess structurally or functionally related genes and proteins, e.g., birds or amphibians.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids, e.g., 35, 40, 45, 50, etc. Such fragments may have ends which begin and/or end at virtually all positions, e.g., beginning at residues 1, 2, 3, etc., and ending at, e.g., 150, 149, 148, etc., in all practical combinations. Particularly interesting peptides have ends corresponding to structural domain boundaries, e.g., helices A, B, C, and/or D.

The term "binding composition" refers to molecules that bind with specificity to IL-B50, e.g., in an antibody-antigen interaction. The specificity may be more or less inclusive, e.g., specific to a particular embodiment, or to groups of related embodiments, e.g., primate, rodent, etc. It also includes compounds, e.g., proteins, which specifically associate with IL-B50, including in a natural physiologically relevant protein-protein interaction, either covalent or non-covalent. The molecule may be a polymer, or chemical reagent. A functional analog may be a protein with structural modifications, or it may be a molecule which has a molecular shape which interacts with the appropriate binding determinants. The compounds may serve as agonists or antagonists of a receptor binding interaction, see, e.g., Goodman, et al. (eds.) *Goodman & Gilman's: The Pharmacological Bases of Therapeutics* (current ed.) Pergamon Press.

Substantially pure, e.g., in a protein context, typically means that the protein is free from other contaminating proteins, nucleic acids, or other biologicals derived from the original source organism. Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure. Carriers or excipients will often be added.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. For diagnostic purposes, the temperature will usually be about room temperature or warmer, but less than the denaturation temperature of components in the assay. For therapeutic purposes, the temperature will usually be body temperature, typically about 37° C. for humans and mice, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS (cholesteryl hemisuccinate) or CHAPS (3-[3-cholamidopropyl]dimethylammonio]-1-propane sulfonate), or a low enough concentration as to avoid significant disruption of structural or physiological properties of the protein. In other instances, a harsh detergent may be used to effect significant denaturation.

III. Physical Variants

This invention also encompasses proteins or peptides having substantial amino acid sequence identity with the amino acid sequence of the IL-B50 antigen. The variants include species, polymorphic, or allelic variants.

Amino acid sequence homology, or sequence identity, is determined by optimizing residue matches, if necessary, by introducing gaps as required. See also Needleham, et al. (1970) *J. Mol. Biol.* 48:443-453; Sankoff, et al. (1983) Chapter One in *Time Warps, String Edits, and Macromolecules: The Theory and Practice of Sequence Comparison*, Addison-Wesley, Reading, Mass.; and software packages from Intelli-Genetics, Mountain View, Calif.; and the University of Wisconsin Genetics Computer Group, Madison, Wis. Sequence identity changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. The conservation may apply to biological features, functional features, or structural features. Homologous amino acid sequences are typically intended to include natural polymorphic or allelic and interspecies variations of a protein sequence. Typical homologous proteins or peptides will have from 25-100% identity (if gaps can be introduced), to 50-100% identity (if conservative substitutions are included) with the amino acid sequence of the IL-B50. Identity measures will be at least about 35%, generally at least about 40%, often at least about 50%, typically at least about 60%, usually at least about 70%, preferably at least about 80%, and more preferably at least about 90%.

The isolated IL-B50 DNA can be readily modified by nucleotide substitutions, nucleotide deletions, nucleotide insertions, and inversions of short nucleotide stretches. These modifications result in novel DNA sequences which encode these antigens, their derivatives, or proteins having similar physiological, immunogenic, antigenic, or other functional activity. These modified sequences can be used to produce mutant antigens or to enhance expression. Enhanced expression may involve gene amplification, increased transcription, increased translation, and other mechanisms. "Mutant IL-B50" encompasses a polypeptide otherwise falling within the sequence identity definition of the IL-B50 as set forth above, but having an amino acid sequence which differs from that of IL-B50 as normally found in nature, whether by way of deletion, substitution, or insertion. This generally includes proteins having significant identity with a protein having sequence of SEQ ID NO: 2 or 4, and as sharing various biological activities, e.g., antigenic or immunogenic, with those sequences, and in preferred embodiments contain most of the natural full length disclosed sequences. Full length sequences will typically be preferred, though truncated versions will also be useful, likewise, genes or proteins found from natural sources are typically most desired. Similar concepts apply to different IL-B50 proteins, particularly those found in various warm blooded animals, e.g., mammals and birds. These descriptions are generally meant to encompass many IL-B50 proteins, not limited to the particular primate embodiments specifically discussed.

IL-B50 mutagenesis can also be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See, e.g., Sambrook, et al. (1989); Ausubel, et al. (1987 and Supplements); and Kunkel, et al. (1987) *Methods in Enzymol.* 154:367-382. Preferred embodiments include, e.g., 1-fold, 2-fold, 3-fold, 5-fold, 7-fold, etc., preferably conservative substitutions at the nucleotide or amino acid levels. Preferably the substitutions will be away from the conserved cysteines, and often will be in the regions away from the helical structural domains. Such variants may be useful to produce specific antibodies, and often will share many or all biological properties.

The present invention also provides recombinant proteins, e.g., heterologous fusion proteins using segments from these proteins. A heterologous fusion protein is a fusion of proteins or segments which are naturally not normally fused in the same manner. A similar concept applies to heterologous nucleic acid sequences.

In addition, new constructs may be made from combining similar functional domains from other proteins. For example, target-binding or other segments may be "swapped" between different new fusion polypeptides or fragments. See, e.g., Cunningham, et al. (1989) *Science* 243:1330-1336; and O'Dowd, et al. (1988) *J. Biol. Chem.* 263:15985-15992.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

Structural analysis can be applied to this gene, in comparison to the IL-7 family of cytokines. Alignment of the human IL-B50 sequences with other members of the IL-7 family should allow definition of structural features. In particular, β-sheet and α-helix residues can be determined using, e.g., RASMOL program, see Bazan, et al. (1996) *Nature* 379:591; Lodi, et al. (1994) *Science* 263:1762-1766; Sayle and Milner-White (1995) *TIBS* 20:374-376; and Gronenberg, et al. (1991) *Protein Engineering* 4:263-269. Preferred residues for substitutions include the surface exposed residues which would be predicted to interact with receptor. Other residues which should conserve function will be conservative substitutions, particularly at position far from the surface exposed residues.

IV. Functional Variants

The blocking of physiological response to IL-B50s may result from the competitive inhibition of binding of the ligand to its receptor.

In vitro assays of the present invention will often use isolated protein, soluble fragments comprising receptor binding segments of these proteins, or fragments attached to solid phase substrates. These assays will also allow for the diagnostic determination of the effects of either binding segment mutations and modifications, or cytokine mutations and modifications, e.g., IL-B50 analogs.

This invention also contemplates the use of competitive drug screening assays, e.g., where neutralizing antibodies to the cytokine, or receptor binding fragments compete with a test compound.

"Derivatives" of IL-B50 antigens include amino acid sequence mutants from naturally occurring forms, glycosylation variants, and covalent or aggregate conjugates with other chemical moieties. Covalent derivatives can be prepared by linkage of functionalities to groups which are found in IL-B50 amino acid side chains or at the N- or C-termini, e.g., by standard means. See, e.g., Lundblad and Noyes (1988) *Chemical Reagents for Protein Modification*, vols. 1-2, CRC Press, Inc., Boca Raton, Fla.; Hugli (ed. 1989) *Techniques in Protein Chemistry*, Academic Press, San Diego, Calif.; and Wong (1991) *Chemistry of Protein Conjugation and Cross Linking*, CRC Press, Boca Raton, Fla.

In particular, glycosylation alterations are included, e.g., made by modifying the glycosylation patterns of a polypeptide during its synthesis and processing, or in further processing steps. See, e.g., Elbein (1987) *Ann. Rev. Biochem.* 56:497-534. Also embraced are versions of the peptides with the same primary amino acid sequence which have other minor modifications, including phosphorylated amino acid residues, e.g., phosphotyrosine, phosphoserine, or phosphothreonine.

Fusion polypeptides between IL-B50s and other homologous or heterologous proteins are also provided. Many cytokine receptors or other surface proteins are multimeric, e.g., homodimeric entities, and a repeat construct may have various advantages, including lessened susceptibility to proteolytic cleavage. Typical examples are fusions of a reporter polypeptide, e.g., luciferase, with a segment or domain of a protein, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, yeast alpha mating factor, and detection or purification tags such as a FLAG sequence of His6 sequence. See, e.g., Godowski, et al. (1988) *Science* 241:812-816.

Fusion peptides will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1-3, Cold Spring Harbor Laboratory; and Ausubel, et al. (eds. 1993) *Current Protocols in Molecular Biology*, Greene and Wiley, NY. Techniques for synthesis of polypeptides are described, e.g., in Merrifield (1963) *J. Amer. Chem. Soc.* 85:2149-2156; Merrifield (1986) *Science* 232: 341-347; Atherton, et al. (1989) *Solid Phase Peptide Synthesis: A Practical Approach*, IRL Press, Oxford; and Grant (1992) *Synthetic Peptides: A User's Guide*, W.H. Freeman, N.Y. Refolding methods may be applicable to synthetic proteins.

This invention also contemplates the use of derivatives of IL-B50 proteins other than variations in amino acid sequence or glycosylation. Such derivatives may involve covalent or aggregative association with chemical moieties or protein carriers. Covalent or aggregative derivatives will be useful as immunogens, as reagents in immunoassays, or in purification methods such as for affinity purification of binding partners, e.g., other antigens. An IL-B50 can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-IL-B50 antibodies or an alternative binding composition. The IL-B50 proteins can also be labeled with a detectable group, e.g., for use in diagnostic assays. Purification of IL-B50 may be effected by an immobilized antibody or complementary binding partner, e.g., binding portion of a receptor.

A solubilized IL-B50 or fragment of this invention can be used as an immunogen for the production of antisera or antibodies specific for binding. Purified antigen can be used to screen monoclonal antibodies or antigen-binding fragments, encompassing antigen binding fragments of natural antibodies, e.g., Fab, Fab', F(ab)$_2$, etc. Purified IL-B50 antigens can also be used as a reagent to detect antibodies generated in response to the presence of elevated levels of the cytokine, which may be diagnostic of an abnormal or specific physiological or disease condition. This invention contemplates antibodies raised against amino acid sequences encoded by nucleotide sequence shown in SEQ ID NO: 1 or 3, or fragments of proteins containing it. In particular, this invention contemplates antibodies having binding affinity to or being raised against specific domains, e.g., helices A, B, C, or D.

The present invention contemplates the isolation of additional closely related species variants. Southern and Northern blot analysis will establish that similar genetic entities exist in other mammals. It is likely that IL-B50s are widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the molecules will be greatly accelerated by the isolation and characterization of additional distinct species or polymorphic variants of them. In particular, the present invention provides useful probes for identifying additional homologous genetic entities in different species.

The isolated genes will allow transformation of cells lacking expression of an IL-B50, e.g., either species types or cells which lack corresponding proteins and exhibit negative background activity. This should allow analysis of the function of IL-B50 in comparison to untransformed control cells.

Dissection of critical structural elements which effect the various physiological functions mediated through these antigens is possible using standard techniques of modern molecular biology, particularly in comparing members of the related class. See, e.g., the homolog-scanning mutagenesis technique described in Cunningham, et al. (1989) *Science* 243:1339-1336; and approaches used in O'Dowd, et al. (1988) *J. Biol. Chem.* 263:15985-15992; and Lechleiter, et al. (1990) *EMBO J.* 9:4381-4390.

Intracellular functions would probably involve receptor signaling. However, protein internalization may occur under certain circumstances, and interaction between intracellular components and cytokine may occur. Specific segments of interaction of IL-B50 with interacting components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of IL-B50 will be pursued. The controlling elements associated with the antigens should exhibit differential physiological, developmental, tissue specific, or other expression patterns. Upstream or downstream genetic regions, e.g., control elements, are of interest.

Structural studies of the IL-B50 antigens will lead to design of new antigens, particularly analogs exhibiting agonist or antagonist properties on the molecule. This can be combined with previously described screening methods to isolate antigens exhibiting desired spectra of activities.

V. Antibodies

Antibodies can be raised to various epitopes of the IL-B50 proteins, including species, polymorphic, or allelic variants, and fragments thereof, both in their naturally occurring forms and in their recombinant forms. Additionally, antibodies can be raised to IL-B50s in either their active forms or in their inactive forms, including native or denatured versions. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective IL-B50s, or screened for agonistic or antagonistic activity, e.g., mediated through a receptor. Antibodies may be agonistic or antagonistic, e.g., by sterically blocking binding to a receptor. These monoclonal antibodies will usually bind with at least a $K_D$ of about 1 mM, more usually at least about 300 μM, typically at least about 100 μM, more typically at least about 30 μM, preferably at least about 10 μM, and more preferably at least about 3 μM or better.

An IL-B50 protein that specifically binds to or that is specifically immunoreactive with an antibody generated against a defined immunogen, such as an immunogen consisting of the amino acid sequence of SEQ ID NO: 2 or 4, is typically determined in an immunoassay. The immunoassay typically uses a polyclonal antiserum which was raised, e.g., to a protein of SEQ ID NO: 2 or 4. This antiserum is selected to have low crossreactivity against other IL-7, e.g., human or rodent IL-7, preferably from the same species, and any such crossreactivity is removed by immunoabsorption prior to use in the immunoassay.

In order to produce antisera for use in an immunoassay, the protein of SEQ ID NO: 2 or 4, or a combination thereof, is isolated as described herein. For example, recombinant protein may be produced in a mammalian cell line. An appropriate host, e.g., an inbred strain of mice such as Balb/c, is immunized with the selected protein, typically using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other IL-7 family members, e.g., rodent IL-7, using a competitive binding immunoassay such as the one described in Harlow and Lane, supra, at pages 570-573. Preferably at least one other IL-7 family member is used in this determination in conjunction with, e.g., the primate IL-7. The IL-7 family members can be produced as recombinant proteins and isolated using standard molecular biology and protein chemistry techniques as described herein.

Immunoassays in the competitive binding format can be used for the crossreactivity determinations. For example, the protein of SEQ ID NO: 4 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 4. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein (e.g., the IL-7 like protein of SEQ ID NO: 2 or 4). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of the selected protein or proteins that is required, then the second protein is said to specifically bind to an antibody generated to the immunogen.

The antibodies of this invention can also be useful in diagnostic applications. As capture or non-neutralizing antibodies, they can be screened for ability to bind to the antigens without inhibiting binding to a receptor. As neutralizing antibodies, they can be useful in competitive binding assays. They will also be useful in detecting or quantifying IL-B50 protein or its receptors. See, e.g., Chan (ed. 1987) *Immunology: A Practical Guide*, Academic Press, Orlando, Fla.; Price and Newman (eds. 1991) *Principles and Practice of Immunoassay*, Stockton Press, N.Y.; and Ngo (ed. 1988) *Nonisotopic Immunoassay*, Plenum Press, N.Y. Cross absorptions, depletions, or other means will provide preparations of defined selectivity, e.g., unique or shared species specificities. These may be the basis for tests which will identify various groups of antigens.

Further, the antibodies, including antigen binding fragments, of this invention can be potent antagonists that bind to the antigen and inhibit functional binding, e.g., to a receptor which may elicit a biological response. They also can be useful as non-neutralizing antibodies and can be coupled to toxins or radionuclides so that when the antibody binds to antigen, a cell expressing it, e.g., on its surface, is killed. Further, these antibodies can be conjugated to drugs or other therapeutic agents, either directly or indirectly by means of a linker, and may effect drug targeting.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; Williams, et al. (1967) *Methods in Immunology and Immunochemistry*, vol. 1, Academic Press, New York; and Harlow and Lane (1988) *Antibodies: A Laboratory Manual*, CSH Press, NY, for descriptions of methods of preparing polyclonal antisera.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.), Academic Press, New York; and particularly in Kohler and Milstein (1975) in *Nature* 256:495-497, which discusses one method of generating monoclonal antibodies.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275-1281; and Ward, et al. (1989) *Nature* 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant or chimeric immunoglobulins may be produced, see Cabilly, U.S. Pat. No. 4,816,567; Moore, et al., U.S. Pat. No. 4,642,334; and Queen, et al. (1989) *Proc. Nat'l Acad. Sci. USA* 86:10029-10033; or made in transgenic mice, see Mendez, et al. (1997) *Nature Genetics* 15:146-156. These references are incorporated herein by reference.

The antibodies of this invention can also be used for affinity chromatography in isolating the protein. Columns can be prepared where the antibodies are linked to a solid support. See, e.g., Wilchek et al. (1984) *Meth. Enzymol.* 104:3-55. The converse may be used to purify antibodies.

Antibodies raised against each IL-B50 will also be useful to raise anti-idiotypic antibodies. These will be useful in detecting or diagnosing various immunological conditions related to expression of the respective antigens.

VI. Nucleic Acids

The described peptide sequences and the related reagents are useful in detecting, isolating, or identifying a DNA clone encoding IL-B50, e.g., from a natural source. Typically, it will be useful in isolating a gene from mammal, and similar procedures will be applied to isolate genes from other species, e.g., warm blooded animals, such as birds and mammals. Cross hybridization will allow isolation of IL-B50 from the same, e.g., polymorphic variants, or other species. A number of different approaches will be available to successfully isolate a suitable nucleic acid clone.

The purified protein or defined peptides are useful for generating antibodies by standard methods, as described above. Synthetic peptides or purified protein can be presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual*, Cold Spring Harbor Press.

For example, the specific binding composition could be used for screening of an expression library made from a cell line which expresses an IL-B50. Screening of intracellular expression can be performed by various staining or immunofluorescence procedures. Binding compositions could be used to affinity purify or sort out cells expressing a surface fusion protein.

The peptide segments can also be used to predict appropriate oligonucleotides to screen a library. The genetic code can be used to select appropriate oligonucleotides useful as probes for screening. See, e.g., SEQ ID NO: 1 or 3. In combination with polymerase chain reaction (PCR) techniques, synthetic oligonucleotides will be useful in selecting correct clones from a library. Complementary sequences will also be used as probes, primers, or antisense strands. Various fragments should be particularly useful, e.g., coupled with anchored vector or poly-A complementary PCR techniques or with complementary DNA of other peptides.

This invention contemplates use of isolated DNA or fragments to encode a biologically active corresponding IL-B50 polypeptide, particularly lacking the portion coding the untranslated 5' portion of the described sequence. In addition, this invention covers isolated or recombinant DNA which encodes a biologically active protein or polypeptide and which is capable of hybridizing under appropriate conditions with the DNA sequences described herein. Said biologically active protein or polypeptide can be an intact antigen, or fragment, and have an amino acid sequence disclosed in, e.g., SEQ ID NO: 2 or 4, particularly a mature, secreted polypeptide. Further, this invention covers the use of isolated or recombinant DNA, or fragments thereof, which encode proteins which exhibit high identity to a secreted IL-B50. The isolated DNA can have the respective regulatory sequences in the 5' and 3' flanks, e.g., promoters, enhancers, poly-A addition signals, and others. Alternatively, expression may be effected by operably linking a coding segment to a heterologous promoter, e.g., by inserting a promoter upstream from an endogenous gene. See, e.g., Treco, et al. WO96/29411 or U.S. Ser. No. 08/406,030.

An "isolated" nucleic acid is a nucleic acid, e.g., an RNA, DNA, or a mixed polymer, which is substantially separated from other components which naturally accompany a native sequence, e.g., ribosomes, polymerases, and/or flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Generally, the nucleic acid will be in a vector or fragment less than about 50 kb, usually less than about 30 kb, typically less than about 10 kb, and preferably less than about 6 kb.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, e.g., products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species or polymorphic variants.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides, e.g., 67, 73, 81, 89, 95, etc.

A DNA which codes for an IL-B50 protein will be particularly useful to identify genes, mRNA, and cDNA species which code for related or similar proteins, as well as DNAs which code for homologous proteins from different species. There will be homologs in other species, including primates, rodents, canines, felines, and birds. Various IL-B50 proteins should be homologous and are encompassed herein. However, even proteins that have a more distant evolutionary relationship to the antigen can readily be isolated under appropriate conditions using these sequences if they are sufficiently homologous. Primate IL-B50 proteins are of particular interest.

Recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology*, Academic Press, San Diego, pp. 1502-1504; Travis (1992) *Science* 256:1392-1394; Kuhn, et al. (1991) *Science* 254:707-710; Capecchi (1989) *Science* 244:1288; Robertson (ed. 1987) *Teratocarcinomas and Embryonic Stem Cells: A Practical Approach*, IRL Press, Oxford; and Rosenberg (1992) *J. Clinical Oncology* 10:180-199.

Substantial homology, e.g., identity, in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence of IL-B50, e.g., in SEQ ID NO: 1 or 3. Typically, selective hybridization will occur when there is at least about 55% identity over a stretch of at least about 30 nucleotides, preferably at least about 75% over a stretch of about 25 nucleotides, and most preferably at least about 90% over about 20 nucleotides. See, Kanehisa (1984) *Nuc. Acids*

Res. 12:203-213. The length of identity comparison, as described, may be over longer stretches, and in certain embodiments will be over a stretch of at least about 17 nucleotides, usually at least about 28 nucleotides, typically at least about 40 nucleotides, and preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., usually in excess of about 37° C., typically in excess of about 55° C., 60° C., 65° C., or preferably in excess of about 70° C. Stringent salt conditions will ordinarily be less than about 1000 or 600 mM usually less than about 400 mM, typically less than about 250 mM, preferably less than about 150 mM, including about 100, 50, or even 20 mM. However, the combination of parameters is much more important than the measure of any single parameter. See, e.g., Wetmur and Davidson (1968) *J. Mol. Biol.* 31:349-370. Hybridization under stringent conditions should give a background of at least 2-fold over background, preferably at least 3-5 or more.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng and Doolittle (1987) *J. Mol. Evol.* 35:351-360. The method used is similar to the method described by Higgins and Sharp (1989) *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al. (1990) *J. Mol, Biol.* 215:403-410. Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) *Proc. Nat'l Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

IL-B50 from other mammalian species can be cloned and isolated by cross-species hybridization of closely related species. Homology may be relatively low between distantly related species, and thus hybridization of relatively closely related species is advisable. Alternatively, preparation of an antibody preparation which exhibits less species specificity may be useful in expression cloning approaches.

VII. Making IL-B50; Mimetics

DNA which encodes the IL-B50 or fragments thereof can be obtained by chemical synthesis, screening cDNA libraries, or screening genomic libraries prepared from a wide variety of cell lines or tissue samples. See, e.g., Okayama and Berg (1982) *Mol. Cell. Biol.* 2:161-170; Gubler and Hoffman (1983) *Gene* 25:263-269; and Glover (ed. 1984) *DNA Clon-* ing: A Practical Approach, IRL Press, Oxford. Alternatively, the sequences provided herein provide useful PCR primers or allow synthetic or other preparation of suitable genes encoding an IL-B50; including naturally occurring embodiments.

This DNA can be expressed in a wide variety of host cells for the synthesis of a full-length IL-B50 or fragments which can in turn, e.g., be used to generate polyclonal or monoclonal antibodies; for binding studies; for construction and expression of modified molecules; and for structure/function studies.

Vectors, as used herein, comprise plasmids, viruses, bacteriophage, integratable DNA fragments, and other vehicles which enable the integration of DNA fragments into the genome of the host. See, e.g., Pouwels, et al. (1985 and Supplements) *Cloning Vectors: A Laboratory Manual*, Elsevier, N.Y.; and Rodriguez, et al. (eds. 1988) *Vectors: A Survey of Molecular Cloning Vectors and Their Uses*, Buttersworth, Boston, Mass.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression. See, e.g., Rodriguez, et al., Chapter 10, pp. 205-236; Balbas and Bolivar (1990) *Methods in Enzymology* 185:14-37; and Ausubel, et al. (1993) *Current Protocols in Molecular Biology*, Greene and Wiley, NY.

Representative examples of suitable expression vectors include pcDNA1; pCD, see Okayama, et al. (1985) *Mol. Cell. Biol.* 5:1136-1142; pMC1neo Poly-A, see Thomas, et al. (1987) *Cell* 51:503-512; and a baculovirus vector such as pAC 373 or pAC 610. See, e.g., Miller (1988) *Ann. Rev. Microbiol.* 42:177-199.

It will often be desired to express an IL-B50 polypeptide in a system which provides a specific or defined glycosylation pattern. See, e.g., Luckow and Summers (1988) *Bio/Technology* 6:47-55; and Kaufman (1990) *Meth. Enzymol.* 185:487-511.

The IL-B50, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427-454; Tse, et al. (1985) *Science* 230:1003-1008; and Brunner, et al. (1991) *J. Cell Biol.* 114:1275-1283.

Now that the IL-B50 has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; Bodanszky (1984) *The Principles of Peptide Synthesis*, Springer-Verlag, New York; and Villafranca (ed. 1991) *Techniques in Protein Chemistry II*, Academic Press, San Diego, Calif.

VIII. Uses

The present invention provides reagents which will find use in diagnostic applications as described elsewhere herein, e.g., in IL-B50 mediated conditions, or below in the description of kits for diagnosis. The gene may be useful in forensic sciences, e.g., to distinguish rodent from human, or as a marker to distinguish between different cells exhibiting differential expression or modification patterns.

This invention also provides reagents with significant commercial and/or therapeutic potential. The IL-B50 (naturally occurring or recombinant), fragments thereof, and antibodies thereto, along with compounds identified as having binding affinity to IL-B50, should be useful as reagents for teaching techniques of molecular biology, immunology, or physiology. Appropriate kits may be prepared with the reagents, e.g., in practical laboratory exercises in production or use of proteins, antibodies, cloning methods, histology, etc.

The reagents will also be useful in the treatment of conditions associated with abnormal physiology or development, including inflammatory conditions. They may be useful in vitro tests for presence or absence of interacting components, which may correlate with success of particular treatment strategies. In particular, modulation of physiology of various, e.g., hematopoietic or lymphoid, cells will be achieved by appropriate methods for treatment using the compositions provided herein. See, e.g., Thomson (ed. 1998) *The Cytokine Handbook* (3d ed.) Academic Press, San Diego; Metcalf and Nicola (1995) *The Hematopoietic Colony Stimulating Factors* Cambridge University Press; and Aggarwal and Gutterman (1991) *Human Cytokines* Blackwell Pub.

For example, a disease or disorder associated with abnormal expression or abnormal signaling by an IL-B50 should be a likely target for an agonist or antagonist. The new cytokine should play a role in regulation or development of hematopoietic cells, e.g., lymphoid cells, which affect immunological responses, e.g., inflammation and/or autoimmune disorders. Alternatively, it may affect vascular physiology or development, or neuronal effects.

In particular, the cytokine should mediate, in various contexts, cytokine synthesis by the cells, proliferation, etc. Antagonists of IL-B50, such as mutein variants of a naturally occurring form of IL-B50 or blocking antibodies, may provide a selective and powerful way to block immune responses, e.g., in situations as inflammatory or autoimmune responses. See also Samter, et al. (eds.) *Immunological Diseases* vols. 1 and 2, Little, Brown and Co.

Various abnormal conditions are known in different cell types which will produce IL-B50, e.g., as evaluated by mRNA expression by Northern blot analysis. See Berkow (ed.) *The Merck Manual of Diagnosis and Therapy*, Merck & Co., Rahway, N.J.; Thorn, et al. *Harrison's Principles of Internal Medicine*, McGraw-Hill, N.Y.; and Weatherall, et al. (eds.) *Oxford Textbook of Medicine*, Oxford University Press, Oxford. Many other medical conditions and diseases involve activation by macrophages or monocytes, and many of these will be responsive to treatment by an agonist or antagonist provided herein. See, e.g., Stites and Terr (eds.; 1991) *Basic and Clinical Immunology* Appleton and Lange, Norwalk, Conn.; and Samter, et al. (eds.) *Immunological Diseases* Little, Brown and Co. These problems should be susceptible to prevention or treatment using compositions provided herein.

IL-B50, antagonists, antibodies, etc., can be purified and then administered to a patient, veterinary or human. These reagents can be combined for therapeutic use with additional active or inert ingredients, e.g., in conventional pharmaceutically acceptable carriers or diluents, e.g., immunogenic adjuvants, along with physiologically innocuous stabilizers, excipients, or preservatives. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using IL-B50 or fragments thereof can be performed to identify compounds having binding affinity to or other relevant biological effects on IL-B50 functions, including isolation of associated components. Subsequent biological assays can then be utilized to determine if the compound has intrinsic stimulating activity and is therefore a blocker or antagonist in that it blocks the activity of the cytokine. Likewise, a compound having intrinsic stimulating activity can activate the signal pathway and is thus an agonist in that it simulates the activity of IL-B50. This invention further contemplates the therapeutic use of blocking antibodies to IL-B50 as antagonists and of stimulatory antibodies as agonists. This approach should be particularly useful with other IL-B50 species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) *Goodman and Gilman's: The Pharmacological Bases of Therapeutics*, latest Ed., Pergamon Press; and *Remington's Pharmaceutical Sciences*, latest ed., Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 μM concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous or long term administration. See, e.g., Langer (1990) *Science* 249:1527-1533.

IL-B50, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, topical, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds. 1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa.; Avis, et al. (eds. 1993) *Pharmaceutical Dosage Forms: Parenteral Medications*, Dekker, New York; Lieberman, et al. (eds. 1990) *Pharmaceutical Dosage Forms: Tablets*, Dekker, New York; and Lieberman, et al. (eds. 1990) *Pharmaceutical Dosage Forms: Disperse Systems*, Dekker, New York. The therapy of this invention may be combined with or used in association with other agents, e.g., other cytokines, including IL-7, or its antagonists.

Both naturally occurring and recombinant forms of the IL-B50s of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767-773, which describes means for testing of binding affinity by a plurality of defined polymers synthesized on a solid substrate. The development of suitable assays can be greatly facilitated by the availability of large amounts of purified, soluble IL-B50 as provided by this invention.

Other methods can be used to determine the critical residues in IL-B50-IL-B50 receptor interactions. Mutational analysis can be performed, e.g., see Somoza, et al. (1993) *J. Exptl. Med.* 178:549-558, to determine specific residues critical in the interaction and/or signaling. PHD (Rost and Sander (1994) *Proteins* 19:55-72) and DSC (King and Sternberg (1996) *Protein Sci.* 5:2298-2310) can provide secondary structure predictions of α-helix (H), β-strand (E), or coil (L). Helices A and D are most important in receptor interaction, with the D helix the more important region. Helix A would run (SEQ ID NO: 4) in the human from about lys10 to tyr26, helix B would run from about his46 to asn57; helix C would run from about glu68 to trp81; and helix D would run from about asn107 to position about leu127. Surface exposed residues would affect receptor binding, while embedded residues would affect general structure.

For example, antagonists can normally be found once the antigen has been structurally defined, e.g., by tertiary structure data. Testing of potential interacting analogs is now possible upon the development of highly automated assay methods using a purified IL-B50. In particular, new agonists and antagonists will be discovered by using screening techniques described herein. Of particular importance are compounds found to have a combined binding affinity for a spectrum of IL-B50 molecules, e.g., compounds which can serve as antagonists for species variants of IL-B50.

One method of drug screening utilizes eukaryotic or prokaryotic host cells which are stably transformed with recombinant DNA molecules expressing an IL-B50. Cells may be isolated which express an IL-B50 in isolation from other molecules. Such cells, either in viable or fixed form, can be used for standard binding partner binding assays. See also, Parce, et al. (1989) *Science* 246:243-247; and Owicki, et al. (1990) *Proc. Nat'l Acad. Sci. USA* 87:4007-4011, which describe sensitive methods to detect cellular responses.

Another technique for drug screening involves an approach which provides high throughput screening for compounds having suitable binding affinity to an IL-B50 and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified IL-B50, and washed. The next step involves detecting bound IL-B50.

Rational drug design may also be based upon structural studies of the molecular shapes of the IL-B50 and other effectors or analogs. Effectors may be other proteins which mediate other functions in response to binding, or other proteins which normally interact with IL-B50, e.g., a receptor. One means for determining which sites interact with specific other proteins is a physical structure determination, e.g., x-ray crystallography or 2 dimensional NMR techniques. These will provide guidance as to which amino acid residues form molecular contact regions, as modeled, e.g., against other cytokine-receptor models. For a detailed description of protein structural determination, see, e.g., Blundell and Johnson (1976) *Protein Crystallography*, Academic Press, New York.

IX. Kits

This invention also contemplates use of IL-B50 proteins, fragments thereof, peptides, and their fusion products in a variety of diagnostic kits and methods for detecting the presence of another IL-B50 or binding partner. Typically the kit will have a compartment containing either a defined IL-B50 peptide or gene segment or a reagent which recognizes one or the other, e.g., IL-B50 fragments or antibodies.

A kit for determining the binding affinity of a test compound to an IL-B50 would typically comprise a test compound; a labeled compound, for example a binding partner or antibody having known binding affinity for IL-B50; a source of IL-B50 (naturally occurring or recombinant); and a means for separating bound from free labeled compound, such as a solid phase for immobilizing the molecule. Once compounds are screened, those having suitable binding affinity to the antigen can be evaluated in suitable biological assays, as are well known in the art, to determine whether they act as agonists or antagonists to the IL-B50 signaling pathway. The availability of recombinant IL-B50 polypeptides also provide well defined standards for calibrating such assays.

A preferred kit for determining the concentration of, e.g., an IL-B50 in a sample would typically comprise a labeled compound, e.g., binding partner or antibody, having known binding affinity for the antigen, a source of cytokine (naturally occurring or recombinant) and a means for separating the bound from free labeled compound, e.g., a solid phase for immobilizing the IL-B50. Compartments containing reagents, and instructions, will normally be provided.

Antibodies, including antigen binding fragments, specific for the IL-B50 or fragments are useful in diagnostic applications to detect the presence of elevated levels of IL-B50 and/or its fragments. Such diagnostic assays can employ lysates, live cells, fixed cells, immunofluorescence, cell cultures, body fluids, and further can involve the detection of antigens related to the antigen in serum, or the like. Diagnostic assays may be homogeneous (without a separation step between free reagent and antigen-binding partner complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis, et al. (1980) *Meth Enzymol.* 70:1-525; Harlow and Lane (1980) *Antibodies: A Laboratory Manual*, CSH Press, NY; and Coligan, et al. (eds. 1993) *Current Protocols in Immunology*, Greene and Wiley, NY.

Anti-idiotypic antibodies may have similar use to diagnose presence of antibodies against an IL-B50, as such may be diagnostic of various abnormal states. For example, overproduction of IL-B50 may result in production of various immunological reactions which may be diagnostic of abnormal physiological states, particularly in proliferative cell conditions such as cancer or abnormal activation or differentiation. Moreover, the distribution pattern available provides information that the cytokine is expressed in pancreatic islets, suggesting the possibility that the cytokine may be involved in function of that organ, e.g., in a diabetes relevant medical condition.

Frequently, the reagents for diagnostic assays are supplied in kits, so as to optimize the sensitivity of the assay. For the subject invention, depending upon the nature of the assay, the protocol, and the label, either labeled or unlabeled antibody or binding partner, or labeled IL-B50 is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the binding partner, test compound, IL-B50, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free IL-B50, or alternatively the bound from the free test compound. The IL-B50 can be immobilized on various matrixes followed by washing. Suitable matrixes include plastic such as an ELISA plate, filters, and beads. See, e.g., Coligan, et al. (eds. 1993) *Current Protocols in Immunology*, Vol. 1, Chapter 2, Greene and Wiley, NY. Other suitable separation techniques include, without limitation, the fluorescein antibody magnetizable particle method described in Rattle, et al. (1984) *Clin. Chem.* 30:1457-1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an IL-B50. These sequences can be used as probes for detecting levels of the IL-B50 message in samples from patients suspected of having an abnormal condition, e.g., inflammatory or autoimmune. Since the cytokine may be a marker or mediator for activation, it may be useful to determine the numbers of activated cells to determine, e.g., when additional therapy may be called for, e.g., in a preventative fashion before the effects become and progress to significance. The preparation of both RNA and DNA nucleotide sequences, the labeling of the sequences, and the preferred size of the sequences has received ample description and discussion in the literature. See, e.g., Langer Safer, et al. (1982) *Proc. Nat'l. Acad. Sci.* 79:4381-4385; Caskey (1987) *Science* 236:962-967; and Wilchek et al. (1988) *Anal. Biochem.* 171:1-32.

Diagnostic kits which also test for the qualitative or quantitative expression of other molecules are also contemplated. Diagnosis or prognosis may depend on the combination of multiple indications used as markers. Thus, kits may test for combinations of markers. See, e.g., Viallet, et al. (1989) *Progress in Growth Factor Res.* 1:89-97. Other kits may be used to evaluate other cell subsets.

X. Isolating an IL-B50 Receptor

Having isolated a ligand of a specific ligand-receptor interaction, methods exist for isolating the receptor. See, Gearing, et al. (1989) *EMBO J.* 8:3667-3676. For example, means to label the IL-B50 cytokine without interfering with the binding to its receptor can be determined. For example, an affinity label can be fused to either the amino- or carboxyl-terminus of the ligand. Such label may be a FLAG epitope tag, or, e.g., an Ig or Fc domain. An expression library can be screened for specific binding of the cytokine, e.g., by cell sorting, or other screening to detect subpopulations which express such a binding component. See, e.g., Ho, et al. (1993) *Proc. Nat'l Acad. Sci. USA* 90:11267-11271; and Liu, et al. (1994) *J. Immunol.* 152:1821-29. Alternatively, a panning method may be used. See, e.g., Seed and Aruffo (1987) *Proc. Nat'l Acad. Sci. USA* 84:3365-3369.

Protein cross-linking techniques with label can be applied to isolate binding partners of the IL-B50 cytokine. This would allow identification of proteins which specifically interact with the cytokine, e.g., in a ligand-receptor like manner. It is predicted that the IL-B50 will bind to the IL-7R alpha subunit, but this is likely to the beta subunit in the IL-B50 receptor. Thus, another subunit would serve as the alpha receptor subunit for the IL-B50.

Early experiments will be performed, as predicted, to determine whether the known IL-7 receptor components are involved in response(s) to IL-B50. It is also quite possible that these functional receptor complexes may share many or all components with an IL-B50 receptor complex, either a specific receptor subunit or an accessory receptor subunit.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

EXAMPLES

I. General Methods

Many of the standard methods below are described or referenced, e.g., in Maniatis, et al. (1982) *Molecular Cloning, A Laboratory Manual* Cold Spring Harbor Laboratory, Cold Spring Harbor Press, NY; Sambrook, et al. (1989) *Molecular Cloning: A Laboratory Manual* (2d ed.) Vols. 1-3, CSH Press, NY; Ausubel, et al., *Biology* Greene Publishing Associates, Brooklyn, N.Y.; or Ausubel, et al. (1987 and Supplements) *Current Protocols in Molecular Biology* Wiley/Greene, N.Y.; Innis, et al. (eds. 1990) *PCR Protocols: A Guide to Methods and Applications* Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology vol.* 182, and other volumes in this series; Coligan, et al. (1995 and supplements) *Current Protocols in Protein Science* John Wiley and Sons, New York, N.Y.; Matsudaira (ed. 1993) *A Practical Guide to Protein and Peptide Purification for Microsequencing*, Academic Press, San Diego, Calif.; and manufacturer's literature on use of protein purification products, e.g., Pharmacia, Piscataway, N.J., or Bio-Rad, Richmond, Calif. Combination with recombinant techniques allow fusion to appropriate segments (epitope tags), e.g., to a FLAG sequence or an equivalent which can be fused, e.g., via a protease-removable sequence. See, e.g., Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, NY; and Crowe, et al. (1992) *QIAexpress: The High Level Expression & Protein Purification System* QUIAGEN, Inc., Chatsworth, Calif.

Standard immunological techniques are described, e.g., in Hertzenberg, et al. (eds. 1996) *Weir's Handbook of Experimental Immunology* vols. 1-4, Blackwell Science; Coligan (1991) *Current Protocols in Immunology* Wiley/Greene, N.Y.; and *Methods in Enzymology* vols. 70, 73, 74, 84, 92, 93, 108, 116, 121, 132, 150, 162, and 163. Cytokine assays are described, e.g., in Thomson (ed. 1998) *The Cytokine Handbook* (3d ed.) Academic Press, San Diego; Mire-Sluis and Thorpe (1998) *Cytokines* Academic Press, San Diego; Metcalf and Nicola (1995) *The Hematopoietic Colony Stimulating Factors* Cambridge University Press; and Aggarwal and Gutterman (1991) *Human Cytokines* Blackwell Pub.

Assays for vascular biological activities are well known in the art. They will cover angiogenic and angiostatic activities in tumor, or other tissues, e.g., arterial smooth muscle proliferation (see, e.g., Koyoma, et al. (1996) *Cell* 87:1069-1078), monocyte adhesion to vascular epithelium (see McEvoy, et al. (1997) *J. Exp. Med.* 185:2069-2077), etc. See also Ross (1993) *Nature* 362:801-809; Rekhter and Gordon (1995) *Am. J. Pathol.* 147:668-677; Thyberg, et al. (1990) *Atherosclerosis* 10:966-990; and Gumbiner (1996) *Cell* 84:345-357.

Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Cloning of Human IL-B50

The sequence of the gene is provided in SEQ ID NO: 1 and 3. The sequence is derived from a cDNA library made from testes. The sequence is quite rare, not being found with frequency in available sequence databases. This sequence allows preparation of PCR primers, or probes, to determine cellular distribution of the gene. The sequence allows isolation of genomic DNA which encode the message.

Using the probe or PCR primers, various tissues or cell types are probed to determine cellular distribution. PCR products are cloned using, e.g., a TA cloning kit (Invitrogen). The resulting cDNA plasmids are sequenced from both termini on an automated sequencer (Applied Biosystems).

III. Cellular Expression of IL-B50

An appropriate probe or primers specific for cDNA encoding primate IL-B50 are prepared. Typically, the probe is labeled, e.g., by random priming.

Southern Analysis: DNA (5 µg) from a primary amplified cDNA library was digested with appropriate restriction enzymes to release the inserts, run on a 1% agarose gel and transferred to a nylon membrane (Schleicher and Schuell, Keene, N.H.).

Samples for human mRNA isolation may include: peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot 72, activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111); T cell tumor lines Jurkat and Hut78, resting (T117); T cell clones, pooled AD130.2, Tc783.12, Tc783.13, Tc783.58, Tc782.69, resting (T118); T cell random γδ cell clones, resting (T119); CD28-T cell clone; Splenocytes, resting (B100); Splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); NK 20 clones pooled, resting (K100); NK 20 clones pooled, activated with PMA and ionomycin for 6 h (K101); NKL clone, derived from peripheral blood of LGL leukemia patient, IL-2 treated (K106); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFNγ, anti-IL-10 for 1, 2, 6, 12, 24 h pooled (M102); elutriated monocytes, activated with LPS, IFNγ, IL-10 for 1, 2, 6, 12, 24 h pooled (M103); elutriated monocytes, activated with LPS, IFNγ, anti-IL-10 for 4, 16 h pooled (M106); elutriated monocytes, activated with LPS, IFNγ, IL-10 for 4, 16 h pooled (M107); elutriated monocytes, activated LPS for 1 h (M108); elutriated monocytes, activated LPS for 6 h (M109); DC 70% CD1a+, from CD34+ GM-CSF, TNFα 12 days, resting (D101); DC 70% CD1a+, from CD34+ GM-CSF, TNFα 12 days, activated with PMA and ionomycin for 1 hr (D102); DC 70% CD1a+, from CD34+ GM-CSF, TNFα 12 days, activated with PMA and ionomycin for 6 hr (D103); DC 95% CD1a+, from CD34+ GM-CSF, TNFα 12 days FACS sorted, activated with PMA and ionomycin for 1, 6 h pooled (D104); DC 95% CD14+, ex CD34+ GM-CSF, TNFα 12 days FACS sorted, activated with PMA and ionomycin 1, 6 hr pooled (D105); DC CD1a+ CD86+, from CD34+ GM-CSF, TNFα 12 days FACS sorted, activated with PMA and ionomycin for 1, 6 h pooled (D106); DC from monocytes GM-CSF, IL-4 5 days, resting (D107); DC from monocytes GM-CSF, IL-4 5 days, resting (D108); DC from monocytes GM-CSF, IL-4 5 days, activated LPS 4, 16 h pooled (D109); DC from monocytes GM-CSF, IL-4 5 days, activated TNFα, monocyte supe for 4, 16 h pooled (D110); epithelial cells, unstimulated; epithelial cells, IL-1β activated; lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102).

A mouse counterpart will be identified, and its distributions will be similarly evaluated. Samples for mouse mRNA isolation can include: resting mouse fibroblastic L cell line (C200); Braf:ER (Braf fusion to estrogen receptor) transfected cells, control (C201); Mel14+ naive T cells from spleen, resting (T209); Mel14+ naive T cells from spleen, stimulated with IFNγ, IL-12, and anti IL-4 to polarize to TH1 cells, exposed to IFNγ and IL-4 for 6, 12, 24 h, pooled (T210); Mel14+ naive T cells from spleen, stimulated with IL-4 and anti IFNγ to polarize to Th2 cells, exposed to IL-4 and anti IFNγ for 6, 13, 24 h, pooled (T211); T cells, TH1 polarized (Mel14 bright, CD4+ cells from spleen, polarized for 7 days with IFN-γ and anti IL-4; T200); T cells, TH2 polarized (Mel14 bright, CD4+ cells from spleen, polarized for 7 days with IL-4 and anti-IFN-γ; T201); T cells, highly TH1 polarized 3× from transgenic Balb/C (see Openshaw, et al. (1995) J. Exp. Med. 182:1357-1367; activated with anti-CD3 for 2, 6, 24 h pooled; T202); T cells, highly TH2 polarized 3× from transgenic Balb/C (activated with anti-CD3 for 2, 6, 24 h pooled (T203); T cells, highly TH1 polarized 3× from transgenic C57 bl/6 (activated with anti-CD3 for 2, 6, 24 h pooled; T212); T cells, highly TH2 polarized 3× from transgenic C57 bl/6 (activated with anti-CD3 for 2, 6, 24 h pooled; T213); T cells, highly TH1 polarized (naive CD4+ T cells from transgenic Balb/C, polarized 3× with IFNγ, IL-12, and anti-IL-4; stimulated with IGIF, IL-12, and anti IL-4 for 6, 12, 24 h, pooled); CD44− CD25+ pre T cells, sorted from thymus (T204); TH1 T cell clone D1.1, resting for 3 weeks after last stimulation with antigen (T205); TH1 T cell clone D1.1, 10 µg/ml ConA stimulated 15 h (T206); TH2 T cell clone CDC35, resting for 3 weeks after last stimulation with antigen (T207); TH2 T cell clone CDC35, 10 µg/ml ConA stimulated 15 h (T208); unstimulated B cell line CH12 (B201); unstimulated mature B cell leukemia cell line A20 (B200); unstimulated large B cells from spleen (B202); B cells from total spleen, LPS activated (B203); metrizamide enriched dendritic cells from spleen, resting (D200); dendritic cells from bone marrow, resting (D201); unstimulated bone marrow derived dendritic cells depleted with anti 8220, anti CD3, and anti Class II, cultured in GM-CSF and IL-4 (D202); bone marrow derived dendritic cells depleted with anti 8220, anti CD3, and anti Class II, cultured in GM-CSF and IL-4, stimulated with anti CD40 for 1, 5 d, pooled (D203); monocyte cell line RAW 264.7 activated with LPS 4 h (M200); bone-marrow macrophages derived with GM and M-CSF (M201); bone-marrow macrophages derived with GM-CSF, stimulated with LPS, IFNγ, and IL-10 for 24 h (M205); bone-marrow macrophages derived with GM-CSF, stimulated with LPS, IFNγ, and anti IL-10 for 24 h (M206); peritoneal macrophages (M207); macrophage cell line J774, resting (M202); macrophage cell line J774+ LPS+anti-IL-10 at 0.5, 1, 3, 6, 12 h pooled (M203); macrophage cell line J774+ LPS+IL-10 at 0.5, 1, 3, 5, 12 h pooled (M204); unstimulated mast cell lines MC-9 and MCP-12 (M208); immortalized endothelial cell line derived from brain microvascular endothelial cells, unstimulated (E200); immortalized endothelial cell line derived from brain microvascular endothelial cells, stimulated overnight with TNFα (E201); immortalized endothelial cell line derived from brain microvascular endothelial cells, stimulated overnight with TNFα (E202); immortalized endothelial cell line derived from brain microvascular endothelial cells, stimulated overnight with TNFα and IL-10 (E203); total aorta from wt C57 bl/6 mouse; total aorta from 5 month ApoE KO mouse (X207); total aorta from 12 month ApoE KO mouse (X207); wt thymus (O214); total thymus, rag-1 (O208); total kidney, rag-1 (O209); total kidney, NZ B/W mouse; and total heart, rag-1 (O202). High signal was detected in the monocyte cell line RAW 264.7 activated with LPS 4 h (M200); T cells, highly TH1 polarized 3× from transgenic C57 bl/6 (activated with anti-CD3 for 2, 6, 24 h pooled; T212); and T cells, highly TH1 polarized (naive CD4+ T cells from transgenic Balb/C, polarized 3× with IFNγ, IL-12, and anti-IL-4; stimulated with IGIF, IL-12, and anti IL-4 for 6, 12, 24 h, pooled).

IV. Chromosome Mapping of IL-B50

An isolated cDNA encoding the IL-B50 is used. Chromosome mapping is a standard technique. See, e.g., BIOS Laboratories (New Haven, Conn.) and methods for using a mouse somatic cell hybrid panel with PCR.

V. Purification of IL-B50 Protein

Multiple transfected cell lines are screened for one which expresses the cytokine at a high level compared with other cells. Various cell lines are screened and selected for their favorable properties in handling. Natural IL-B50 can be isolated from natural sources, or by expression from a transformed cell using an appropriate expression vector. Higher efficiency of secretion has been achieved by use of a heterologous signal sequence. Purification of the expressed protein is achieved by standard procedures, or may be combined with engineered means for effective purification at high efficiency from cell lysates or supernatants. FLAG or His6 segments can be used for such purification features. Alternatively, affinity chromatography may be used with specific antibodies, see below.

Protein is produced in coli, insect cell, or mammalian expression systems, as desired.

VI. Isolation of Homologous IL-B50 Genes

The IL-B50 cDNA, or other species counterpart sequence, can be used as a hybridization probe to screen a library from a desired source, e.g., a primate cell cDNA library. Many different species can be screened both for stringency necessary for easy hybridization, and for presence using a probe. Appropriate hybridization conditions will be used to select for clones exhibiting specificity of cross hybridization.

Screening by hybridization using degenerate probes based upon the peptide sequences will also allow isolation of appropriate clones. Alternatively, use of appropriate primers for PCR screening will yield enrichment of appropriate nucleic acid clones.

Similar methods are applicable to isolate either species, polymorphic, or allelic variants. Species variants are isolated using cross-species hybridization techniques based upon isolation of a full length isolate or fragment from one species as a probe.

Alternatively, antibodies raised against human IL-B50 will be used to screen for cells which express cross-reactive proteins from an appropriate, e.g., cDNA library. The purified protein or defined peptides are useful for generating antibodies by standard methods, as described above. Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. The resulting antibodies are used for screening, purification, or diagnosis, as described.

VII. Preparation of Antibodies Specific for IL-B50

Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. Polyclonal serum, or hybridomas may be prepared. In appropriate situations, the binding reagent is either labeled as described above, e.g., fluorescence or otherwise, or immobilized to a substrate for panning methods. Immunoselection, absorptions, depletions, and related techniques are available to prepare selective reagents, e.g., exhibiting the desired spectrum of selectivity for binding.

VIII. Evaluation of Breadth of Biological Functions

Biological activities of IL-B50 are tested, based, in part, on the sequence and structural homology between IL-B50 and IL-7. Initially, assays that show biological activities of IL-7 are examined.

A. Effects on Proliferation/Differentiation of Progenitor Cells

The effect on proliferation or differentiation of various cell types are evaluated with various concentrations of cytokine. A dose response analysis is performed, in certain cases in combination with the related cytokine IL-7 and/or stem cell factor.

In particular, IL-7 exhibits strong effects on lymphopoietic development and differentiation. The IL-B50 will be tested on cord blood cells to see if it has effects on proliferation or differentiation of early progenitor cells derived therefrom. Preferably, the cells are early precursor cells, e.g., stem cells, originating from, e.g., cord blood, bone marrow, thymus, spleen, or CD34+ progenitor cells. See, e.g., Eddington and Lotze (1998).

B. Effects of IL-B50 on Proliferation of Human Peripheral Blood Mononuclear Cells (PBMC)

Total PBMC are isolated from buffy coats of normal healthy donors by centrifugation through ficoll-hypaque as described (Boyum, et al.). PBMC are cultured in 200 μl Yssel's medium (Gemini Bioproducts, Calabasas, Calif.) containing 1% human AB serum in 96 well plates (Falcon, Becton-Dickinson, N.J.) in the absence or presence of IL-B50. Cells are cultured in medium alone or in combination with 100 U/ml IL-2 (R&D Systems) for 120 hours. 3H-Thymidine (0.1 mCi) is added during the last six hours of culture and 3H-Thymidine incorporation determined by liquid scintillation counting.

The native, recombinant, and fusion proteins would be tested for agonist and antagonist activity in many other biological assay systems, e.g., on T-cells, B-cells, NK, macrophages, dendritic cells, hematopoietic progenitors, etc.

IL-B50 is evaluated for agonist or antagonist activity on transfected cells expressing IL-7 receptor and controls. IL-B50 is evaluated for effect in macrophage/dendritic cell activation and antigen presentation assays, T cell cytokine production and proliferation in response to antigen or allogeneic stimulus. See, e.g., de Waal Malefyt et al. (1991) *J. Exp. Med.* 174:1209-1220; de Waal Malefyt et al. (1991) *J. Exp. Med.* 174:915-924; Fiorentino, et al. (1991) *J. Immunol.* 147, 3815-3822; Fiorentino, et al. (1991) *J. Immunol.* 146:3444-3451; and Groux, et al. (1996) *J. Exp. Med.* 184:19-29.

IL-B50 will also be evaluated for effects on NK cell stimulation. Assays may be based, e.g., on Hsu, et al. (1992) *Internat. Immunol.* 4:563-569; and Schwarz, et al. (1994) *J. Immunother.* 16:95-104. Other assays are applied to evaluate effects on cytotoxic T cells and LAK cells. See, e.g., Namien and Mire-Sluis (1998).

B cell growth and differentiation effects will be analyzed, e.g., by the methodology described, e.g., in Defrance, et al. (1992). *J. Exp. Med.* 175:671-682; Rousset, et al. (1992) *Proc. Nat'l Acad. Sci. USA* 89:1890-1893; including IgG2 and IgA2 switch factor assays. Note that, unlike COS7 supernatants, NIH3T3 and COP supernatants apparently do not interfere with human B cell assays.

C. Effects on the Expression of Cell Surface Molecules on Human Monocytes

Monocytes are purified by negative selection from peripheral blood mononuclear cells of normal healthy donors. Briefly, $3 \times 10^8$ ficoll banded mononuclear cells are incubated on ice with a cocktail of monoclonal antibodies (Becton-Dickinson; Mountain View, Calif.) consisting, e.g., of 200 µl of αCD2 (Leu-5A), 200 µl of αCD3 (Leu-4), 100 µl of αCD8 (Leu 2a), 100 µl of αCD19 (Leu-12), 100 µl of αCD20 (Leu-16), 100 µl of αCD56 (Leu-19), 100 µl of αCD67 (IOM 67; Immunotech, Westbrook, Me.), and anti-glycophorin antibody (10F7MN, ATCC, Rockville, Md.). Antibody bound cells are washed and then incubated with sheep anti-mouse IgG coupled magnetic beads (Dynal, Oslo, Norway) at a bead to cell ratio of 20:1. Antibody bound cells are separated from monocytes by application of a magnetic field. Subsequently, human monocytes are cultured in Yssel's medium (Gemini Bioproducts, Calabasas, Calif.) containing 1% human AB serum in the absence or presence of IL-B50, IL-6, G-CSF or combinations.

Analyses of the expression of cell surface molecules can be performed by direct immunofluorescence. For example, $2 \times 10^5$ purified human monocytes are incubated in phosphate buffered saline (PBS) containing 1% human serum on ice for 20 minutes. Cells are pelleted at 200×g. Cells are resuspended in 20 ml PE or FITC labeled mAb. Following an additional 20 minute incubation on ice, cells are washed in PBS containing 1% human serum followed by two washes in PBS alone. Cells are fixed in PBS containing 1% paraformaldehyde and analyzed on FACScan flow cytometer (Becton Dickinson; Mountain View, Calif.). Exemplary mAbs are used, e.g.: CD11b (anti-mac1), CD11c (a gp150/95), CD14 (Leu-M3), CD54 (Leu 54), CD80 (anti-BB1/B7), HLA-DR (L243) from Becton-Dickinson and CD86 (FUN 1; Pharmingen), CD64 (32.2; Medarex), CD40 (mAb89; Schering-Plough France).

D. Effects of IL-B50 on Cytokine Production by Human Monocytes

Human monocytes are isolated as described and cultured in Yssel's medium (Gemini Bioproducts, Calabasas, Calif.) containing 1% human AB serum in the absence or presence of IL-B50 (1/100 dilution baculovirus expressed material). In addition, monocytes are stimulated with LPS (*E. coli* 0127: B8 Difco) in the absence or presence of IL-B50 and the concentration of cytokines (IL-1β, IL-6, TNFα, GM-CSF, and IL-10) in the cell culture supernatant determined by ELISA.

For intracytoplasmic staining for cytokines, monocytes are cultured (1 million/ml) in Yssel's medium in the absence or presence of IL-B50 and LPS (*E. coli* 0127:B8 Difco) and 10 mg/ml Brefeldin A (Epicentre technologies Madison Wis.) for 12 hrs. Cells are washed in PBS and incubated in 2% formaldehyde/PBS solution for 20 minutes at RT. Subsequently cells are washed, resuspended in permeabilization buffer (0.5% saponin (Sigma) in PBS/BSA (0.5%)/Azide (1 mM)) and incubated for 20 minutes at RT. Cells ($2 \times 10^5$) are centrifuged and resuspended in 20 ml directly conjugated anti-cytokine mAbs diluted 1:10 in permeabilization buffer for 20 minutes at RT. The following antibodies can be used: IL-1α-PE (364-3B3-14); IL-6-PE (MQ2-13A5); TNFα-PE (MAb11); GM-CSF-PE (BVD2-21C11); and IL-12-PE (C11.5.14; Pharmingen San Diego, Calif.). Subsequently, cells are washed twice in permeabilization buffer and once in PBS/BSA/Azide and analyzed on FACScan flow cytometer (Becton Dickinson; Mountain View, Calif.).

IX. Generation and Analysis of Genetically Altered Animals

Transgenic mice can be generated by standard methods. Such animals are useful to determine the effects of deletion of the gene, in specific tissues, or completely throughout the organism. Such may provide interesting insight into development of the animal or particular tissues in various stages. Moreover, the effect on various responses to biological stress can be evaluated. See, e.g., Hogan, et al. (1995) *Manipulating the Mouse Embryo: A Laboratory Manual* (2d ed.) Cold Spring Harbor Laboratory Press.

All references cited herein are incorporated herein by reference to the same extent as if each individual publication or patent application was specifically and individually indicated to be incorporated by reference in its entirety for all purposes.

X. Biological Activity of IL-B50 and Complexes with IL-7Rα and Rδ2

A number of experiments were conducted in order to assess the signaling receptor complex for IL-B50, as well as the biological function of IL-B50. In the following examples, the term "human TSLP" or "hTSLP" is used interchangeably with the term IL-B50. Additionally, the term "human TSLPR" or "hTSLPR" is used interchangeably with the term Rδ2. Materials and methods used in the following experiments were as follows.

Cell lines. Human 293T epithelial cells were maintained in Dulbecco's modified Eagle's medium (DMEM) (Life Technologies Inc.) supplemented with 10% fetal calf serum (FCS) (LTBMC). The Pro-B cell line Ba/F3 was maintained in RPMI 1640 medium (Life Technologies Inc.) supplemented with 10% fetal calf serum and 10 ng/ml of mouse IL-3. QBI-293A human embryonic kidney cells used for adenovirus expression were grown in CMF-1 medium (CellWorks, San Diego, Calif.). BOSC23 cells were maintained in DMEM-10% FCS and guanine phosphoribosyltransferase (GPT) selection reagents (Specialty Media). The cells were transferred to Dulbecco's modified Eagle's medium-10% FCS without GPT selection reagents 2 days before transfection.

Adenovirus expression of human TSLP (IL-850) and purification of the recombinant protein. The mature coding region of human TSLP (residues 1-131 of SEQ ID NO: 2 or 4) was fused to the signal sequence of mouse SLAM (Bates, et al. (1999) *J. Immunol.* 163:1973) and inserted into a modified version of transfer vector pQB1-AdCMV5-GFP (Quantum Biotechnologies Inc.) by PCR. Recombinant adenovirus was produced as described in Quantum applications manual 24AL98. Recombinant virus was used to infect $5 \times 10^8$ cells in 1 L CMF-1 with culture in a Nunc Cell Factory (Nalge Nunc Int., Naperville, Ill.) for 3 days. The culture medium was clarified by centrifugation, dialyzed and filtered prior to application to a 5 ml Q-Sepharose column. The Q-Sepharose flow-through, which contained human TSLP, was loaded onto a 5 ml HiTrap Heparin (Pharmacia, Uppsala, Sweden) column at 5 ml/min. The column was washed with 50 mM Tris-HCl pH 8.0, 1 mM EDTA, and eluted with a gradient from 0-2.5 M NaCl in 50 mM Tris-HCl pH 8.0, 1 mM EDTA. The peak fractions were concentrated, dialyzed against PBS and quantitated by SDS-PAGE and Coomassie staining using lysozyme as a standard. A similar procedure was followed to prepare mouse TSLP.

Ba/F3 retroviral-mediated gene transfer and proliferation assays. Human IL-7Rα cDNA and human TSLPR cDNA were cloned by PCR in the retroviral vectors pMX and its derivative pMX-puro to give pMX-hIL-7Rα and pMX-puro-TSLPR, respectively (Kitamura, T. (1998) *Int. J. Hematol.* 67:351). The BOSC23 packaging cell line was transiently transfected with retrovirus constructs using Fugene 6

(GIBCO BRL) according to the manufacturer protocol. Retrovirus containing supernatants were collected after two days. Ba/F3 cells were infected with retroviral supernatants for 48 hr on petri dishes coated with 40 μg/ml recombinant fibronectin fragments (Retronectin, Takara). After 48 hr puromycine (1 μg/ml) was added to those cells infected with virus obtained from pMX-puro constructs. The efficiency of infection of Ba/F3 cells was over 90% as assessed by parallel infection with the test construct pMXI-EGFP encoding the enhanced green fluorescent protein (EGFP). Proliferation assays using Ba/F cells were as previously described (Ho, et al. (1993) *Proc. Natl. Acad. Sci. USA* 90:11267). Cells were washed three times with RPMI media and plated at a density of 5000 cells/well. Cells were grown with serial threefold dilutions of mouse IL-3, human and mouse TSLP, or human IL-7 (all starting concentrations 225 ng/ml). After 36 hr at 37 degrees C. Alamar Blue® REDOX indicator (Trek Diagnostic systems) was added to a final concentration of 10% (vol/vol) to each well. Cells were allowed to grow for 5-8 more hours after which plates were measured with a fluorometer.

Quantitation of mRNA expression. cDNA libraries from various tissues and cellular sources were prepared as described previously (Bolin, et al. (1997) *J. Neurosci.* 17:5493) and used as templates for Taqman-PCR analyses. cDNAs (50 ng per reaction) were analyzed for the expression of hTSLP, hTSLPR and hIL7Rα genes by the Fluorogenic 5'-nuclease PCR assay (Holland, et al. (1991) *Proc. Natl. Acad. Sci. USA* 88:7276), using an ABI Prism 7700 Sequence Detection System (Perkin Elmer, Foster City, Calif.). Reactions were incubated for 2 min at 50 degrees C., denatured for 10 min at 95 degrees C. and subjected to 40 two-step amplification cycles with annealing/extension at 60 degrees C. for 1 min followed by denaturation at 95 degrees C. for 15 sec. The amplicons used for hTSLP, hTSLPR and IL-7Rα covered by 246-315, by 263-335 and by 519-596, respectively (numbering starts at start codon), and were analyzed with FAM-labeled probes. Values were expressed as fg/50 ng total cDNA. Primers and probes for human chemokine and chemokine receptors were obtained from Perkin-Elmer as PreDeveloped Assay Reagents (PDAR's). Chemokine and chemokine receptor expression was adjusted for the amount of 18SrRNA and compared to the control (calibrator) samples using the comparative $C_T$ method (Fehniger, et al. (1999) *J. Immunol.* 162:4511). Samples were measured in duplicate. 18SrRNA levels were determined under primer limited conditions in multiplex reactions as recommended using a Vic labelled probe (Perkin Elmer, Foster City, Calif.).

Cell isolation and culture. Peripheral Blood Mononuclear Cells (PBMC) were purified from buffy coats of healthy volunteers (Stanford Blood Bank, Palo Alto, Calif.) by centrifugation over Ficoll. Human monocytes were isolated from PBMC by negative depletion using anti-CD2 (Leu-5A), anti-CD3 (Leu-4), anti-CD8 (Leu 2a), anti-CD19 (Leu-12), anti-CD20 (Leu-16), anti-CD56 (Leu-19), (BD, San Jose Calif.), anti-CD67 (10M 67) (Immunotech, Westbrook, Me.) and anti-glycophorin A (10F7MN, ATCC, Rockville, Md.) mAbs and sheep anti-mouse IgG coupled magnetic beads (Dynal, Oslo, Norway) as described previously (Koppelman, et al. (1997) *Immunity* 7:861). Monocytes were cultured in RPMI+ 10% FCS at a density of $10^6$ cells/ml in the presence or absence of IL-7 (50 ng/ml) and/or hTSLP (50 ng/ml) for 24 hrs and culture supernatants and cells were harvested for quantitation of cytokine production or gene expression analyses. Human CD11c+ dendritic cells (DC) were isolated from PBMC as previously described (Kadowaki, et al. (2000) *J. Exp. Med.* 192:219). Briefly, PBMC were incubated with anti-CD3, anti-CD14, anti-CD19, anti-CD56 mAbs, depleted from lineage+ cells using magnetic beads (Dynal) and CD11c+ Lineage-blood DC were subsequently isolated by cell sorting to reach a purity of more than 99%. Freshly sorted cells were cultured in RPMI1640 containing 10% FCS at $5 \times 10^4/100$ μl in flat-bottom 96-well half-area culture plates or at $1 \times 10^5/200$ μl in flat-bottom 96-well plates, with or without IL-B50 (15 ng/ml).

TARC Elisa. The production of TARC/CCL17 in culture supernatants was determined by chemokine specific elisa using MAB364 as capture reagent and BAF364 as detection reagent (R&D Systems, Minneapolis Minn.). The sensitivity of the assay was 50 pg/ml.

DC viability and flow cytometric analysis. After 24 hours of culture, DC were harvested and resuspended in an EDTA-containing medium to dissociate the clusters. Viable DC were first counted using trypan blue exclusion of dead cells. Remaining cells were stained with a variety of mouse anti-human FITC-conjugated monoclonal antibodies (mAb) including anti-HLA-DR (Becton Dickinson), anti-CD40, anti-CD80 and CD86 (all from Pharmingen) or an Ig-G1 isotype control (Becton Dickinson), and were analyzed with a FACScan® flow cytometer (Becton Dickinson). Dead cells were excluded based on side and forward scatter characteristics.

T cell proliferation assay. Naïve CD4+/CD45RA+ T cells were isolated from adult blood buffy coats by negative depletion of cells expressing CD14, CD19, CD56, CD8, CD45RO, HLA-DR and glycophorin A using magnetic beads (Dynal). More than 95% of the purified cells had the CD4+ CD45RA+ naïve T cell phenotype. CD11c+ DC were washed twice to remove any cytokine and co-cultured with $5 \times 10^4$ allogeneic naïve CD4+ T cells in round-bottom 96-well culture plates at increasing DC/T cell ratios. All co-cultures were carried out in triplicate. DC alone and T cells alone were used as controls. After 5 days, cells were pulsed with 1 μCi $^3$H-Thymidine (Amersham) for 16 hours before harvesting and counting radioactivity.

Stat3 and Stat5 activation assays. Stable Ba/F3 transfectant cells (~$2.5 \times 10^7$ cells) were starved for 4-6 hours, and then stimulated at $10^6$ cells/ml for 15 min with either 10 ng/ml of mIL-3 or 30 ng/ml of hTSLP. After stimulation, cells were harvested and incubated for 15 min at 4 degrees C. in lysis buffer containing 50 mM Tris-HCL pH 7.5, 300 mM NaCl, 2 mM EDTA, 0.875% Brij 97, 0.125% NP40, 10 mg/ml aprotinin, 10 mg/ml leupeptin, 1 mM PMSF, 1 mM Na3VO4, and 1 mM NaF. Cell lysates were clarified by centrifugation at 12,000×g for 15 min, and supernatants were subjected to 8% SDS-PAGE. Proteins were electrotransferred onto nylon membranes (Immobilon-P, Millipore, Bradford, Mass.) and detected by Western Blot analysis using rabbit Abs against anti-phospho Stat3 and anti-phospho Stat5 (New England Biolabs) or anti-Stat3 and anti-Stat5 (Santa Cruz Biotechnology), followed by mouse anti-rabbit Ig HRP. Immunoreactive bands were visualized with enhanced chemiluminescence (ECL) (SuperSignal West Dura Extended Duration Substrate, Pierce, Rockford, Ill.) on ECL film (Kodak). For reprobing, blots were stripped with 200 mM glycine, 1% SDS, pH 2.5 for 30 min at 65 degrees C.

A. IL-B50 Signals Via IL-7Rα and Rδ2

The cytokine human IL-B50 has as closest homologs human and mouse IL-7 and the recently described mouse TSLP (Sims, et al. (2000) *J. Expt'l Med.* 192:671-680). In mouse, both IL-7 and TSLP function as T- and B-cell growth and differentiation factors. The signaling receptor complexes for mouse IL-7 and mouse TSLP consist of two subunits, respectively mouse IL-7Rα and mouse Rγc (common receptor for IL-2, IL-4, IL-7, IL-9, and IL-15) for mouse IL-7, and mouse IL-7Rα and mouse TSLPR(Rδ1) for the mTSLP ligand (Park, et al. (2000) *J. Expt'l Med.* 192:659-670).

In an attempt to identify the signaling receptor complex for human IL-B50, Ba/F3 cells were co-transfected with expression constructs for human IL-7Rα and an orphan human cytokine receptor known as Rδ2, a subunit related to Rγc and mTSLPR (Rδ1), using the methods described above. Any functional relationship between the mTSLPR subunit Rδ1 and the human Rδ2 had been unclear. Co-transfected Ba/F3 cells showed a proliferative response in the presence of hIL-B50, but not with hIL-7 or medium. Ba/F3 cells transfected with either hIL-7Rα or hRδ2 alone did not show a proliferative response with hIL-B50. Additionally, no cross-reactivity between mTSLP and the hTSLP receptor complex was observed. These findings establish the signaling complex for human IL-B50 as consisting of hIL-7Rα and hRδ2.

The corresponding activation status of Stat5 and Stat3 was also measured in the various BaF3 cell populations. Both Stat5 and Stat3 were phosphorylated upon addition of hTSLP, but only when both hTSLPR and hIL-7Rα was present B. Expression Analysis of IL-B50, hIL-7Rα and hRδ2

Figure 2E:
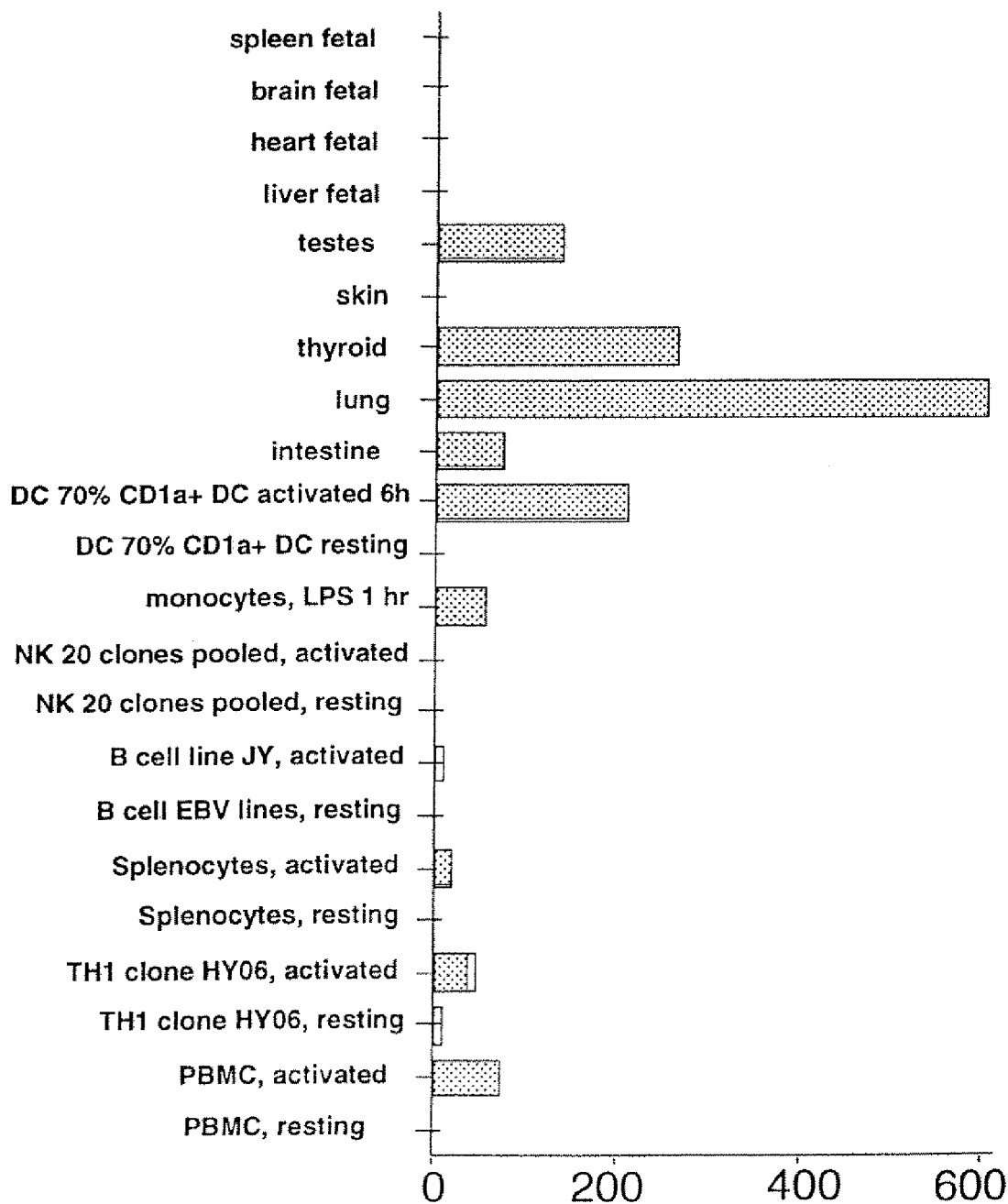

In order to identify target cells capable of responding to IL-B50, a large panel of cDNA libraries was analyzed for the simultaneous expression of both hIL-7Rα and hRδ2, using quatitative PCR. Results of the expression analysis, conducted as described in materials and methods, are presented in FIGS. 2A-2E. In particular, expression analysis of the two receptor subunits indicated that they were co-expressed primarily in activated dendritic cells, monocytes, and T cells (see, FIGS. 2A-2D) indicating that these cell types respond to human IL-B50. As shown in FIG. 2E, IL-B50 was expressed in various tissue types, with high expression in the human lung.

C. Human IL-B50 Induces Chemokine Expression on Freshly Isolated Monocyte Population and CD11c+ Blood DC The spectrum of biological activities induced by IL-B50 was investigated based on the overlapping expression patterns of IL-B50 receptor components. cDNA was prepared from human monocytes cultured for 24 hrs in the presence of IL-B50 or IL-7, and the expression of 38 human chemokines and 20 human chemokine receptors were analyzed by quantitative "real time" PCR. Interestingly, IL-B50 (TSLP) and IL-7 influenced the expression of distinct sets of chemokines (Table 1), but did not affect the expression of chemokine receptors. IL-B50 enhanced the expression of TARC/CCL17, DC-CK1/PARC/CCL18, MDC/CCL22, and MIP3β/CL19. IL-7 also enhanced expression of TARC/CCL17, MDC/CCL22, and MIP3β/CCL19 but in addition, enhanced expression of IL-8/CXCL8, CTAPIII/CXCL7, ENA78/CXCL5, and GROabg/CXCL123 and decreased the expression levels of IP-10/CXCL10, I-TACK/CXCL11, SDF1/CXCL12, MCP2/CCL8 and MCP4/CCL13 (Table 1).

Figure 12A:
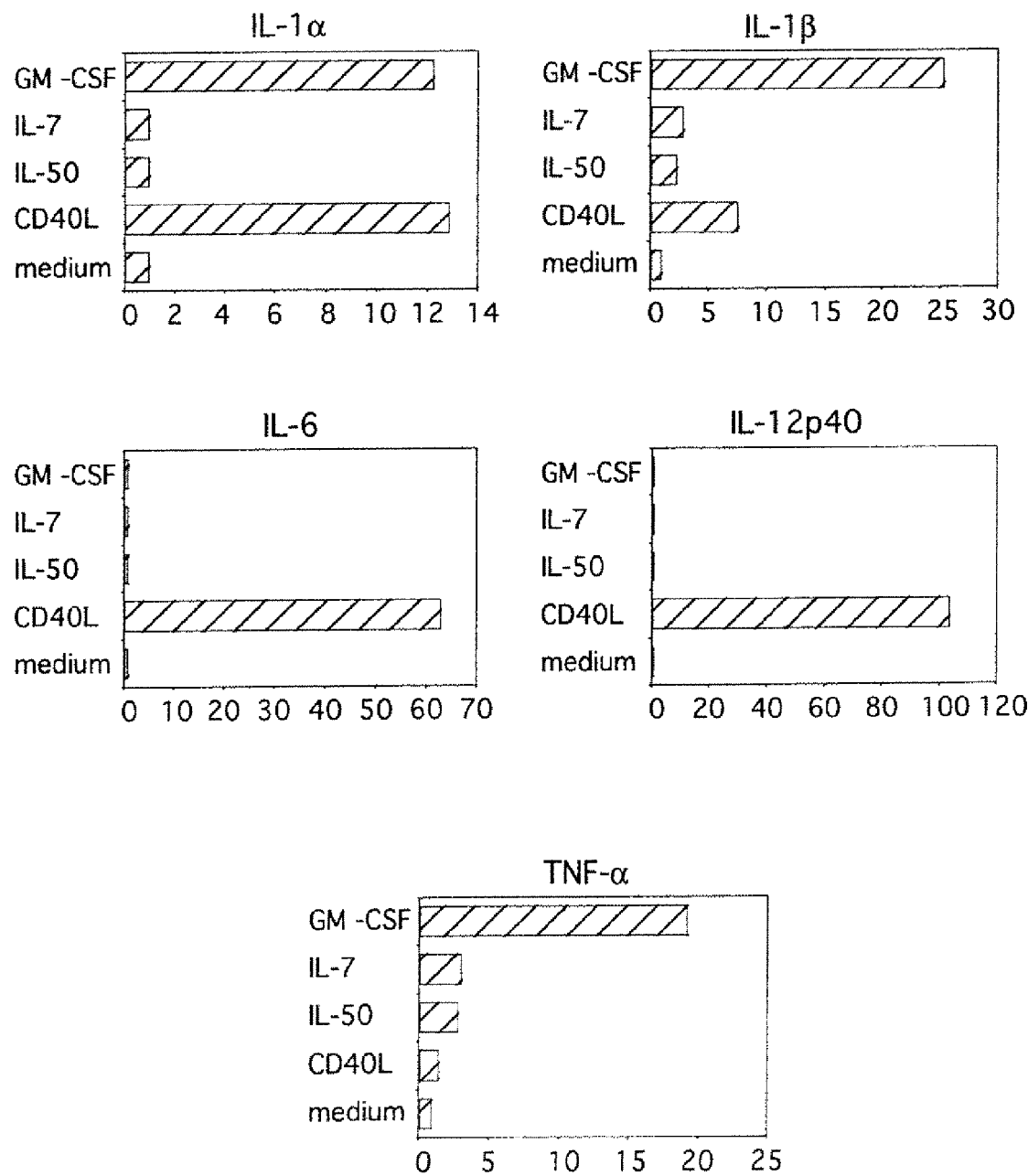
Figure 13:
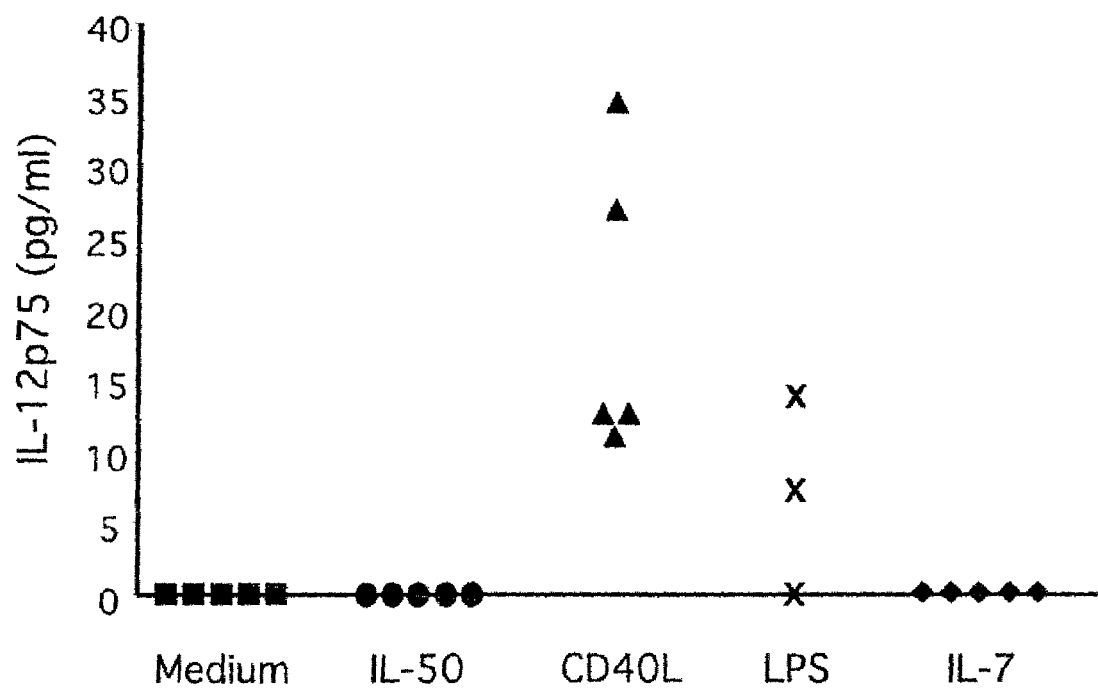
FIG. 13 shows the effect of IL-B50 on the induction of IL12p75 protein.

Additionally, the ability of IL-B50 to stimulate DCs to produce mRNAs for various cytokines and chemokines was compared with that of GM-CSF, IL-7, CD40-ligand (CD40L) and medium alone as a control, as follows. Purified CD11c+ DCs were cultured for 15-17 hours with IL-B50 (15 ng/ml), GM-CSF (100 ng/ml), IL-7 (50 ng/ml), CD40-ligand transfected L-cells (1 L-cell/4 DC) or medium alone. Total RNA was extracted and studied using real time quantitative PCR as described above. As shown in FIGS. 12A and 12C, IL-B50 did not stimulate human DCs to produce mRNA for IL-1α, IL-1β, IL-6, IL-12p40, TNF-α, MCP-1, MCP-4, Rantes and MIG, but did stimulate human DCs to produde mRNA for the chemokines TARC, MDC and MIP3-13 (FIG. 12B).

Figure 3:
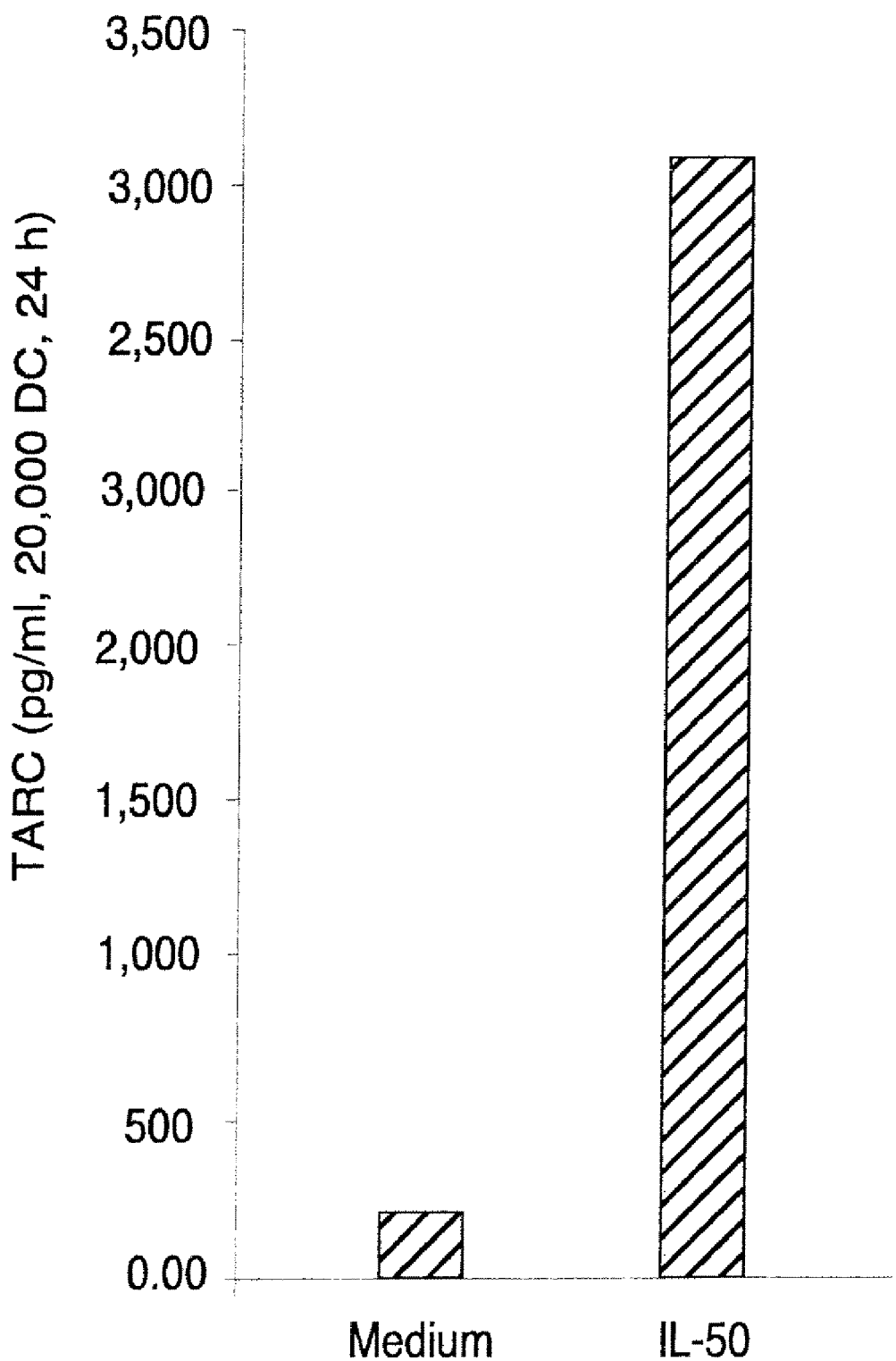
FIG. 3 shows the induction of TARC by IL-B50. Human CD11c+ DC were cultured in the absence or the presence of IL-B50 (50 ng/ml) and the production of TARC was determined in the culture supernatant by ELISA.

The induction of TARC protein by IL-B50 on monocyte and dendritic cell populations was confirmed by ELISA. The level of TARC production by CD11c+ dendritic cells was at least ten-fold higher than that of monocytes (FIG. 3).

Figure 11:
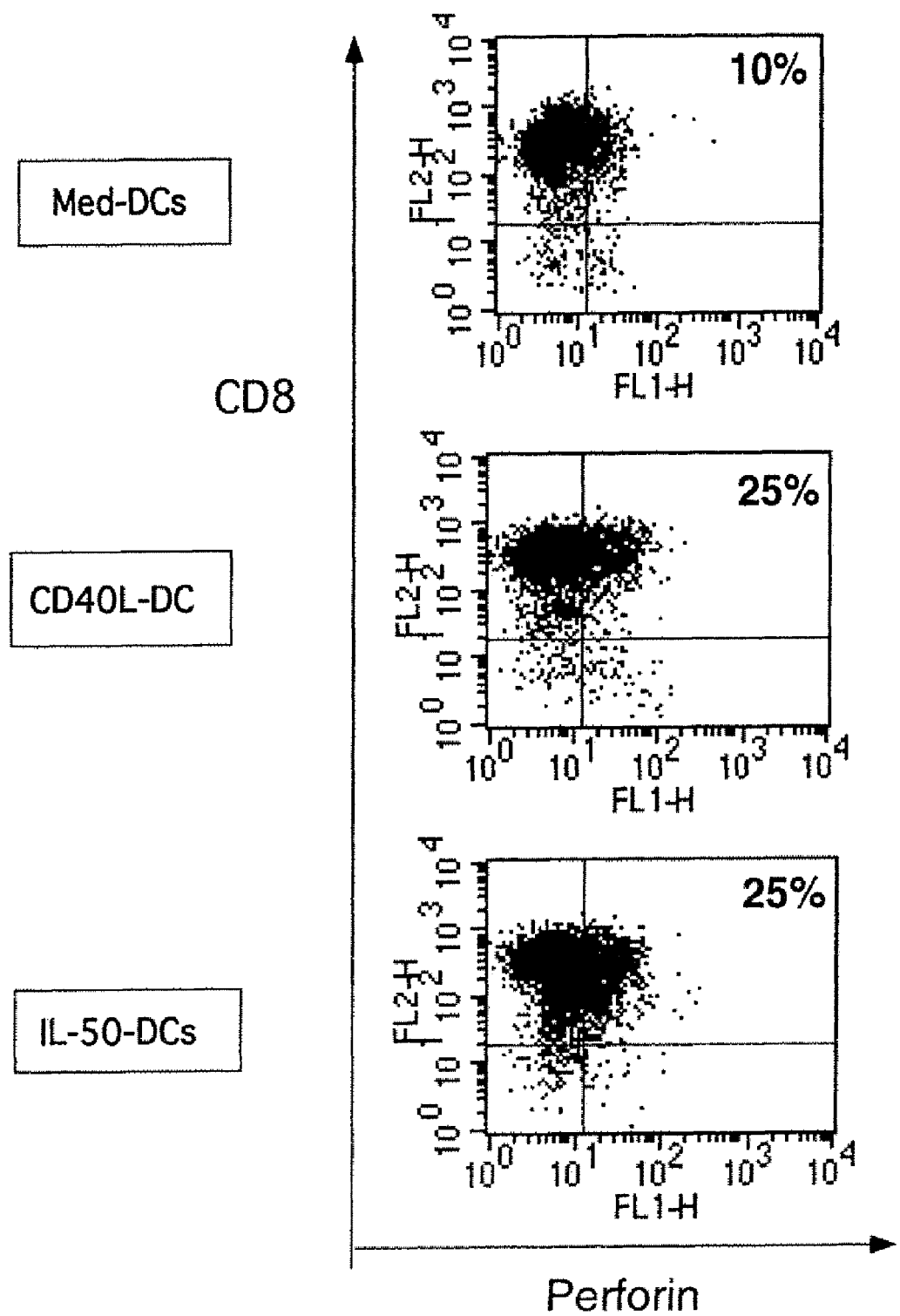
FIG. 11 compares expression of perforin by human naïve CD8 T cells induced by DCs treated with medium alone, IL-B50 or CD40-ligand.

The induction of IL12p75 protein by IL-B50 was also examined. To do so, purified CD11c+ DCs were culture for 24 hours with IL-B50 (15 ng/ml), IL-7 (50 ng/ml), CD40-ligand-transfected L-cells (1 L-cell/4 DC), bacterial lipopolysaccharide (LPS: 1 mg/ml) or medium alone. Culture supernatant was harvested and bioactive IL12p75 was measured using a high-sensitivity ELISA kit. As shown in FIG. 11, IL-B50 did not stimulate human DCs to produce IL12p75 protein.

TABLE 1

Effects of IL-B50 and IL-7 on Chemokine Expression*

| Chemokine | Media | IL-B50 | IL-7 |
|---|---|---|---|
| CCL1 | 40.0 | 1.0 | 1.4 |
| CCL2 | 24.8 | 1.0 | 1.5 |
| CCL3 | 31.5 | 0.7 | 2.0 |
| CCL4 | 28.9 | 1.0 | 1.6 |
| CCL5 | 30.4 | 1.1 | 0.6 |
| CCL7 | 31.3 | 0.7 | 1.4 |
| CCL8 | 30.2 | 0.8 | 0.2 |
| CCL11 | 40.0 | 1.6 | 1.4 |
| CCL13 | 37.3 | 1.6 | 0.1 |
| CCL14 | 40.0 | 1.3 | 1.3 |
| CCL15 | 40.0 | 1.1 | 1.3 |
| CCL16 | 40.0 | 2.2 | 7.0 |
| CCL17 | 39.8 | 195.4 | 20.1 |
| CCL18 | 35.8 | 2.9 | 1.7 |
| CCL19 | 36.7 | 8.5 | 8.3 |
| CCL20 | 40.0 | 1.2 | 1.2 |
| CCL21 | 40.0 | 1.0 | 1.0 |
| CCL22 | 34.3 | 8.8 | 3.0 |
| CCL24 | 29.3 | 2.0 | 1.2 |
| CCL25 | 40.0 | 1.1 | 1.1 |
| CCL26 | 38.9 | 1.1 | 2.5 |
| CCL27 | 40.0 | 0.8 | 1.2 |
| CCL28 | 40.0 | 1.0 | 1.0 |
| CXCL1-3 | 28.7 | 1.0 | 4.4 |
| CXCL4 | 27.9 | 1.2 | 1.9 |
| CXCL5 | 28.7 | 1.1 | 8.0 |
| CXCL6 | 40.0 | 1.5 | 1.3 |
| CXCL7 | 28.7 | 1.1 | 2.0 |
| CXCL8 | 27.3 | 1.4 | 8.5 |
| CXCL9 | 34.9 | 0.6 | 0.7 |
| CXCL10 | 29.7 | 0.6 | 0.1 |
| CXCL11 | 32.9 | 0.7 | 0.0 |
| CXCL12 | 33.1 | 0.6 | 0.2 |
| CXCL13 | 35.4 | 0.2 | 0.8 |
| CXCL14 | 39.7 | 1.0 | 1.0 |
| XCL1 | 40.0 | 0.9 | 3.8 |
| CX3CL1 | 40.0 | 1.4 | 1.3 |

*Human monocytes were cultured in the absence or presence of IL-B50 (50 ng/ml) or IL-7 (50 ng/ml) for 18 h, and expression of chemokine genes was determined by quantitative PCR. Results are expressed as 1) $C_T$ values of nonactivated samples and 2) fold difference relative to the calibrator sample (media).

D. IL-B50 Activates CD11c+ Dendritic Cells.

Figure 4A:
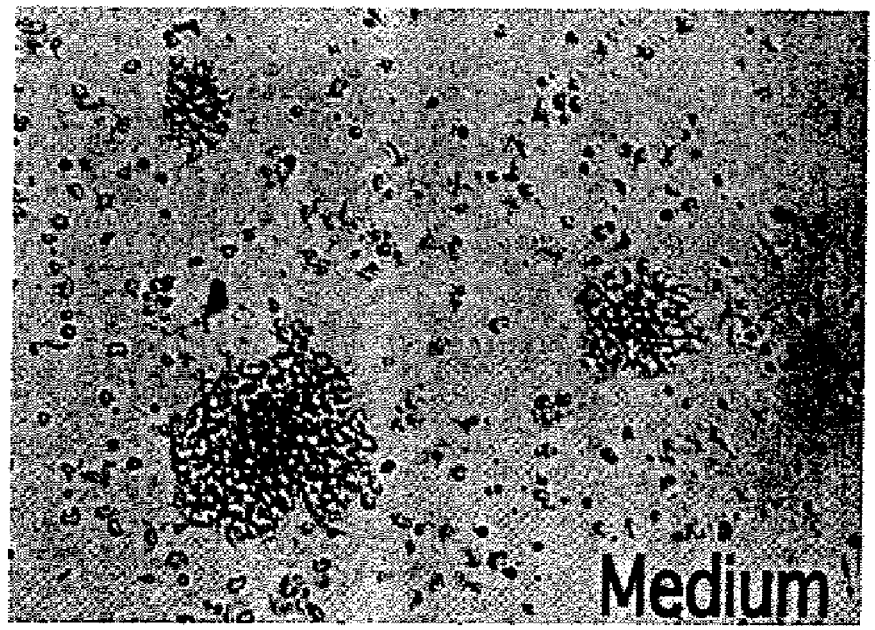
FIG. 4A depicts a culture of sorted CD11c+ DC after 24 h in medium alone. DC form small and irregular clumps with a dark center, indicating the presence of dying cells.
Figure 4B:
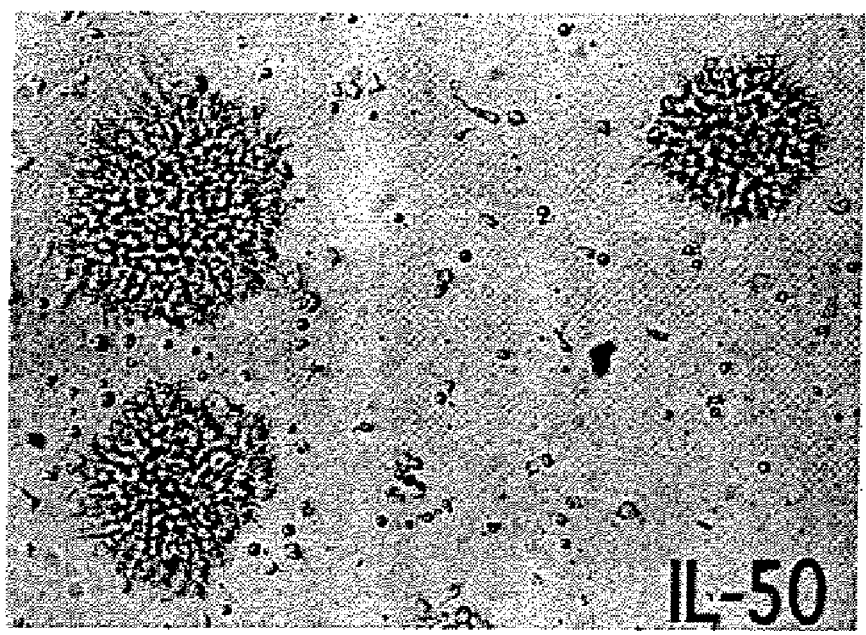
FIG. 4B depicts a culture of sorted CD11c+ DC from the same donor as in FIG. 4A, treated with 15 ng/ml of IL-B50. DC form larger and round clumps with fine dendrites visible at the periphery, indicating the maturation of the DC.
Figure 5:
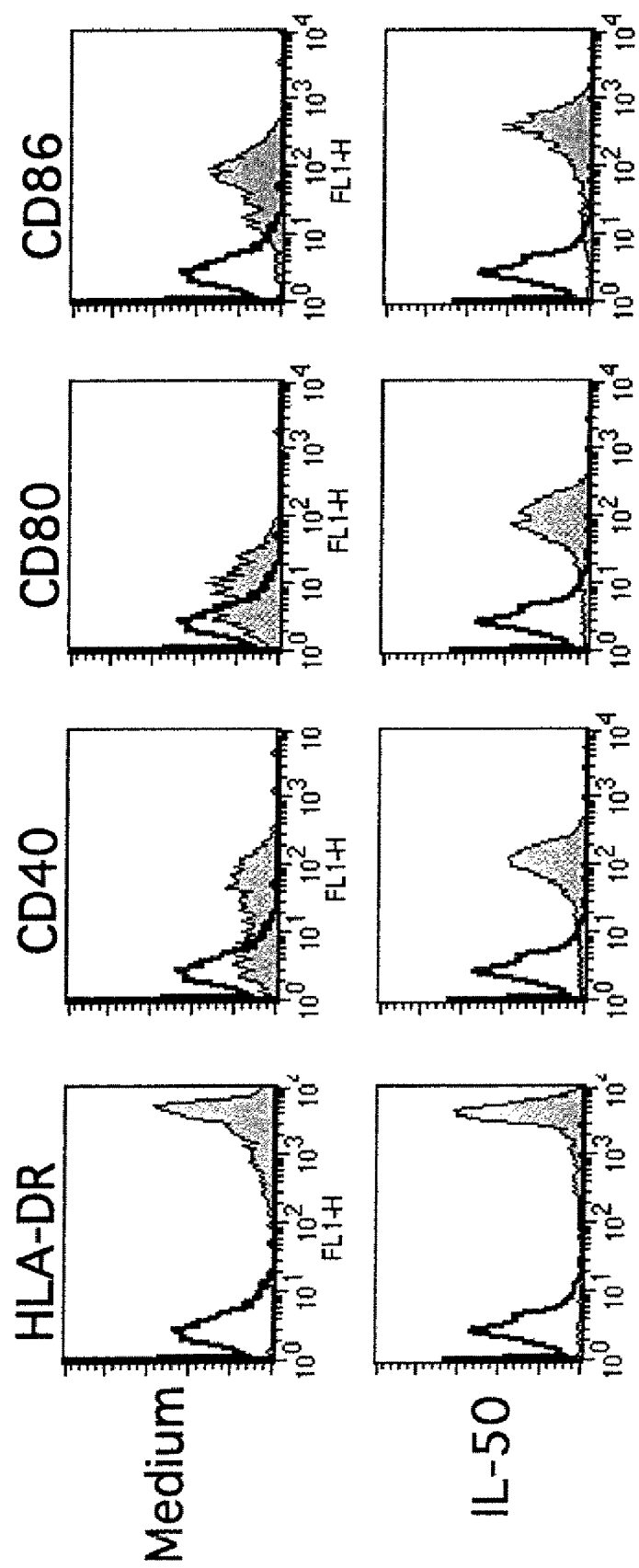
FIG. 5 shows the surface phenotype of CD11c+ DC after 24 h of culture with and without (medium alone) IL-B50 and shows the upregulation of HLA-DR, as well as the costimulatory molecules CD40, CD80 and CD86. Results shown are from one representative of four independent experiments.
Figure 6B:
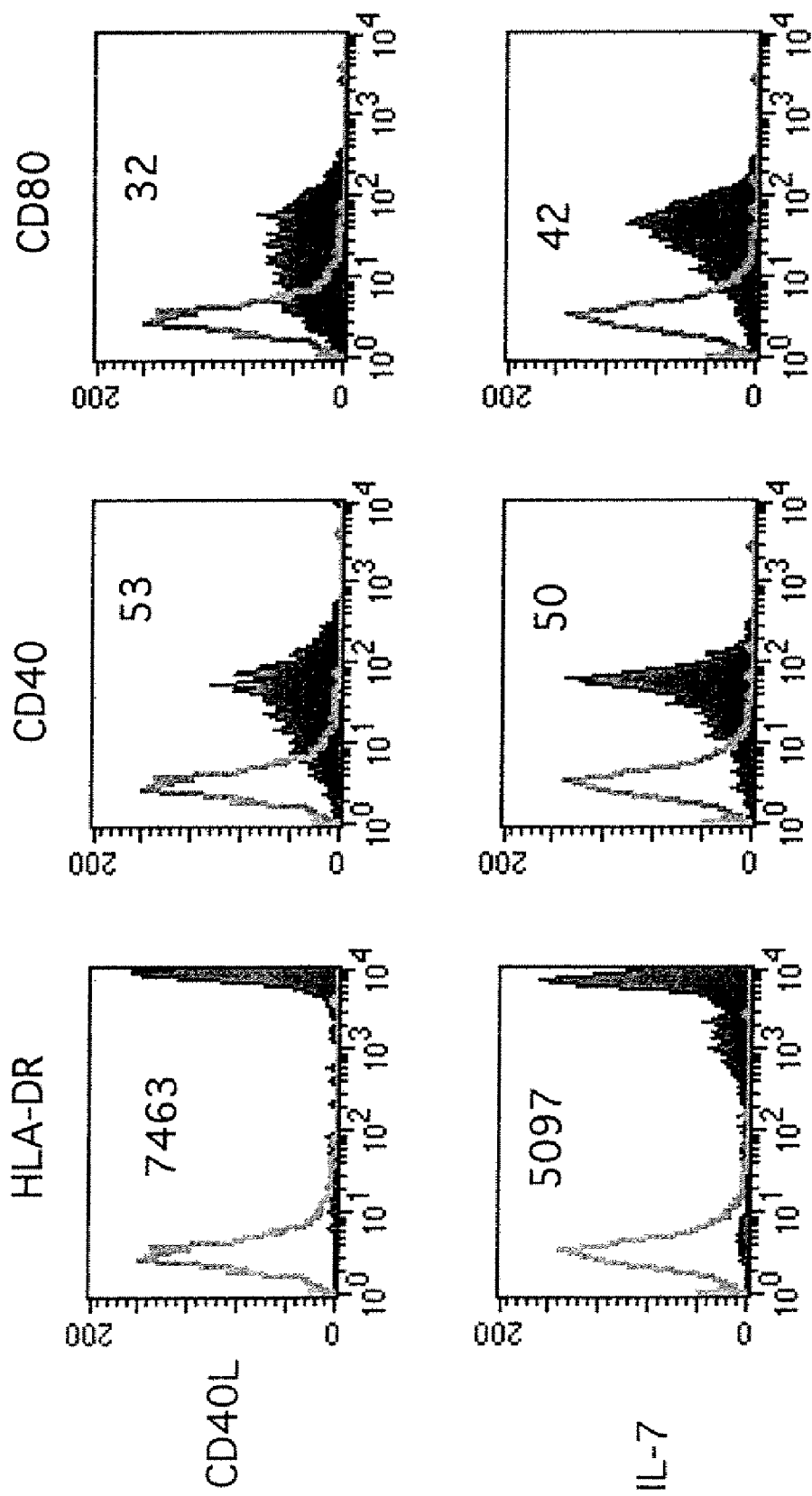
Figure 6C:
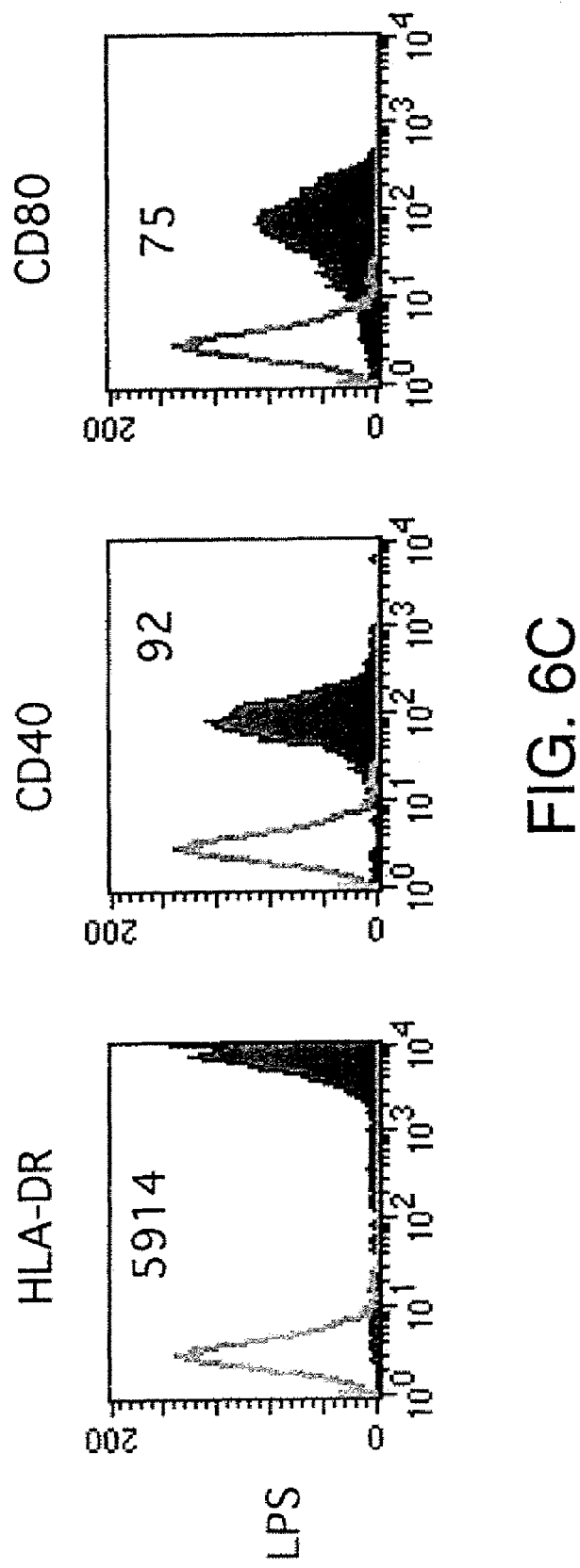

Freshly purified immature CD11c+ blood DC are known to spontaneously mature in culture. As shown in FIG. 4A, loose and irregular clumps in the DC culture were evident after 24 hrs in medium alone. In the presence of IL-B50, this maturation process was dramatically enhanced. DC in culture formed tight and round clumps with fine dendrites visible at the periphery of each clump (FIG. 4B). The IL-B50-induced maturation was confirmed by analyzing the surface phenotype of DC using flow cytometry. Whereas IL-B50 slightly upregulated the expression of HLA-DR and CD86, it strongly induced the costimulatory molecules CD40 and CD80 (FIG. 5). This maturation process was accompanied by an increased viability of the DC. Additionally, IL-B50 was more potent than CD40-ligand (CD40L) and IL-7 in upregulating CD40 and CD80 (FIGS. 6A-6C). A titration of IL-B50 using log dilutions of the cytokine showed that both the effect on survival and the induction of costimulatory molecules on DC was maximal at 15 ng/ml and above, and still significant at concentrations as low as 15 pg/ml.

Figure 7:
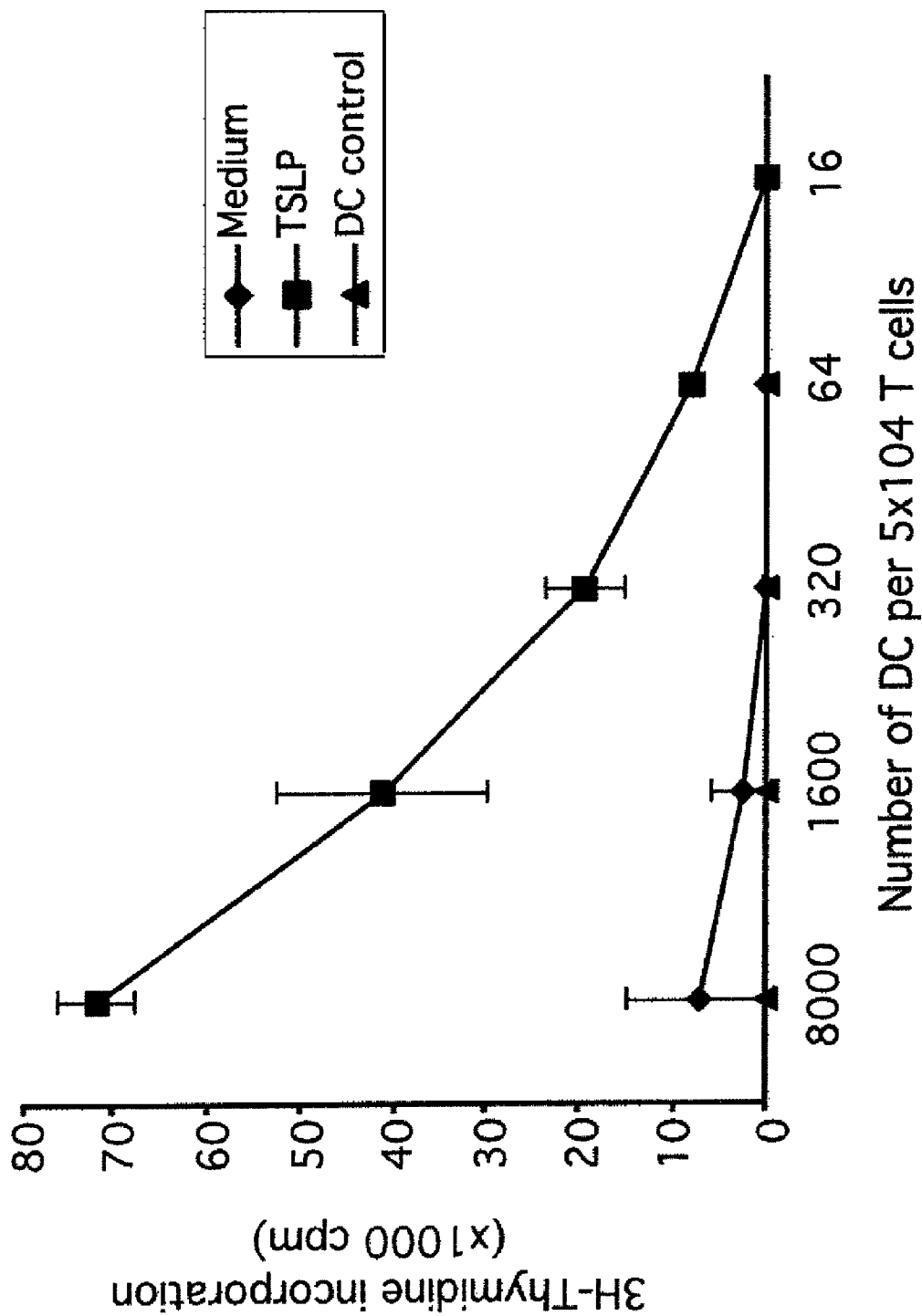
FIG. 7 shows the results of a T cell proliferation assay using CD11c+ DC matured for 24 h in medium or with IL-B50 (15 ng/ml) and cocultured with 5×10$^4$ allogenic CD4+ CD45RA+ naïve T cells at increasing DC/T cell ratios. Proliferation was assessed on day 6 by measuring [$^3$H]thymidine incorporation. Each point represents the mean [$^3$H]thymidine incorporation of triplicate cocultures. Vertical bars indicate the SD. DC alone (▲) were used as a control and did not significantly proliferate. Results shown are from one representative of the two independent experiments.

The T cell stimulatory capacity of CD11+ DC, cultured 24 hrs in medium alone or in the presence of IL-B50, was analyzed. DCs were cocultured with $5 \times 10^4$ naïve CD4+ CD45RA+ allogeneic T cells at increasing DC/T cell ratios. As assessed by $^3$H-thymidine incorporation at day 5 of the coculture, DC cultured with IL-B50 induced up to 10-fold stronger naïve T cell proliferation as compared to DC cultured in medium (FIG. 7).

Figure 8:
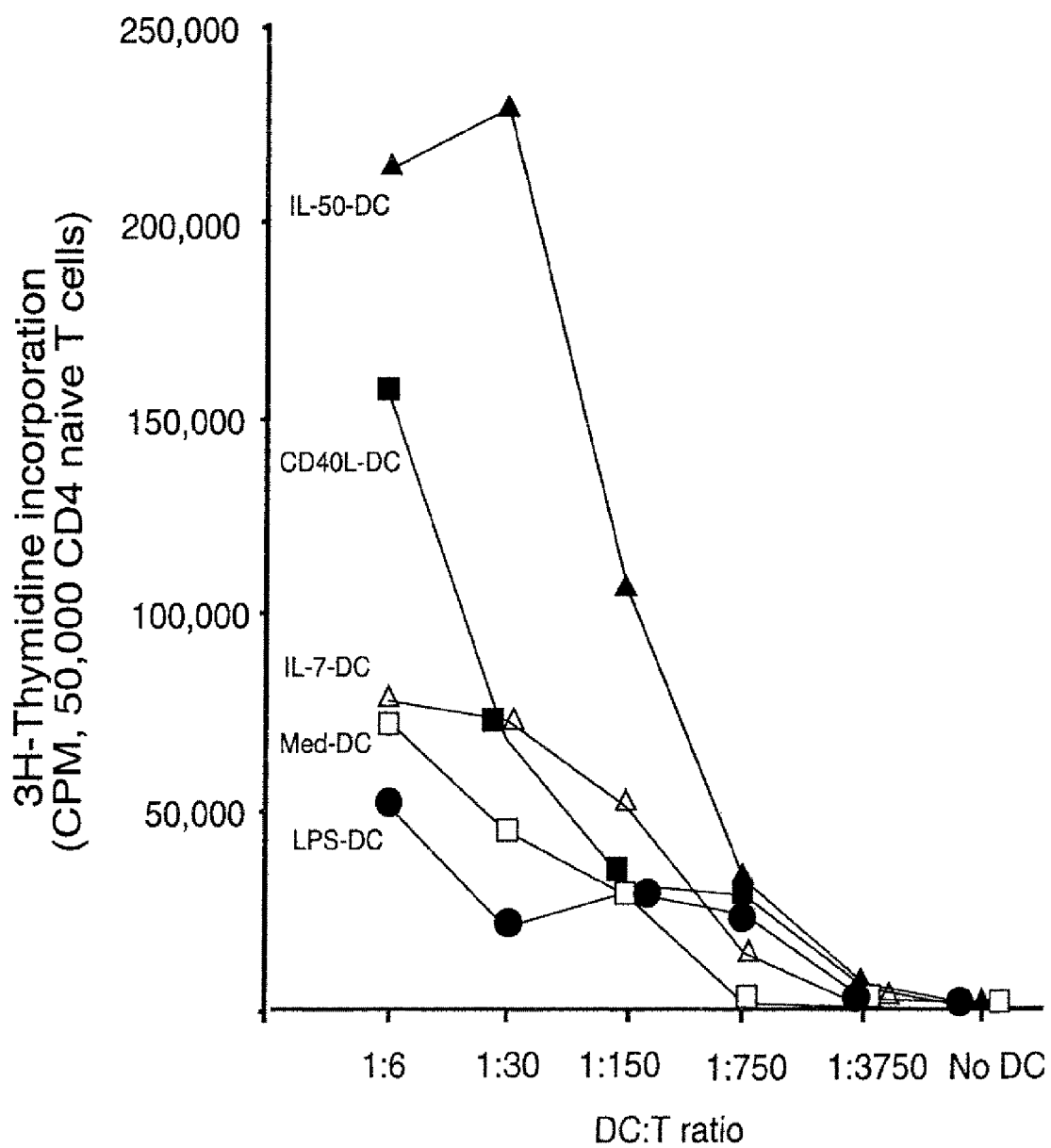
FIG. 8 shows the results of a similar experiment as described for FIG. 9, using DC matured in medium, IL-B50, CD40-ligand (CD40L), IL-7 and LPS.
Figure 9A:
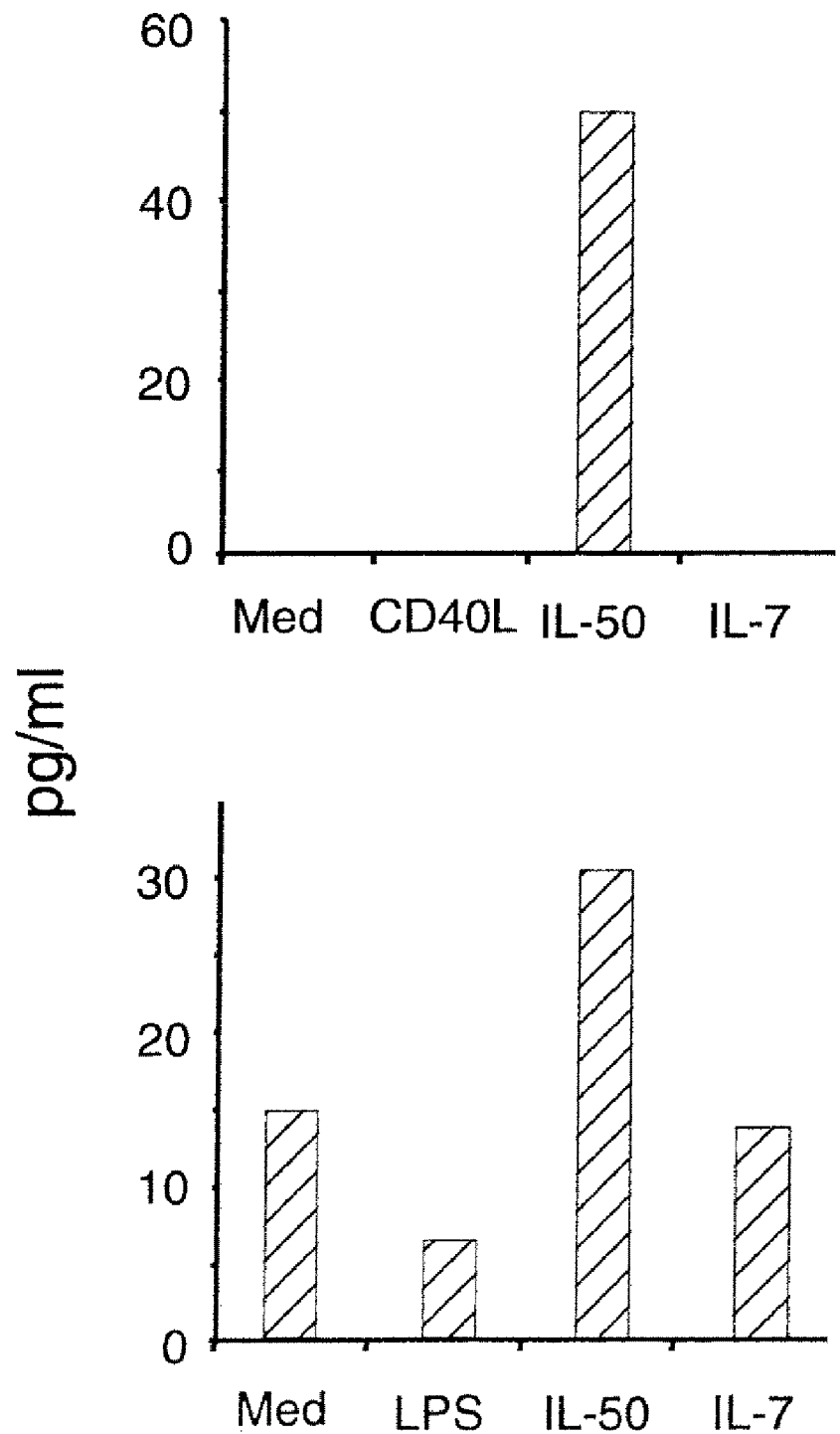
Figure 9C:
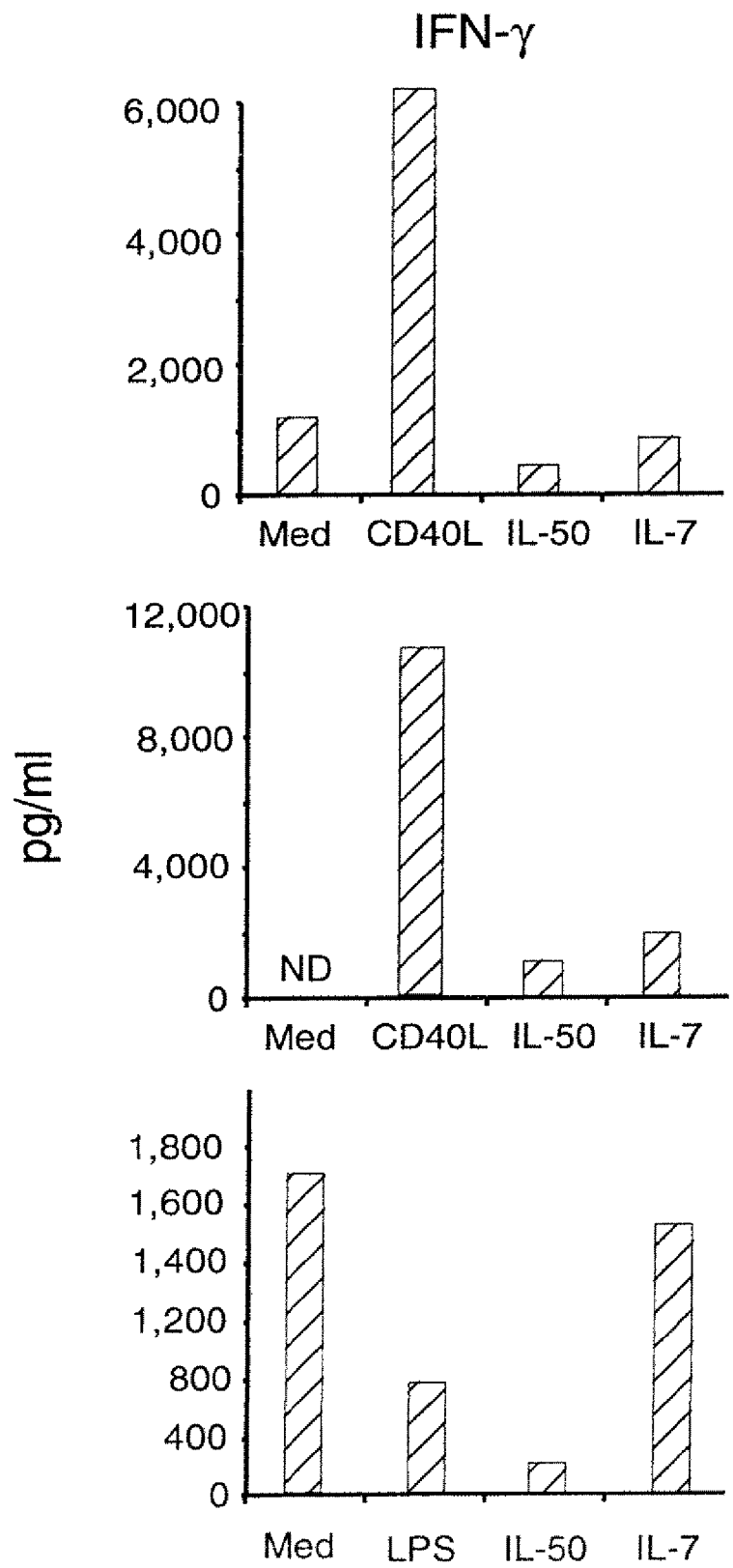
Figure 9E:
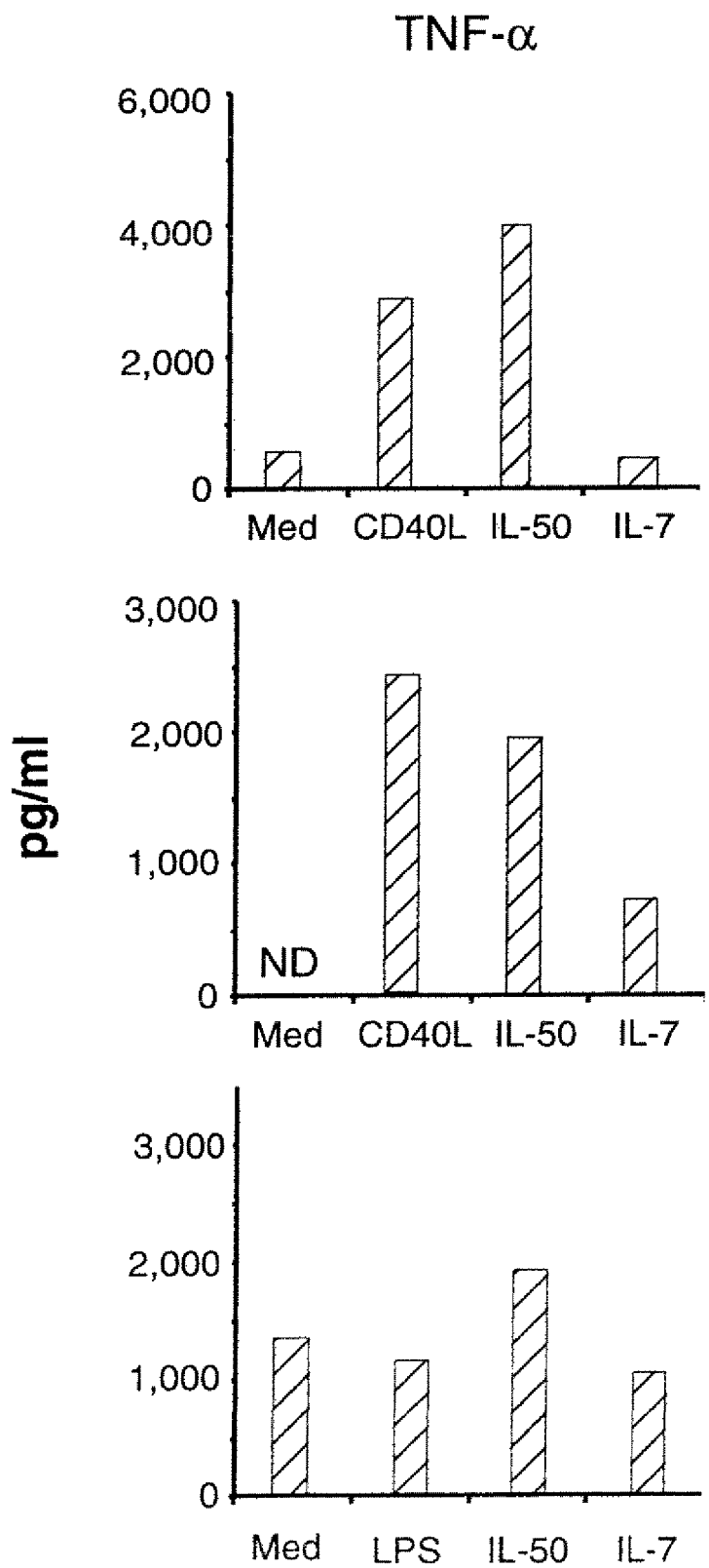

Additionally, the T cell stimulatory capacity of CD11+DC, cultured with LPS, medium alone, IL-7, CD40-ligand and IL-B50, was compared by determining $^3$H-thymidine incorporation. As shown in FIG. 8, IL-B50-activated DCs were more potent than DCs activated with CD40-ligand, IL-7 and LPS in inducing proliferation of allogeneic naïve CD4 T cells.

DCs, cultured in medium alone, IL-B50, CD40-ligand, IL-7 and LPS, were cocultured with naïve CD4 T cells. After 6 days of coculture, CD4 T cells were restimulated for 24 hours with anti-CD3 and anti-CD28 and the culture supernatants were analyzed by ELISA to quantify the cytokine production by T cells. As shown in FIGS. 9A-9E, IL-B50-activated human DCs primed naïve CD4 T cells to produce IL-4, IL-13 and TNF-α, but inhibited production of IL-10 and IFN-γ.

Figure 10:
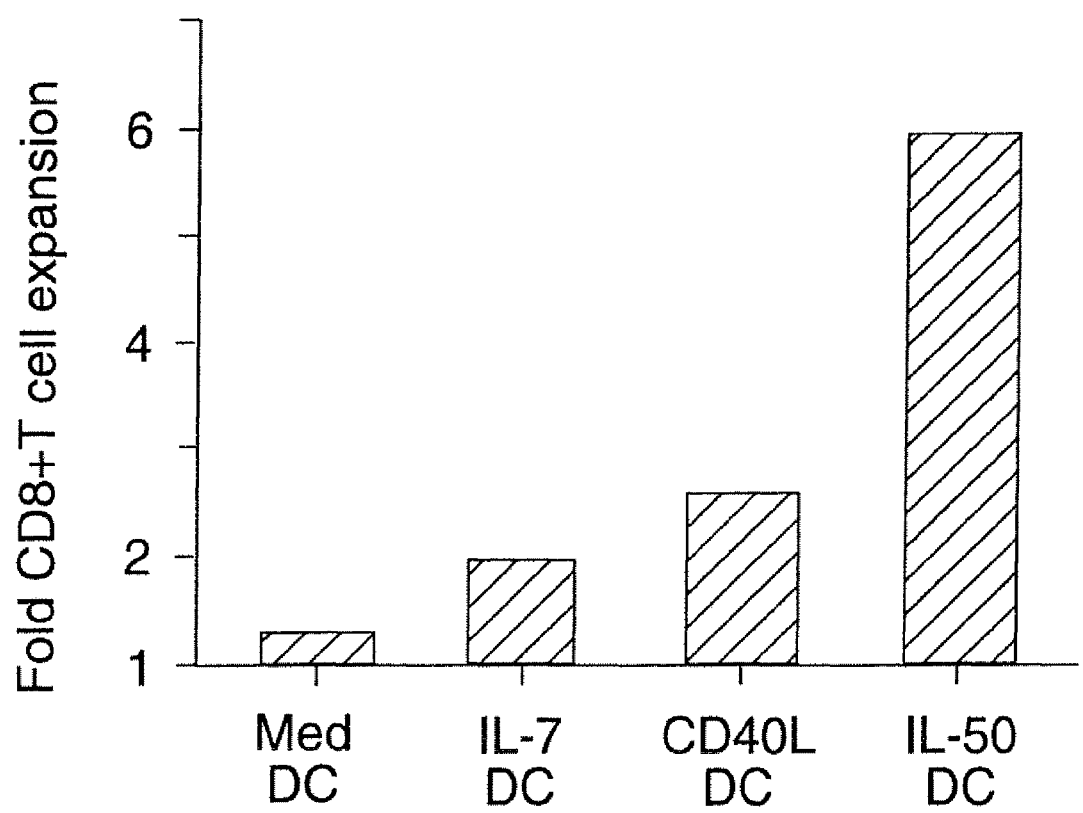
FIG. 10 shows the effect of DCs treated with medium alone, IL-B50, IL-7, and CD40-ligand on CD8 T cell expansion.

DCs were cultured for 24 hours in medium alone, IL-B50, IL-7, CD40-ligand or LPS, to prime purified naïve CD8 T cells over 6 days in coculture. IL-B50-activated DCs strongly induced expansion of allogeneic naïve CD8 T cells (FIG. 10), as well as the expression of perforin (FIG. 11).

The data herein indicate, among other things, that human IL-B50 is a novel hematopoietic cytokine most closely related to IL-7. It represents a human ortholog of mTSLP. The above results indicate that the DC subset stimulated with IL-B50 could be a potent inducer of primary T-cell mediated immune response. DCs cultured in the presence of IL-B50 were much more potent in their capacite to elicit the proliferation of naïve T cells as compared to DCs cultured in medium alone.

The human IL-B50 signaling makes use of the combination of hIL-7Rα and hRδ2, which together form a novel hematopoietic cytokine receptor. Both receptor subunits are notably present on macrophages and dendritic cells, indicating functional effects of the cytokine on those cell types, and mediating functions provided by those cell types. The human IL-B50 also promotes the phosphorylation of STAT3 and STAT5 transcription factors.

Therapeutic uses of IL-B50 are apparent. For example, SCID patients with mutations in IL-7Rα are T-cell deficient. Since IL-B50 uses IL-7Rα, IL-B50 share signaling pathway components, and may play a significant role in human T-cell differentiation and may enhance T-cell recovery in circumstances of T-cell depletion.

Likewise, IL-B50 antagonists are useful. The antagonists take various forms such as ligand muteins, antibodies to ligand, and antibodies to receptor, e.g., which block ligand binding. Since the hIL-B50 likely plays a role in the development of T- and B-cell lymphomas, then blocking IL-B50 signaling, either at the ligand or at its receptor components, is useful in treatment of some of these lymphomas.

Herein, based upon the binding studies, hIL-B50 receptor subunit mapping identified IL-7Rα and novel human receptor Rδ2 (a close relative of human γc or IL-2Rγ) as signaling receptor complex (co-expression in Ba/F3 cells delivers a proliferative signal in response to IL-B50). Receptor expression profiles indicate both IL-7Rα and Rα are primarily expressed on dendritic cells, though they are both also expressed in monocytes. The dendritic cell expression indicates a role for the cytokine in maturation of cells or pathways important in antigen presentation, indicating use of the cytokine for expansion, e.g., ex vivo, of antigen presenting cells.

All citations herein are incorporated herein by reference to the same extent as if each individual publication or patent application was specifically and individually indicated to be incorporated by reference including all figures and drawings.

Many modifications and variations of this invention, as will be apparent to one of ordinary skill in the art can be made to adapt to a particular situation, material, composition of matter, process, process step or steps, to preserve the objective, spirit and scope of the invention. All such modifications are intended to be within the scope of the claims appended hereto without departing from the spirit and scope of the invention. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. An isolated polypeptide selected from the group consisting of:
   (a) a polypeptide comprising the amino acid sequence of SEQ ID NO:2;
   (b) a polypeptide encoded by a nucleic acid molecule having SEQ ID NO:1; and
   (c) a polypeptide encoded by a nucleic acid molecule which hybridizes to the complement of the polynucleotide having SEQ ID NO:1 under conditions of about 100 mM salt and in excess of about 55° C., wherein said polypeptide is capable of binding a human IL-B50 receptor.

2. An isolated polypeptide comprising SEQ ID NO:2.

* * * * *

SEQUENCE LISTING

```
<160> NUMBER OF SEQ ID NOS: 9

<210> SEQ ID NO 1
<211> LENGTH: 468
<212> TYPE: DNA
<213> ORGANISM: Homo sapiens
<220> FEATURE:
<221> NAME/KEY: CDS
<222> LOCATION: (20)..(466)
<223> OTHER INFORMATION:
<220> FEATURE:
<221> NAME/KEY: mat_peptide
<222> LOCATION: (119)..()
<223> OTHER INFORMATION:
<220> FEATURE:
<221> NAME/KEY: misc_feature
<222> LOCATION: (301)..(301)
<223> OTHER INFORMATION: Unknown nucleotide.
```

<400> SEQUENCE: 1

```
agtgtgaaac tggggtgga atg ggg tgt cca cgt atg ttc cct ttt gcc tta      52
                      Met Gly Cys Pro Arg Met Phe Pro Phe Ala Leu
                          -30                 -25 cta tat gtt ctg tca gtt tct ttc agg aaa atc ttc atc tta caa ctt      100
Leu Tyr Val Leu Ser Val Ser Phe Arg Lys Ile Phe Ile Leu Gln Leu
    -20                 -15                 -10 gta ggg ctg gtg tta act tac gac ttc act aac tgt gac ttt gag aag      148
Val Gly Leu Val Leu Thr Tyr Asp Phe Thr Asn Cys Asp Phe Glu Lys
    -5              -1  1               5                   10 att aaa gca gcc tat ctc agt act att tct aaa gac ctg att aca tat      196
Ile Lys Ala Ala Tyr Leu Ser Thr Ile Ser Lys Asp Leu Ile Thr Tyr
                15                  20                  25 atg agt ggg acc aaa agt acc gag ttc aac aac acc gtc tct tgt agc      244
Met Ser Gly Thr Lys Ser Thr Glu Phe Asn Asn Thr Val Ser Cys Ser
            30                  35                  40 aat cgg cca cat tgc ctt act gaa atc cag agc cta acc ttc aat ccc      292
Asn Arg Pro His Cys Leu Thr Glu Ile Gln Ser Leu Thr Phe Asn Pro
        45                  50                  55 aac cgc cgn gtg cgg tcg ctc gcc aaa gaa atg ttc gcc atg aaa act      340
Asn Arg Arg Val Arg Ser Leu Ala Lys Glu Met Phe Ala Met Lys Thr
    60                  65                  70 aag gct gcc tta gct atc tgg tgc cca ggc tat tcg gaa act cag ata      388
Lys Ala Ala Leu Ala Ile Trp Cys Pro Gly Tyr Ser Glu Thr Gln Ile
75              80                  85                  90 aat gct act cag gca atg aag aag agg aga aaa agg aaa gtc aca acc      436
Asn Ala Thr Gln Ala Met Lys Lys Arg Arg Lys Arg Lys Val Thr Thr
                95                  100                 105 aat aaa tgt ctg gaa caa gtg tca caa tta aa                           468
Asn Lys Cys Leu Glu Gln Val Ser Gln Leu
        110                 115
```

<210> SEQ ID NO 2
<211> LENGTH: 149
<212> TYPE: PRT
<213> ORGANISM: Homo sapiens

<400> SEQUENCE: 2

```
Met Gly Cys Pro Arg Met Phe Pro Phe Ala Leu Leu Tyr Val Leu Ser
            -30                 -25                 -20

Val Ser Phe Arg Lys Ile Phe Ile Leu Gln Leu Val Gly Leu Val Leu
        -15                 -10                 -5

Thr Tyr Asp Phe Thr Asn Cys Asp Phe Glu Lys Ile Lys Ala Ala Tyr
-1  1               5                   10                  15

Leu Ser Thr Ile Ser Lys Asp Leu Ile Thr Tyr Met Ser Gly Thr Lys
                20                  25                  30

Ser Thr Glu Phe Asn Asn Thr Val Ser Cys Ser Asn Arg Pro His Cys
            35                  40                  45

Leu Thr Glu Ile Gln Ser Leu Thr Phe Asn Pro Asn Arg Arg Val Arg
        50                  55                  60

Ser Leu Ala Lys Glu Met Phe Ala Met Lys Thr Lys Ala Ala Leu Ala
    65                  70                  75

Ile Trp Cys Pro Gly Tyr Ser Glu Thr Gln Ile Asn Ala Thr Gln Ala
80              85                  90                  95

Met Lys Lys Arg Arg Lys Arg Lys Val Thr Thr Asn Lys Cys Leu Glu
                100                 105                 110

Gln Val Ser Gln Leu
            115
```

```
<210> SEQ ID NO 3
<211> LENGTH: 480
<212> TYPE: DNA
<213> ORGANISM: Homo sapiens
<220> FEATURE:
<221> NAME/KEY: CDS
<222> LOCATION: (1)..(477)
<223> OTHER INFORMATION:
<220> FEATURE:
<221> NAME/KEY: mat_peptide
<222> LOCATION: (85)..()
<223> OTHER INFORMATION:

<400> SEQUENCE: 3 atg ttc cct ttt gcc tta cta tat gtt ctg tca gtt tct ttc agg aaa      48
Met Phe Pro Phe Ala Leu Leu Tyr Val Leu Ser Val Ser Phe Arg Lys
        -25                 -20                 -15 atc ttc atc tta caa ctt gta ggg ctg gtg tta act tac gac ttc act      96
Ile Phe Ile Leu Gln Leu Val Gly Leu Val Leu Thr Tyr Asp Phe Thr
            -10                  -5                  -1   1 aac tgt gac ttt gag aag att aaa gca gcc tat ctc agt act att tct     144
Asn Cys Asp Phe Glu Lys Ile Lys Ala Ala Tyr Leu Ser Thr Ile Ser
  5                  10                  15                  20 aaa gac ctg att aca tat atg agt ggg acc aaa agt acc gag ttc aac     192
Lys Asp Leu Ile Thr Tyr Met Ser Gly Thr Lys Ser Thr Glu Phe Asn
                 25                  30                  35 aac acc gtc tct tgt agc aat cgg cca cat tgc ctt act gaa atc cag     240
Asn Thr Val Ser Cys Ser Asn Arg Pro His Cys Leu Thr Glu Ile Gln
             40                  45                  50 agc cta acc ttc aat ccc acc gcc ggc tgc gcg tcg ctc gcc aaa gaa     288
Ser Leu Thr Phe Asn Pro Thr Ala Gly Cys Ala Ser Leu Ala Lys Glu
             55                  60                  65 atg ttc gcc atg aaa act aag gct gcc tta gct atc tgg tgc cca ggc     336
Met Phe Ala Met Lys Thr Lys Ala Ala Leu Ala Ile Trp Cys Pro Gly
 70                  75                  80 tat tcg gaa act cag ata aat gct act cag gca atg aag aag agg aga     384
Tyr Ser Glu Thr Gln Ile Asn Ala Thr Gln Ala Met Lys Lys Arg Arg
 85                  90                  95                 100 aaa agg aaa gtc aca acc aat aaa tgt ctg gaa caa gtg tca caa tta     432
Lys Arg Lys Val Thr Thr Asn Lys Cys Leu Glu Gln Val Ser Gln Leu
                105                 110                 115 caa gga ttg tgg cgt cgc ttc aat cga cct tta ctg aaa caa cag taa     480
Gln Gly Leu Trp Arg Arg Phe Asn Arg Pro Leu Leu Lys Gln Gln
             120                 125                 130

<210> SEQ ID NO 4
<211> LENGTH: 159
<212> TYPE: PRT
<213> ORGANISM: Homo sapiens

<400> SEQUENCE: 4

Met Phe Pro Phe Ala Leu Leu Tyr Val Leu Ser Val Ser Phe Arg Lys
        -25                 -20                 -15

Ile Phe Ile Leu Gln Leu Val Gly Leu Val Leu Thr Tyr Asp Phe Thr
            -10                  -5                  -1   1

Asn Cys Asp Phe Glu Lys Ile Lys Ala Ala Tyr Leu Ser Thr Ile Ser
  5                  10                  15                  20

Lys Asp Leu Ile Thr Tyr Met Ser Gly Thr Lys Ser Thr Glu Phe Asn
                 25                  30                  35

Asn Thr Val Ser Cys Ser Asn Arg Pro His Cys Leu Thr Glu Ile Gln
             40                  45                  50

Ser Leu Thr Phe Asn Pro Thr Ala Gly Cys Ala Ser Leu Ala Lys Glu
```

```
                55                  60                  65
Met Phe Ala Met Lys Thr Lys Ala Ala Leu Ala Ile Trp Cys Pro Gly
            70                  75                  80

Tyr Ser Glu Thr Gln Ile Asn Ala Thr Gln Ala Met Lys Lys Arg Arg
 85                  90                  95                 100

Lys Arg Lys Val Thr Thr Asn Lys Cys Leu Glu Gln Val Ser Gln Leu
                105                 110                 115

Gln Gly Leu Trp Arg Arg Phe Asn Arg Pro Leu Leu Lys Gln Gln
            120                 125                 130

<210> SEQ ID NO 5
<211> LENGTH: 176
<212> TYPE: PRT
<213> ORGANISM: ovine

<400> SEQUENCE: 5

Met Phe His Val Ser Phe Arg Tyr Ile Phe Gly Ile Pro Pro Leu Ile
 1               5                  10                  15

Leu Val Leu Leu Pro Val Ala Ser Ser Asp Cys Asp Phe Ser Gly Lys
                20                  25                  30

Asp Gly Gly Ala Tyr Gln Asn Val Leu Met Val Ser Ile Asp Asp Leu
            35                  40                  45

Asp Asn Met Ile Asn Phe Asp Ser Asn Cys Leu Asn Asn Glu Pro Asn
 50                  55                  60

Phe Phe Lys Lys His Ser Cys Asp Asp Asn Lys Glu Ala Ser Phe Leu
 65                  70                  75                  80

Asn Arg Ala Ala Arg Lys Leu Lys Gln Phe Leu Lys Met Asn Ile Ser
                85                  90                  95

Asp Asp Phe Lys Leu His Leu Ser Thr Val Ser Gln Gly Thr Leu Thr
                100                 105                 110

Leu Leu Asn Cys Thr Ser Lys Gly Lys Gly Arg Lys Pro Pro Ser Leu
            115                 120                 125

Gly Glu Ala Gln Pro Thr Lys Asn Leu Glu Glu Asn Lys Ser Leu Lys
130                 135                 140

Glu Gln Arg Lys Gln Asn Asp Leu Cys Phe Leu Lys Ile Leu Leu Gln
145                 150                 155                 160

Lys Ile Lys Thr Cys Trp Asn Lys Ile Leu Arg Gly Ile Thr Glu His
                165                 170                 175

<210> SEQ ID NO 6
<211> LENGTH: 176
<212> TYPE: PRT
<213> ORGANISM: bovine

<400> SEQUENCE: 6

Met Phe His Val Ser Phe Arg Tyr Ile Phe Gly Ile Pro Pro Leu Ile
 1               5                  10                  15

Leu Val Leu Leu Pro Val Ala Ser Ser Asp Cys Asp Ile Ser Gly Lys
                20                  25                  30

Asp Gly Gly Ala Tyr Gln Asn Val Leu Met Val Asn Ile Asp Asp Leu
            35                  40                  45

Asp Asn Met Ile Asn Phe Asp Ser Asn Cys Leu Asn Asn Glu Pro Asn
 50                  55                  60

Phe Phe Lys Lys His Ser Cys Asp Asp Asn Lys Glu Ala Ser Phe Leu
 65                  70                  75                  80

Asn Arg Ala Ser Arg Lys Leu Arg Gln Phe Leu Lys Met Asn Ile Ser
                85                  90                  95
```

Asp Asp Phe Lys Leu His Leu Ser Thr Val Ser Gln Gly Thr Leu Thr
            100                 105                 110

Leu Leu Asn Cys Thr Ser Lys Gly Lys Gly Arg Lys Pro Pro Ser Leu
            115                 120                 125

Ser Glu Ala Gln Pro Thr Lys Asn Leu Glu Glu Asn Lys Ser Ser Lys
            130                 135                 140

Glu Gln Lys Lys Gln Asn Asp Leu Cys Phe Leu Lys Ile Leu Leu Gln
145                 150                 155                 160

Lys Ile Lys Thr Cys Trp Asn Lys Ile Leu Arg Gly Ile Lys Glu His
            165                 170                 175

<210> SEQ ID NO 7
<211> LENGTH: 177
<212> TYPE: PRT
<213> ORGANISM: Homo sapiens

<400> SEQUENCE: 7

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
            35                  40                  45

Leu Asp Ser Met Lys Glu Ile Gly Ser Asn Cys Leu Asn Asn Glu Phe
50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
            85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
            115                 120                 125

Leu Gly Glu Ala Gln Pro Thr Lys Ser Leu Glu Glu Asn Lys Ser Leu
            130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
            165                 170                 175

His

<210> SEQ ID NO 8
<211> LENGTH: 154
<212> TYPE: PRT
<213> ORGANISM: Mus musculus

<400> SEQUENCE: 8

Met Phe His Val Ser Phe Arg Tyr Ile Phe Gly Ile Pro Pro Leu Ile
1               5                   10                  15

Leu Val Leu Leu Pro Val Thr Ser Ser Glu Cys His Ile Lys Asp Lys
            20                  25                  30

Glu Gly Lys Ala Tyr Glu Ser Val Leu Met Ile Ser Ile Asp Glu Leu
            35                  40                  45

Asp Lys Met Thr Gly Thr Asp Ser Asn Cys Pro Asn Asn Glu Pro Asn
50                  55                  60

Phe Phe Arg Lys His Val Cys Asp Asp Thr Lys Glu Ala Ala Phe Leu

-continued

```
                65                  70                  75                  80
Asn Arg Ala Ala Arg Lys Leu Lys Gln Phe Leu Lys Met Asn Ile Ser
                    85                  90                  95

Glu Glu Phe Asn Val His Leu Leu Thr Val Ser Gln Gly Thr Gln Thr
                100                 105                 110

Leu Val Asn Cys Thr Ser Lys Glu Glu Lys Asn Val Lys Glu Gln Lys
            115                 120                 125

Lys Asn Asp Ala Cys Phe Leu Lys Arg Leu Leu Arg Glu Ile Lys Thr
        130                 135                 140

Cys Trp Asn Lys Ile Leu Lys Gly Ser Ile
145                 150

<210> SEQ ID NO 9
<211> LENGTH: 154
<212> TYPE: PRT
<213> ORGANISM: Mus musculus

<400> SEQUENCE: 9

Met Phe His Val Ser Phe Arg Tyr Ile Phe Gly Ile Pro Pro Leu Ile
1               5                   10                  15

Leu Val Leu Leu Pro Val Thr Ser Ser Asp Cys His Ile Lys Asp Lys
                20                  25                  30

Asp Gly Lys Ala Phe Gly Ser Val Leu Met Ile Ser Ile Asn Gln Leu
            35                  40                  45

Asp Lys Met Thr Gly Thr Asp Ser Asp Cys Pro Asn Asn Glu Pro Asn
        50                  55                  60

Phe Phe Lys Lys His Leu Cys Asp Asp Thr Lys Glu Ala Ala Phe Leu
65                  70                  75                  80

Asn Arg Ala Ala Arg Lys Leu Arg Gln Phe Leu Lys Met Asn Ile Ser
                    85                  90                  95

Glu Glu Phe Asn Asp His Leu Leu Arg Val Ser Asp Gly Thr Gln Thr
                100                 105                 110

Leu Val Asn Cys Thr Ser Lys Glu Glu Lys Thr Ile Lys Glu Gln Lys
            115                 120                 125

Lys Asn Asp Pro Cys Phe Leu Lys Arg Leu Leu Arg Glu Ile Lys Thr
        130                 135                 140

Cys Trp Asn Lys Ile Leu Lys Gly Ser Ile
145                 150
```